US012152272B2

(12) United States Patent
Eberhart et al.

(10) Patent No.: US 12,152,272 B2
(45) Date of Patent: Nov. 26, 2024

(54) FLUIDIC CARTRIDGE WITH VALVE MECHANISM

(71) Applicant: IntegenX Inc., Pleasanton, CA (US)

(72) Inventors: David Eberhart, Santa Clara, CA (US); William D. Nielsen, San Jose, CA (US); Helen Franklin, Santa Clara, CA (US); Stevan B. Jovanovich, Livermore, CA (US); Dennis Lehto, Santa Clara, CA (US); Kaiwan Chear, Livermore, CA (US); James Klevenberg, Livermore, CA (US); Chungsoo Charles Park, Fremont, CA (US); Corey M. Smith, Los Altos, CA (US); Philip Justus Wunderle, Oakland, CA (US); David King, Menlo Park, CA (US)

(73) Assignee: IntegenX Inc., Pleasanton, CA (US)

( * ) Notice: Subject to any disclaimer, the term of this patent is extended or adjusted under 35 U.S.C. 154(b) by 0 days.

(21) Appl. No.: 18/527,656

(22) Filed: Dec. 4, 2023

(65) Prior Publication Data
US 2024/0175075 A1    May 30, 2024

Related U.S. Application Data

(60) Continuation of application No. 17/181,228, filed on Feb. 22, 2021, now Pat. No. 11,891,650, which is a
(Continued)

(51) Int. Cl.
*C12Q 1/6806* (2018.01)
*B01L 3/00* (2006.01)
(Continued)

(52) U.S. Cl.
CPC ...... *C12Q 1/6806* (2013.01); *B01L 3/502707* (2013.01); *B01L 3/502715* (2013.01);
(Continued)

(58) Field of Classification Search
CPC . C12Q 1/6806; C12Q 1/686; B01L 3/502707; B01L 3/50273; B01L 3/502738;
(Continued)

(56) References Cited

U.S. PATENT DOCUMENTS

| 3,075,740 | A | 1/1963 | McIntosh |
| 3,352,643 | A | 11/1967 | Noboru et al. |

(Continued)

FOREIGN PATENT DOCUMENTS

| CN | 1109597 A | 10/1995 |
| CN | 1146017 A | 3/1997 |

(Continued)

OTHER PUBLICATIONS

Amendment and Request for Correction of Inventorship dated Jan. 10, 2008 in U.S. Appl. No. 10/750,533.
(Continued)

*Primary Examiner* — Brian J. Sines
(74) *Attorney, Agent, or Firm* — JONES ROBB, PLLC

(57) ABSTRACT

An instrument includes a fluidic cartridge having a body comprising a malleable material and a layer comprising a deformable material bonded to a surface of the body that seals one or more fluidic channels that communicate with one or more valve bodies formed in a surface of the body. The valve can be closed by applying pressure to the deformable material sufficient to close off a fluidic channel in the body. A cartridge interface is configured to engage the cartridge.

20 Claims, 37 Drawing Sheets

Related U.S. Application Data division of application No. 16/250,646, filed on Jan. 17, 2019, now Pat. No. 10,961,561, which is a division of application No. 15/117,053, filed as application No. PCT/US2015/028510 on Apr. 30, 2015, now Pat. No. 10,208,332.

(60) Provisional application No. 62/069,752, filed on Oct. 28, 2014, provisional application No. 62/069,473, filed on Oct. 28, 2014, provisional application No. 62/067,429, filed on Oct. 22, 2014, provisional application No. 62/067,120, filed on Oct. 22, 2014, provisional application No. 62/067,404, filed on Oct. 22, 2014, provisional application No. 62/001,533, filed on May 21, 2014.

(51) Int. Cl.
*C12Q 1/686* (2018.01)
*G01N 27/447* (2006.01)

(52) U.S. Cl.
CPC ..... *B01L 3/50273* (2013.01); *B01L 3/502738* (2013.01); *C12Q 1/686* (2013.01); *G01N 27/44743* (2013.01); *G01N 27/44791* (2013.01); *B01L 2200/027* (2013.01); *B01L 2200/0689* (2013.01); *B01L 2200/12* (2013.01); *B01L 2300/041* (2013.01); *B01L 2300/0654* (2013.01); *B01L 2300/0681* (2013.01); *B01L 2300/0848* (2013.01); *B01L 2300/087* (2013.01); *B01L 2300/123* (2013.01); *B01L 2400/0406* (2013.01); *B01L 2400/0478* (2013.01)

(58) Field of Classification Search
CPC ....... B01L 2200/027; B01L 2200/0689; B01L 2200/12; B01L 2300/041; B01L 2300/0654; B01L 2300/0681; B01L 2300/0848; B01L 2300/087; B01L 2300/123; B01L 2400/0406; B01L 2400/0478; B02L 3/502715; G01N 27/44743; G01N 27/44791
See application file for complete search history.

(56) References Cited

U.S. PATENT DOCUMENTS

| | | | |
|---|---|---|---|
| 3,433,257 | A | 3/1969 | Jensen |
| 3,568,692 | A | 3/1971 | Metzger et al. |
| 3,662,517 | A | 5/1972 | Tascher et al. |
| 4,011,351 | A | 3/1977 | Gipstein et al. |
| 4,011,357 | A | 3/1977 | Haase |
| 4,113,665 | A | 9/1978 | Law et al. |
| 4,390,307 | A | 6/1983 | Rice |
| 4,847,120 | A | 7/1989 | Gent |
| 4,963,498 | A | 10/1990 | Hillman et al. |
| 5,019,236 | A | 5/1991 | Young |
| 5,085,757 | A | 2/1992 | Karger et al. |
| 5,275,645 | A | 1/1994 | Ternoir et al. |
| 5,302,272 | A | 4/1994 | Klein |
| 5,324,401 | A | 6/1994 | Yeung et al. |
| 5,338,427 | A | 8/1994 | Shartle et al. |
| 5,364,759 | A | 11/1994 | Caskey et al. |
| 5,376,252 | A | 12/1994 | Ekstroem et al. |
| 5,387,505 | A | 2/1995 | Wu |
| 5,453,163 | A | 9/1995 | Yan |
| 5,482,836 | A | 1/1996 | Cantor et al. |
| 5,523,231 | A | 6/1996 | Reeve |
| 5,571,410 | A | 11/1996 | Swedberg et al. |
| 5,587,128 | A | 12/1996 | Wilding et al. |
| 5,589,136 | A | 12/1996 | Northrup et al. |
| 5,635,358 | A | 6/1997 | Wilding et al. |
| 5,639,428 | A | 6/1997 | Cottingham |
| 5,675,155 | A | 10/1997 | Pentoney et al. |
| 5,681,946 | A | 10/1997 | Reeve |
| 5,705,628 | A | 1/1998 | Hawkins |
| 5,705,813 | A | 1/1998 | Apffel et al. |
| 5,726,026 | A | 3/1998 | Wilding et al. |
| 5,741,462 | A | 4/1998 | Nova et al. |
| 5,750,015 | A | 5/1998 | Soane et al. |
| 5,770,029 | A | 6/1998 | Nelson et al. |
| 5,775,371 | A | 7/1998 | Pan et al. |
| 5,776,748 | A | 7/1998 | Singhvi et al. |
| 5,830,662 | A | 11/1998 | Soares et al. |
| 5,842,787 | A | 12/1998 | Kopf-Sill et al. |
| 5,856,174 | A | 1/1999 | Lipshutz et al. |
| 5,863,502 | A | 1/1999 | Southgate et al. |
| 5,872,010 | A | 2/1999 | Karger et al. |
| 5,885,470 | A | 3/1999 | Parce et al. |
| 5,898,071 | A | 4/1999 | Hawkins |
| 5,903,348 | A | 5/1999 | Melman et al. |
| 5,908,552 | A | 6/1999 | Dittmann et al. |
| 5,922,185 | A | 7/1999 | Updyke et al. |
| 5,922,591 | A | 7/1999 | Anderson et al. |
| 5,942,443 | A | 8/1999 | Parce et al. |
| 5,948,684 | A | 9/1999 | Weigl et al. |
| 5,951,262 | A | 9/1999 | Hartman |
| 5,971,158 | A | 10/1999 | Yager et al. |
| 5,994,064 | A | 11/1999 | Staub et al. |
| 6,001,229 | A | 12/1999 | Ramsey |
| 6,007,690 | A | 12/1999 | Nelson et al. |
| 6,007,775 | A | 12/1999 | Yager |
| 6,010,607 | A | 1/2000 | Ramsey |
| 6,048,100 | A | 4/2000 | Thrall et al. |
| 6,056,860 | A | 5/2000 | Amigo et al. |
| 6,073,482 | A | 6/2000 | Moles |
| 6,074,827 | A | 6/2000 | Nelson et al. |
| 6,103,083 | A | 8/2000 | Merenkova et al. |
| 6,103,199 | A | 8/2000 | Bjornson et al. |
| 6,110,343 | A | 8/2000 | Ramsey et al. |
| 6,120,184 | A | 9/2000 | Laurence et al. |
| 6,136,212 | A | 10/2000 | Mastrangelo et al. |
| 6,153,389 | A | 11/2000 | Haarer et al. |
| 6,168,948 | B1 | 1/2001 | Anderson et al. |
| 6,176,962 | B1 | 1/2001 | Soane et al. |
| 6,190,616 | B1 | 2/2001 | Jovanovich et al. |
| 6,197,595 | B1 | 3/2001 | Anderson et al. |
| 6,207,031 | B1 | 3/2001 | Adourian et al. |
| 6,235,471 | B1 | 5/2001 | Knapp et al. |
| 6,238,538 | B1 | 5/2001 | Parce et al. |
| 6,251,343 | B1 | 6/2001 | Dubrow et al. |
| 6,280,589 | B1 | 8/2001 | Manz et al. |
| 6,319,476 | B1 | 11/2001 | Victor et al. |
| 6,321,791 | B1 | 11/2001 | Chow |
| 6,322,683 | B1 | 11/2001 | Wolk et al. |
| 6,326,068 | B1 | 12/2001 | Kong et al. |
| 6,342,142 | B1 | 1/2002 | Ramsey |
| 6,348,318 | B1 | 2/2002 | Valkirs |
| 6,379,929 | B1 | 4/2002 | Burns et al. |
| 6,387,234 | B1 | 5/2002 | Yeung et al. |
| 6,387,707 | B1 | 5/2002 | Seul et al. |
| 6,391,622 | B1 | 5/2002 | Knapp et al. |
| 6,403,338 | B1 | 6/2002 | Knapp et al. |
| 6,408,878 | B2 | 6/2002 | Unger et al. |
| 6,423,536 | B1 | 7/2002 | Jovanovich et al. |
| 6,429,025 | B1 | 8/2002 | Parce et al. |
| 6,432,191 | B2 | 8/2002 | Schutt |
| 6,432,290 | B1 | 8/2002 | Harrison et al. |
| 6,454,924 | B2 | 9/2002 | Jedrzejewski et al. |
| 6,461,492 | B1 | 10/2002 | Hayashizaki et al. |
| 6,489,112 | B1 | 12/2002 | Hadd et al. |
| 6,521,188 | B1 | 2/2003 | Webster |
| 6,524,456 | B1 | 2/2003 | Ramsey et al. |
| 6,527,003 | B1 | 3/2003 | Webster |
| 6,531,041 | B1 | 3/2003 | Cong et al. |
| 6,531,282 | B1 | 3/2003 | Dau et al. |
| 6,532,997 | B1 | 3/2003 | Bedingham et al. |
| 6,533,914 | B1 | 3/2003 | Liu |
| 6,534,262 | B1 | 3/2003 | McKernan et al. |
| 6,537,757 | B1 | 3/2003 | Langmore et al. |
| 6,544,734 | B1 | 4/2003 | Briscoe et al. |

(56) References Cited

U.S. PATENT DOCUMENTS

| | | |
|---|---|---|
| 6,551,839 B2 | 4/2003 | Jovanovich et al. |
| 6,581,441 B1 | 6/2003 | Paul |
| 6,581,899 B2 | 6/2003 | Williams |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein et al. |
| 6,620,584 B1 | 9/2003 | Chee et al. |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,660,148 B2 | 12/2003 | Shoji et al. |
| 6,663,833 B1 | 12/2003 | Stave et al. |
| 6,685,442 B2 | 2/2004 | Chinn et al. |
| 6,685,678 B2 | 2/2004 | Evans et al. |
| 6,685,809 B1 | 2/2004 | Jacobson et al. |
| 6,740,219 B2 | 5/2004 | Imai et al. |
| 6,752,922 B2 | 6/2004 | Huang et al. |
| 6,764,648 B1 | 7/2004 | Roach et al. |
| 6,782,746 B1 | 8/2004 | Hasselbrink et al. |
| 6,783,649 B2 | 8/2004 | Hedberg et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,807,490 B1 | 10/2004 | Perlin |
| 6,824,663 B1 | 11/2004 | Boone |
| 6,829,753 B2 | 12/2004 | Lee et al. |
| 6,833,246 B2 | 12/2004 | Balasubramanian |
| 6,852,287 B2 | 2/2005 | Ganesan |
| 6,870,185 B2 | 3/2005 | Roach et al. |
| 6,883,774 B2 | 4/2005 | Nielsen et al. |
| 6,885,982 B2 | 4/2005 | Harris et al. |
| 6,899,137 B2 | 5/2005 | Unger et al. |
| 6,907,147 B2 | 6/2005 | Crafts et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 6,994,986 B2 | 2/2006 | Swartz et al. |
| 7,005,052 B2 | 2/2006 | Shimizu et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,049,558 B2 | 5/2006 | Baer et al. |
| 7,054,004 B2 | 5/2006 | Inaba et al. |
| 7,081,191 B2 | 7/2006 | Shoji et al. |
| 7,087,380 B2 | 8/2006 | Griffiths et al. |
| 7,097,809 B2 | 8/2006 | Van Dam et al. |
| 7,105,300 B2 | 9/2006 | Parce et al. |
| 7,118,910 B2 | 10/2006 | Unger et al. |
| 7,142,987 B2 | 11/2006 | Eggers |
| 7,157,228 B2 | 1/2007 | Hashmi et al. |
| 7,169,557 B2 | 1/2007 | Rosenblum et al. |
| 7,170,050 B2 | 1/2007 | Turner et al. |
| 7,198,759 B2 | 4/2007 | Bryning et al. |
| 7,211,388 B2 | 5/2007 | Cash et al. |
| 7,217,367 B2 | 5/2007 | Huang et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,244,599 B2 | 7/2007 | Tanner et al. |
| 7,244,961 B2 | 7/2007 | Jovanovich et al. |
| 7,258,744 B2 | 8/2007 | Sakurada et al. |
| 7,258,774 B2 | 8/2007 | Chou et al. |
| 7,279,146 B2 | 10/2007 | Nassef et al. |
| 7,282,361 B2 | 10/2007 | Hodge |
| 7,312,085 B2 | 12/2007 | Chou et al. |
| 7,312,611 B1 | 12/2007 | Harrison et al. |
| 7,318,912 B2 | 1/2008 | Pezzuto et al. |
| 7,323,305 B2 | 1/2008 | Leamon et al. |
| 7,329,388 B2 | 2/2008 | Guzman |
| 7,361,471 B2 | 4/2008 | Gerdes et al. |
| 7,419,578 B2 | 9/2008 | Sakai et al. |
| 7,438,856 B2 | 10/2008 | Jedrzejewski et al. |
| 7,445,926 B2 | 11/2008 | Mathies et al. |
| 7,473,342 B2 | 1/2009 | Ugai et al. |
| 7,473,397 B2 | 1/2009 | Griffin et al. |
| 7,486,865 B2 | 2/2009 | Foquet et al. |
| 7,488,603 B2 | 2/2009 | Gjerde et al. |
| 7,501,237 B2 | 3/2009 | Solus et al. |
| 7,526,741 B2 | 4/2009 | Lee et al. |
| 7,531,076 B2 | 5/2009 | Hayashizaki et al. |
| 7,537,886 B1 | 5/2009 | Nazarenko et al. |
| 7,575,865 B2 | 8/2009 | Leamon et al. |
| 7,584,240 B2 | 9/2009 | Eggers |
| 7,589,184 B2 | 9/2009 | Hogan et al. |
| 7,595,200 B2 | 9/2009 | Bedingham et al. |
| 7,645,580 B2 | 1/2010 | Barber et al. |
| 7,691,614 B2 | 4/2010 | Senapathy |
| 7,704,735 B2 | 4/2010 | Facer et al. |
| 7,718,422 B2 | 5/2010 | Chaton et al. |
| 7,718,442 B2 | 5/2010 | Davis et al. |
| 7,744,737 B1 | 6/2010 | James et al. |
| 7,745,207 B2 | 6/2010 | Jovanovich et al. |
| 7,749,365 B2 | 7/2010 | Nguyen et al. |
| 7,749,737 B2 | 7/2010 | McBride et al. |
| 7,763,453 B2 | 7/2010 | Clemmens et al. |
| 7,766,033 B2 | 8/2010 | Mathies et al. |
| 7,774,737 B2 | 8/2010 | Gallatin et al. |
| 7,785,458 B2 | 8/2010 | Shimizu et al. |
| 7,785,770 B2 | 8/2010 | Spector et al. |
| 7,790,368 B1 | 9/2010 | Fukuzono |
| 7,799,553 B2 | 9/2010 | Mathies et al. |
| 7,803,281 B2 | 9/2010 | Davies |
| 7,817,273 B2 | 10/2010 | Bahatt et al. |
| 7,832,429 B2 | 11/2010 | Young et al. |
| 7,863,357 B2 | 1/2011 | Madabhushi et al. |
| 7,867,713 B2 | 1/2011 | Nasarabadi |
| 7,885,770 B2 | 2/2011 | Gill et al. |
| 7,892,856 B2 | 2/2011 | Grate et al. |
| 7,942,160 B2 | 5/2011 | Jeon et al. |
| 7,943,305 B2 | 5/2011 | Korlach et al. |
| 7,959,875 B2 | 6/2011 | Zhou et al. |
| 7,976,789 B2 | 7/2011 | Kenis et al. |
| 7,976,795 B2 | 7/2011 | Zhou et al. |
| 7,998,708 B2 | 8/2011 | Handique et al. |
| 8,007,746 B2 | 8/2011 | Unger et al. |
| 8,018,593 B2 | 9/2011 | Tan et al. |
| 8,053,192 B2 | 11/2011 | Bignell et al. |
| RE43,122 E | 1/2012 | Harrison et al. |
| 8,142,635 B2 | 3/2012 | Shimizu et al. |
| 8,221,990 B2 | 7/2012 | Mori et al. |
| 8,222,023 B2 | 7/2012 | Battrell et al. |
| 8,268,263 B2 | 9/2012 | Campbell et al. |
| 8,280,208 B2 | 10/2012 | Wellbrock et al. |
| 8,283,165 B2 | 10/2012 | Hogan et al. |
| 8,313,941 B2 | 11/2012 | Takayama et al. |
| 8,337,777 B2 | 12/2012 | Nurse et al. |
| 8,388,908 B2 | 3/2013 | Blaga et al. |
| 8,394,642 B2 | 3/2013 | Jovanovich et al. |
| 8,398,642 B2 | 3/2013 | Weekes |
| 8,420,318 B2 | 4/2013 | Mathies et al. |
| 8,431,340 B2 | 4/2013 | Jovanovich et al. |
| 8,431,384 B2 | 4/2013 | Hogan et al. |
| 8,501,305 B2 | 8/2013 | Barlow |
| 8,512,538 B2 | 8/2013 | Majlof et al. |
| 8,551,714 B2 | 10/2013 | Jovanovich et al. |
| 8,557,517 B2 | 10/2013 | Apetoh et al. |
| 8,557,518 B2 | 10/2013 | Jovanovich et al. |
| 8,562,918 B2 | 10/2013 | Jovanovich et al. |
| 8,584,703 B2 | 11/2013 | Kobrin et al. |
| 8,672,532 B2 | 3/2014 | Jovanovich et al. |
| 8,748,165 B2 | 6/2014 | Vangbo et al. |
| 8,763,642 B2 | 7/2014 | Vangbo |
| 8,841,116 B2 | 9/2014 | Mathies et al. |
| 8,894,946 B2 | 11/2014 | Nielsen et al. |
| 8,911,433 B2 | 12/2014 | Hixon et al. |
| 9,012,236 B2 | 4/2015 | Jovanovich et al. |

(56) References Cited

U.S. PATENT DOCUMENTS

| | | | |
|---|---|---|---|
| 9,121,058 B2 | 9/2015 | Stern et al. | |
| 9,158,064 B2 | 10/2015 | Saito et al. | |
| 9,291,284 B2 | 3/2016 | Penterman et al. | |
| 9,341,284 B2 | 5/2016 | Vangbo | |
| D772,086 S | 11/2016 | Schueren et al. | |
| 9,592,501 B2 | 3/2017 | Jarvius et al. | |
| 9,663,819 B2 | 5/2017 | Jovanovich et al. | |
| 10,208,332 B2* | 2/2019 | Eberhart | B01L 3/502738 |
| 10,961,561 B2* | 3/2021 | Eberhart | C12Q 1/686 |
| 11,891,650 B2* | 2/2024 | Eberhart | B01L 3/502761 |
| 2001/0012612 A1 | 8/2001 | Petersen et al. | |
| 2001/0041357 A1 | 11/2001 | Fouillet et al. | |
| 2002/0003895 A1 | 1/2002 | Some | |
| 2002/0022261 A1 | 2/2002 | Anderson et al. | |
| 2002/0022587 A1 | 2/2002 | Ferguson et al. | |
| 2002/0025529 A1 | 2/2002 | Quake et al. | |
| 2002/0025576 A1 | 2/2002 | Northrup et al. | |
| 2002/0042125 A1 | 4/2002 | Petersen et al. | |
| 2002/0045189 A1 | 4/2002 | Imajo et al. | |
| 2002/0047003 A1 | 4/2002 | Bedingham et al. | |
| 2002/0048536 A1 | 4/2002 | Bergh et al. | |
| 2002/0051992 A1 | 5/2002 | Bridgham et al. | |
| 2002/0055167 A1 | 5/2002 | Pourahmadi et al. | |
| 2002/0058332 A1 | 5/2002 | Quake et al. | |
| 2002/0068357 A1 | 6/2002 | Mathies et al. | |
| 2002/0098097 A1 | 7/2002 | Singh | |
| 2002/0110900 A1 | 8/2002 | Jovanovich et al. | |
| 2002/0113707 A1 | 8/2002 | Grunes et al. | |
| 2002/0115201 A1 | 8/2002 | Barenburg et al. | |
| 2002/0119480 A1 | 8/2002 | Weir et al. | |
| 2002/0119482 A1 | 8/2002 | Nelson et al. | |
| 2002/0137039 A1 | 9/2002 | Gessner | |
| 2002/0139084 A1 | 10/2002 | Tobolka | |
| 2002/0151089 A1 | 10/2002 | Chapman et al. | |
| 2002/0157951 A1 | 10/2002 | Foret et al. | |
| 2002/0160361 A1 | 10/2002 | Loehrlein et al. | |
| 2002/0187560 A1 | 12/2002 | Pezzuto et al. | |
| 2003/0007067 A1 | 1/2003 | Masuda et al. | |
| 2003/0008308 A1 | 1/2003 | Enzelberger et al. | |
| 2003/0019753 A1 | 1/2003 | Ogle et al. | |
| 2003/0021734 A1 | 1/2003 | Vann et al. | |
| 2003/0029724 A1 | 2/2003 | Derand et al. | |
| 2003/0070677 A1 | 4/2003 | Handique et al. | |
| 2003/0087425 A1 | 5/2003 | Eggers | |
| 2003/0087446 A1 | 5/2003 | Eggers | |
| 2003/0087455 A1 | 5/2003 | Eggers et al. | |
| 2003/0088657 A1 | 5/2003 | Eggers | |
| 2003/0095897 A1 | 5/2003 | Grate et al. | |
| 2003/0104466 A1 | 6/2003 | Knapp et al. | |
| 2003/0129755 A1 | 7/2003 | Sadler et al. | |
| 2003/0162304 A1 | 8/2003 | Dority et al. | |
| 2003/0175706 A1 | 9/2003 | Zhang | |
| 2003/0197139 A1 | 10/2003 | Williams | |
| 2003/0198573 A1 | 10/2003 | Forood et al. | |
| 2003/0215369 A1 | 11/2003 | Eggers et al. | |
| 2003/0217923 A1 | 11/2003 | Harrison et al. | |
| 2004/0003997 A1 | 1/2004 | Anazawa et al. | |
| 2004/0013536 A1 | 1/2004 | Hower et al. | |
| 2004/0014091 A1 | 1/2004 | Duck et al. | |
| 2004/0018611 A1 | 1/2004 | Ward et al. | |
| 2004/0021068 A1 | 2/2004 | Staats | |
| 2004/0022676 A1 | 2/2004 | Hamilton et al. | |
| 2004/0037739 A1 | 2/2004 | McNeely et al. | |
| 2004/0038385 A1 | 2/2004 | Langlois et al. | |
| 2004/0053290 A1 | 3/2004 | Terbrueggen et al. | |
| 2004/0063217 A1 | 4/2004 | Webster et al. | |
| 2004/0072278 A1 | 4/2004 | Chou et al. | |
| 2004/0086427 A1 | 5/2004 | Childers et al. | |
| 2004/0086870 A1 | 5/2004 | Tyvoll et al. | |
| 2004/0101966 A1 | 5/2004 | Davis et al. | |
| 2004/0115838 A1 | 6/2004 | Quake et al. | |
| 2004/0132170 A1 | 7/2004 | Storek et al. | |
| 2004/0146452 A1 | 7/2004 | Fujieda et al. | |
| 2004/0151349 A1 | 8/2004 | Milne et al. | |
| 2004/0151629 A1 | 8/2004 | Pease et al. | |
| 2004/0185484 A1 | 9/2004 | Costa et al. | |
| 2004/0197845 A1 | 10/2004 | Hassibi et al. | |
| 2004/0200724 A1 | 10/2004 | Fujii et al. | |
| 2004/0209354 A1 | 10/2004 | Mathies et al. | |
| 2004/0217004 A1 | 11/2004 | Hayashizaki et al. | |
| 2004/0219533 A1 | 11/2004 | Davis et al. | |
| 2004/0224380 A1 | 11/2004 | Chou et al. | |
| 2005/0026181 A1 | 2/2005 | Davis et al. | |
| 2005/0026300 A1 | 2/2005 | Samper et al. | |
| 2005/0042656 A1 | 2/2005 | Davis et al. | |
| 2005/0047967 A1 | 3/2005 | Chuang et al. | |
| 2005/0053952 A1 | 3/2005 | Hong et al. | |
| 2005/0142663 A1 | 6/2005 | Parthasarathy et al. | |
| 2005/0161326 A1 | 7/2005 | Morita et al. | |
| 2005/0161669 A1 | 7/2005 | Jovanovich et al. | |
| 2005/0181394 A1 | 8/2005 | Steemers et al. | |
| 2005/0201901 A1 | 9/2005 | Grossman et al. | |
| 2005/0221373 A1 | 10/2005 | Enzelberger et al. | |
| 2005/0224134 A1 | 10/2005 | Yin et al. | |
| 2005/0224352 A1 | 10/2005 | Harrison et al. | |
| 2005/0241941 A1 | 11/2005 | Parce et al. | |
| 2005/0247357 A1 | 11/2005 | Welle | |
| 2005/0250199 A1 | 11/2005 | Anderson et al. | |
| 2005/0255000 A1 | 11/2005 | Yamamoto et al. | |
| 2005/0255003 A1 | 11/2005 | Summersgill et al. | |
| 2005/0255007 A1 | 11/2005 | Yamada et al. | |
| 2005/0266582 A1 | 12/2005 | Modlin et al. | |
| 2005/0287572 A1 | 12/2005 | Mathies et al. | |
| 2006/0014177 A1 | 1/2006 | Hogan et al. | |
| 2006/0027456 A1 | 2/2006 | Harrison et al. | |
| 2006/0040300 A1 | 2/2006 | Dapprich et al. | |
| 2006/0057209 A1 | 3/2006 | Chapman et al. | |
| 2006/0073484 A1 | 4/2006 | Mathies et al. | |
| 2006/0076068 A1 | 4/2006 | Young et al. | |
| 2006/0140051 A1 | 6/2006 | Kim et al. | |
| 2006/0163143 A1 | 7/2006 | Chirica et al. | |
| 2006/0177832 A1 | 8/2006 | Brenner | |
| 2006/0186043 A1 | 8/2006 | Covey et al. | |
| 2006/0210994 A1 | 9/2006 | Joyce | |
| 2006/0210998 A1 | 9/2006 | Kettlitz et al. | |
| 2006/0260941 A1 | 11/2006 | Tan et al. | |
| 2006/0263789 A1 | 11/2006 | Kincaid | |
| 2006/0266645 A1 | 11/2006 | Chen et al. | |
| 2006/0292032 A1 | 12/2006 | Hataoka et al. | |
| 2007/0015179 A1 | 1/2007 | Klapperich et al. | |
| 2007/0017812 A1 | 1/2007 | Bousse | |
| 2007/0020654 A1 | 1/2007 | Blume et al. | |
| 2007/0031865 A1 | 2/2007 | Willoughby | |
| 2007/0034025 A1 | 2/2007 | Pant et al. | |
| 2007/0105163 A1 | 5/2007 | Grate et al. | |
| 2007/0122819 A1 | 5/2007 | Wu et al. | |
| 2007/0175756 A1 | 8/2007 | Nguyen et al. | |
| 2007/0183935 A1 | 8/2007 | Clemmens et al. | |
| 2007/0184463 A1 | 8/2007 | Molho et al. | |
| 2007/0184547 A1 | 8/2007 | Handique et al. | |
| 2007/0202531 A1 | 8/2007 | Grover | |
| 2007/0204497 A1 | 9/2007 | De La Huerga | |
| 2007/0218485 A1 | 9/2007 | Davis et al. | |
| 2007/0237686 A1 | 10/2007 | Mathies et al. | |
| 2007/0238109 A1 | 10/2007 | Min et al. | |
| 2007/0248958 A1 | 10/2007 | Jovanovich et al. | |
| 2007/0263049 A1 | 11/2007 | Preckel et al. | |
| 2007/0292941 A1 | 12/2007 | Handique et al. | |
| 2007/0297947 A1 | 12/2007 | Sommers et al. | |
| 2008/0014576 A1 | 1/2008 | Jovanovich et al. | |
| 2008/0014589 A1 | 1/2008 | Link et al. | |
| 2008/0027756 A1 | 1/2008 | Gabriel et al. | |
| 2008/0047836 A1 | 2/2008 | Strand et al. | |
| 2008/0064610 A1 | 3/2008 | Lipovsek et al. | |
| 2008/0124723 A1 | 5/2008 | Dale et al. | |
| 2008/0131904 A1 | 6/2008 | Parce et al. | |
| 2008/0138809 A1 | 6/2008 | Kapur et al. | |
| 2008/0160630 A1 | 7/2008 | Liu et al. | |
| 2008/0179255 A1 | 7/2008 | Jung et al. | |
| 2008/0179555 A1 | 7/2008 | Landers et al. | |
| 2008/0217178 A1 | 9/2008 | Ben-Asouli et al. | |
| 2008/0237146 A1 | 10/2008 | Harrison et al. | |
| 2008/0241844 A1 | 10/2008 | Kellogg | |
| 2008/0242560 A1 | 10/2008 | Gunderson et al. | |

(56) References Cited

U.S. PATENT DOCUMENTS

| | | |
|---|---|---|
| 2008/0257437 A1 | 10/2008 | Fernandes et al. |
| 2008/0262474 A1 | 10/2008 | Northrop |
| 2008/0262747 A1 | 10/2008 | Kain et al. |
| 2008/0281090 A1 | 11/2008 | Lee et al. |
| 2008/0302732 A1 | 12/2008 | Soh et al. |
| 2008/0307117 A1 | 12/2008 | Muller-Cohn et al. |
| 2008/0311585 A1 | 12/2008 | Gao et al. |
| 2009/0004494 A1 | 1/2009 | Blenke et al. |
| 2009/0011959 A1 | 1/2009 | Costa et al. |
| 2009/0020427 A1 | 1/2009 | Tan et al. |
| 2009/0023603 A1 | 1/2009 | Selden et al. |
| 2009/0026082 A1 | 1/2009 | Rothberg et al. |
| 2009/0035770 A1 | 2/2009 | Mathies et al. |
| 2009/0053799 A1 | 2/2009 | Chang-Yen et al. |
| 2009/0056822 A1 | 3/2009 | Young et al. |
| 2009/0060797 A1 | 3/2009 | Mathies et al. |
| 2009/0084679 A1 | 4/2009 | Harrison et al. |
| 2009/0087850 A1 | 4/2009 | Eid et al. |
| 2009/0092970 A1 | 4/2009 | Williams |
| 2009/0134069 A1 | 5/2009 | Handique |
| 2009/0137413 A1 | 5/2009 | Mehta et al. |
| 2009/0148933 A1 | 6/2009 | Battrell et al. |
| 2009/0155123 A1 | 6/2009 | Williams et al. |
| 2009/0178934 A1 | 7/2009 | Jarvius et al. |
| 2009/0181411 A1 | 7/2009 | Battrell et al. |
| 2009/0183990 A1 | 7/2009 | Shoji et al. |
| 2009/0233325 A1 | 9/2009 | Mori et al. |
| 2009/0253181 A1 | 10/2009 | Vangbo et al. |
| 2009/0269504 A1 | 10/2009 | Liao |
| 2009/0275038 A1 | 11/2009 | Hodge |
| 2009/0286327 A1 | 11/2009 | Cho et al. |
| 2009/0311804 A1 | 12/2009 | McBrady et al. |
| 2009/0314970 A1 | 12/2009 | McAvoy et al. |
| 2009/0314972 A1 | 12/2009 | McAvoy et al. |
| 2009/0325183 A1 | 12/2009 | Lao et al. |
| 2009/0325276 A1 | 12/2009 | Battrell et al. |
| 2010/0010472 A1 | 1/2010 | Moore |
| 2010/0029915 A1 | 2/2010 | Duthie et al. |
| 2010/0034986 A1 | 2/2010 | Kodas et al. |
| 2010/0035252 A1 | 2/2010 | Rothberg et al. |
| 2010/0068723 A1 | 3/2010 | Jovanovich et al. |
| 2010/0075858 A1 | 3/2010 | Davis et al. |
| 2010/0092948 A1 | 4/2010 | Davis et al. |
| 2010/0093068 A1 | 4/2010 | Williams |
| 2010/0111770 A1 | 5/2010 | Hwang et al. |
| 2010/0129810 A1 | 5/2010 | Greiner et al. |
| 2010/0137143 A1 | 6/2010 | Rothberg et al. |
| 2010/0165784 A1 | 7/2010 | Jovanovich et al. |
| 2010/0172898 A1 | 7/2010 | Doyle et al. |
| 2010/0173392 A1 | 7/2010 | Davis et al. |
| 2010/0173398 A1 | 7/2010 | Peterman |
| 2010/0178210 A1 | 7/2010 | Hogan et al. |
| 2010/0197507 A1 | 8/2010 | Rothberg et al. |
| 2010/0209957 A1 | 8/2010 | Hogan et al. |
| 2010/0210008 A1 | 8/2010 | Strand et al. |
| 2010/0218623 A1 | 9/2010 | Eggers et al. |
| 2010/0221726 A1 | 9/2010 | Zenhausern et al. |
| 2010/0228513 A1 | 9/2010 | Roth et al. |
| 2010/0233696 A1 | 9/2010 | Joseph et al. |
| 2010/0243916 A1 | 9/2010 | Maurer et al. |
| 2010/0248363 A1 | 9/2010 | Hogan et al. |
| 2010/0265068 A1 | 10/2010 | Brackmann et al. |
| 2010/0266432 A1 | 10/2010 | Pirk et al. |
| 2010/0285578 A1 | 11/2010 | Selden et al. |
| 2010/0285606 A1 | 11/2010 | Phillips et al. |
| 2010/0285975 A1 | 11/2010 | Mathies et al. |
| 2010/0291666 A1 | 11/2010 | Collier et al. |
| 2010/0303687 A1 | 12/2010 | Blaga et al. |
| 2010/0304355 A1 | 12/2010 | Shuler et al. |
| 2010/0304986 A1 | 12/2010 | Chen et al. |
| 2011/0003301 A1 | 1/2011 | Raymond et al. |
| 2011/0005932 A1 | 1/2011 | Jovanovich et al. |
| 2011/0008785 A1 | 1/2011 | Tan et al. |
| 2011/0008813 A1 | 1/2011 | Dilleen et al. |
| 2011/0014606 A1 | 1/2011 | Steinmetzer et al. |
| 2011/0027913 A1 | 2/2011 | Bau et al. |
| 2011/0038758 A1 | 2/2011 | Akaba et al. |
| 2011/0039303 A1 | 2/2011 | Jovanovich et al. |
| 2011/0041935 A1 | 2/2011 | Zhou et al. |
| 2011/0045505 A1 | 2/2011 | Warthoe et al. |
| 2011/0053784 A1 | 3/2011 | Unger et al. |
| 2011/0067098 A1 | 3/2011 | Nelson et al. |
| 2011/0070578 A1 | 3/2011 | Bell et al. |
| 2011/0124049 A1 | 5/2011 | Li et al. |
| 2011/0126910 A1 | 6/2011 | May |
| 2011/0126911 A1 | 6/2011 | Kobrin et al. |
| 2011/0127222 A1 | 6/2011 | Chang-Yen et al. |
| 2011/0136179 A1 | 6/2011 | Bin et al. |
| 2011/0137018 A1 | 6/2011 | Chang-Yen et al. |
| 2011/0171086 A1 | 7/2011 | Prins et al. |
| 2011/0172403 A1 | 7/2011 | Harrold |
| 2011/0186466 A1 | 8/2011 | Kurowski et al. |
| 2011/0189678 A1 | 8/2011 | McBride et al. |
| 2011/0195495 A1 | 8/2011 | Selden et al. |
| 2011/0206576 A1 | 8/2011 | Woudenberg et al. |
| 2011/0207140 A1 | 8/2011 | Handique et al. |
| 2011/0212440 A1 | 9/2011 | Movy et al. |
| 2011/0212446 A1 | 9/2011 | Wang et al. |
| 2011/0212466 A1 | 9/2011 | Deshayes et al. |
| 2011/0223605 A1 | 9/2011 | Bienvenue et al. |
| 2011/0229897 A1 | 9/2011 | Bell et al. |
| 2011/0229898 A1 | 9/2011 | Bell et al. |
| 2011/0256530 A1 | 10/2011 | Hogan |
| 2011/0312614 A1 | 12/2011 | Selden et al. |
| 2012/0055798 A1 | 3/2012 | Selden et al. |
| 2012/0100522 A1 | 4/2012 | Saghbini et al. |
| 2012/0181460 A1 | 7/2012 | Eberhart et al. |
| 2012/0240127 A1 | 9/2012 | Brittenham et al. |
| 2012/0267247 A1 | 10/2012 | Tan et al. |
| 2012/0279638 A1 | 11/2012 | Zhou et al. |
| 2012/0290648 A1 | 11/2012 | Sharkey |
| 2012/0308987 A1 | 12/2012 | Hogan et al. |
| 2012/0309637 A1 | 12/2012 | Schumm et al. |
| 2012/0315635 A1 | 12/2012 | Vangbo et al. |
| 2012/0322666 A1 | 12/2012 | Pham et al. |
| 2013/0053255 A1 | 2/2013 | Vangbo et al. |
| 2013/0074944 A1 | 3/2013 | Van Gelder |
| 2013/0084565 A1 | 4/2013 | Landers et al. |
| 2013/0105017 A1 | 5/2013 | Zhou et al. |
| 2013/0115607 A1 | 5/2013 | Nielsen et al. |
| 2013/0131994 A1 | 5/2013 | Birdwell et al. |
| 2013/0139895 A1 | 6/2013 | Vangbo |
| 2013/0202182 A1 | 8/2013 | Rowe |
| 2013/0203634 A1 | 8/2013 | Jovanovich et al. |
| 2013/0209326 A1 | 8/2013 | Williams et al. |
| 2013/0210126 A1 | 8/2013 | Williams et al. |
| 2013/0210129 A1 | 8/2013 | Selden et al. |
| 2013/0213810 A1 | 8/2013 | Tan et al. |
| 2013/0215116 A1 | 8/2013 | Siddique et al. |
| 2013/0217026 A1 | 8/2013 | Egan et al. |
| 2013/0224846 A1 | 8/2013 | Jovanovich et al. |
| 2013/0230906 A1 | 9/2013 | Martinelli et al. |
| 2013/0240140 A1 | 9/2013 | Kurowski et al. |
| 2013/0260380 A1 | 10/2013 | Hall et al. |
| 2013/0287645 A1 | 10/2013 | Shaikh et al. |
| 2013/0336545 A1 | 12/2013 | Pritikin et al. |
| 2013/0344475 A1 | 12/2013 | Jovanovich et al. |
| 2014/0045704 A1 | 2/2014 | Jovanovich et al. |
| 2014/0065628 A1 | 3/2014 | Van Gelder et al. |
| 2014/0065689 A1 | 3/2014 | Hogan et al. |
| 2014/0073043 A1 | 3/2014 | Holmes |
| 2014/0081657 A1 | 3/2014 | Neuvonen et al. |
| 2014/0161686 A1 | 6/2014 | Bort et al. |
| 2014/0170645 A1 | 6/2014 | Jovanovich et al. |
| 2014/0246618 A1 | 9/2014 | Zhou et al. |
| 2014/0370519 A1 | 12/2014 | Vangbo et al. |
| 2015/0021502 A1 | 1/2015 | Vangbo |
| 2015/0024436 A1 | 1/2015 | Eberhart et al. |
| 2015/0025915 A1 | 1/2015 | Lekas |
| 2015/0078552 A1 | 3/2015 | Perlin |
| 2015/0088772 A1 | 3/2015 | Shwartz et al. |
| 2015/0121522 A1 | 4/2015 | Guido |
| 2015/0136602 A1 | 5/2015 | Jovanovich et al. |
| 2015/0136604 A1 | 5/2015 | Nielsen et al. |

(56) References Cited

U.S. PATENT DOCUMENTS

| | | |
|---|---|---|
| 2015/0210999 A1 | 7/2015 | Sahoyama et al. |
| 2016/0016140 A1 | 1/2016 | Jovanovich et al. |
| 2016/0053314 A1 | 2/2016 | Jovanovich et al. |
| 2016/0096176 A1 | 4/2016 | Jarvius et al. |
| 2016/0116439 A1 | 4/2016 | Kindwall et al. |
| 2016/0175840 A1 | 6/2016 | Ingber et al. |
| 2016/0305972 A1 | 10/2016 | Ogg et al. |
| 2016/0367981 A1 | 12/2016 | Wunderle et al. |
| 2017/0002399 A1 | 1/2017 | Eberhart et al. |
| 2017/0016853 A1 | 1/2017 | Maher |
| 2017/0109593 A1 | 4/2017 | Schueren et al. |
| 2017/0176385 A1 | 6/2017 | Walton et al. |
| 2017/0197213 A1 | 7/2017 | Nielsen et al. |
| 2018/0262557 A1 | 9/2018 | Schueren et al. |
| 2018/0293680 A1 | 10/2018 | Schueren et al. |

FOREIGN PATENT DOCUMENTS

| | | |
|---|---|---|
| CN | 1354692 A | 6/2002 |
| CN | 1593338 A | 3/2005 |
| CN | 101004423 A | 7/2007 |
| CN | 101312759 A | 11/2008 |
| CN | 101553306 A | 10/2009 |
| CN | 102459565 A | 5/2012 |
| EP | 0455971 A1 | 11/1991 |
| EP | 0459241 A1 | 12/1991 |
| EP | 0637999 A1 | 2/1995 |
| EP | 0527905 B1 | 11/1995 |
| EP | 1065378 A2 | 1/2001 |
| EP | 1367388 A1 | 12/2003 |
| EP | 1411340 A2 | 4/2004 |
| EP | 1658890 A2 | 5/2006 |
| EP | 1706735 A2 | 10/2006 |
| EP | 2345739 A2 | 7/2011 |
| EP | 2418480 A2 | 2/2012 |
| EP | 2418840 A2 | 2/2012 |
| EP | 1537412 B1 | 1/2013 |
| JP | 10-206384 A | 8/1998 |
| JP | 11-248679 A | 9/1999 |
| JP | 2003-536058 A | 12/2003 |
| JP | 2004-025159 A | 1/2004 |
| JP | 2004-108285 A | 4/2004 |
| JP | 2004-180594 A | 7/2004 |
| JP | 2005-323519 A | 11/2005 |
| JP | 2005-337415 A | 12/2005 |
| JP | 2005-345463 A | 12/2005 |
| JP | 2007-155491 A | 6/2007 |
| JP | 2007-198765 A | 8/2007 |
| JP | 2008-513022 A | 5/2008 |
| JP | 2008-851022 | 5/2008 |
| WO | 96/04547 A1 | 2/1996 |
| WO | 98/52691 A1 | 11/1998 |
| WO | 98/53300 A2 | 11/1998 |
| WO | 99/36766 A1 | 7/1999 |
| WO | 99/40174 A1 | 8/1999 |
| WO | 00/40712 A1 | 7/2000 |
| WO | 00/60362 A1 | 10/2000 |
| WO | 00/61198 A1 | 10/2000 |
| WO | 01/01025 A2 | 1/2001 |
| WO | 01/02846 A1 | 1/2001 |
| WO | 01/38865 A1 | 5/2001 |
| WO | 01/85341 A1 | 11/2001 |
| WO | 02/24949 A1 | 3/2002 |
| WO | 02/41995 A1 | 5/2002 |
| WO | 02/43615 A2 | 6/2002 |
| WO | 02/59592 A2 | 8/2002 |
| WO | 03/62462 A2 | 7/2003 |
| WO | 03/85379 A2 | 10/2003 |
| WO | 2004/038363 A2 | 5/2004 |
| WO | 2004/061085 A2 | 7/2004 |
| WO | 2004/062804 A1 | 7/2004 |
| WO | 2004/080597 A2 | 9/2004 |
| WO | 2004/092721 A1 | 10/2004 |
| WO | 2004/098757 A2 | 11/2004 |
| WO | 2005/047882 A2 | 5/2005 |
| WO | 2005/072858 A1 | 8/2005 |
| WO | 2005/075081 A1 | 8/2005 |
| WO | 2005/121308 A1 | 12/2005 |
| WO | 2005/123950 A2 | 12/2005 |
| WO | 2006/032044 A2 | 3/2006 |
| WO | 2007/002579 A2 | 1/2007 |
| WO | 2007/064635 A1 | 6/2007 |
| WO | 2007/082480 A2 | 7/2007 |
| WO | 2008/012014 A1 | 1/2008 |
| WO | 2008/012104 A2 | 1/2008 |
| WO | 2008/024319 A2 | 2/2008 |
| WO | 2008/030631 A2 | 3/2008 |
| WO | 2008/039875 A1 | 4/2008 |
| WO | 2008/115626 A2 | 9/2008 |
| WO | 2009/008236 A1 | 1/2009 |
| WO | 2009/015296 A1 | 1/2009 |
| WO | 2009/108260 A2 | 9/2009 |
| WO | 2009/129415 A1 | 10/2009 |
| WO | 2010/013076 A1 | 2/2010 |
| WO | 2010/041174 A1 | 4/2010 |
| WO | 2010/041231 A2 | 4/2010 |
| WO | 2010/042784 A2 | 4/2010 |
| WO | 2010/077322 A1 | 7/2010 |
| WO | 2010/109392 A1 | 9/2010 |
| WO | 2010/121326 A1 | 10/2010 |
| WO | 2010/130762 A2 | 11/2010 |
| WO | 2010/141921 A1 | 12/2010 |
| WO | 2011/003941 A1 | 1/2011 |
| WO | 2011/011172 A1 | 1/2011 |
| WO | 2011/012621 A1 | 2/2011 |
| WO | 2011/034621 A2 | 3/2011 |
| WO | 2011/056215 A1 | 5/2011 |
| WO | 2011/068762 A1 | 6/2011 |
| WO | 2011/084703 A2 | 7/2011 |
| WO | 2011/094577 A2 | 8/2011 |
| WO | 2011/123801 A1 | 10/2011 |
| WO | 2011/150232 A2 | 12/2011 |
| WO | 2012/024657 A1 | 2/2012 |
| WO | 2012/024658 A2 | 2/2012 |
| WO | 2012/027175 A2 | 3/2012 |
| WO | 2012/136333 A2 | 10/2012 |
| WO | 2013/028643 A1 | 2/2013 |
| WO | 2013/049071 A1 | 4/2013 |
| WO | 2013/059750 A1 | 4/2013 |
| WO | 2013/130910 A1 | 9/2013 |
| WO | 2014/014587 A2 | 1/2014 |
| WO | 2014/055936 A1 | 4/2014 |
| WO | 2015/073399 A1 | 5/2015 |
| WO | 2015/073999 A1 | 5/2015 |
| WO | 2015/078998 A1 | 6/2015 |
| WO | 2015/134925 A1 | 9/2015 |
| WO | 2015/179098 A1 | 11/2015 |
| WO | 2016/176671 A2 | 11/2016 |
| WO | 2017/053462 A1 | 3/2017 |
| WO | 2017/059356 A1 | 4/2017 |
| WO | 2017/069856 A1 | 4/2017 |

OTHER PUBLICATIONS

Anderson, et al. A miniature integrated device for automated multistep genetic assays. Nucleic Acids Research. 2000;28:e60.

Armani, et al. Re-configurable fluid circuits by PDMS elastomer micromachining. Proceedings of IEEE Micro Electro Mechanical Systems: MEMS. 1999; 222-227.

Au et al., Microvalves and Micropumps for BioMEMS, Micromachines 2011, 2(2), 179-220, May 24, 2011.

Bennett, et al. Toward the 1,000 dollars human genome. Pharmacogenomics, 6 (4) 373-382. (Jun. 2005).

Bings, et al. Microfluidic Devices Connected to Fused-Silica Capillaries with Minimal Dead Dead Volume. Analytical Chemistry. 1999;71(15):3292-3296.

Blazej, et al. Microfabricated bioprocessor for integrated nanoliter-scale Sanger DNA sequencing. Proc. Natl. Acad. Sci. USA 2006;103:7240-7245.

Blazej, et al. Polymorphism Ratio Sequencing: A New Approach for Single Nucleotide Polymorphism Discovery and Genotyping. Genome Research. 2003; 13:287-293.

(56) References Cited

OTHER PUBLICATIONS

Branton, et al. The potential and challenges of nanopore sequencing. Nat Biotechnol. Oct. 2008;26(10):1146-53. doi: 10.1038/nbt.1495.
Brenner, et al. Gene expression analysis by massively parallel signature sequencing (MPSS) on microbead arrays. Nature Biotechnology, 18: 630-634 (2000).
Buchholz, et al. The use of light scattering for precise characterization of polymers for DNA sequencing by capillary electrophoresis. Electrophoresis. 2001;22:4118-4128.
CAPLUS abstract of Krohkin et al. Modified silica as a stationary phase for ion chromatography. Journal of Chromatography A. 1995;706:93-8.
Chan, et al. Microfabricated Polymer Devices for Automated Sample Delivery of Peptides for Analysis by Electrospray Ionization Tandem Mass Spectrometry. Analytical Chemistry. 1999;71(20):4437-4444.
Chiem, et al. Microchip systems for immunoassay: an integrated immunoreactor with electrophoretic separation for serum theophylline determination. Clinical Chemistry. 1998;44(3):591-598.
Chiem, et al. Room temperature bonding of micromachined glass devices for capillary electrophoresis. Sensors and Actuators. 2000;B63(3):147-152.
Chinese office action dated Jan. 31, 2011 for CN 200580035911.7. (In Chinese with English translation).
Chinese office action dated Jul. 8, 2011 for CN 200580035911.7. (In Chinese with English translation).
CN First Office Action issued in Application No. 201480071855.1, dated Apr. 20, 2017.
CN Search Report issued in Application No. 201480071855.1, dated Apr. 12, 2017.
CN Second Office Action issued in Application No. 201480071855.1, dated Feb. 11.
CN Supplemental Search Report issued in Application No. 201480071855.1, dated Feb. 4, 2018.
CN Third Office Action issued in Application No. 201480071855.1, Global Dossier dated Aug. 13, 2018.
Co-pending U.S. Appl. No. 14/659,108, filed Mar. 16, 2015.
Co-pending U.S. Appl. No. 14/824,333, filed Aug. 12, 2015.
Co-pending U.S. Appl. No. 14/919,620, filed Oct. 21, 2015.
Co-pending U.S. Appl. No. 15/037,039, filed May 16, 2016.
Co-pending U.S. Appl. No. 15/154,086, filed May 13, 2016.
Co-pending U.S. Appl. No. 15/342,914, filed Nov. 3, 2016.
Co-pending U.S. Appl. No. 15/117,053, filed Aug. 5, 2016.
Coleman, et al. A sequential injection microfluidic mixing strategy. Microfluidics and Nanofluidics. 2005;319-327.
Curcio, et al. Continuous Segmented-Flow Polymerase Chain Reaction for High-Throughput Miniaturized DNA Amplification. Analytical Chemistry. 2003;75(1):1-7.
Datasheet Cycle Sequencing, Retrieved from the internet, URL:http//answers.com/topic/cyclesequencing. Printed Sep. 3, 2010, pp. 1-2.
Diehl et al. Beaming: single-molecule PCR on microparticles in water-in-oil emulsions. Nature Methods 3(7):551-559 (2006).
Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.
Doherty, et al. Sparsely cross-linked "nanogels" for microchannel DNA sequencing. Electrophoresis. 2003;24(24):4170-4180.
Dorfman, et al. Contamination-Free Continuous Flow Microfluidic Polymerase Chain Reaction for Quantitative and Clinical Applications. Analytical Chemistry. 2005;77(11):3700-3704.
Doyle, et al. Self-Assembled Magnetic Matrices for DNA Separation Chips. Science. 2000;295:2237.
Dressman, et al. Transforming single DNA molecules into fluorescent magnetic particles for detection and enumeration of genetic variations. Proc Natl Acad Sci USA. 2003;100(15):8817-8822.
Eid, et al. Real-time DNA sequencing from single polymerase molecules. Science. Jan. 2, 2009;323(5910):133-8. doi: 10.1126/science.1162986. Epub Nov. 20, 2008.
Emrich, et al. Microfabricated 384-Lane Capillary Array Electrophoresis Bioanalyzer for Ultrahigh-Throughput Genetic Analysis. Analytical Chemistry. 2002;74(19):5076-5083.
EP Search Report and Written Opinion issued in Application No. EP14861199, dated Oct. 18, 2017.
Ericson, et al. Electroosmosis- and Pressure-Driven Chromatography in Chips Using Continuous Beds. Analytical Chemistry. 2000;72(1):81-87.
Erratum for Margulies, et al. Genome sequencing in microfabricated high-density picolitre reactors. Nature. 2005;437(7057):376-80.
European search report and search opinion dated Aug. 17, 2011 for Application No. 08799648.4.
European search report and search opinion dated Jun. 22, 2016 for EP Application No. 11818879.6.
Office action dates Dec. 7, 2012 for U.S. Appl. No. 13/590,051.
Office action dates Feb. 27, 2013 for U.S. Appl. No. 13/590,965.
Office action dates Jan. 15, 2014 for U.S. Appl. No. 12/321,594.
Office action dates Sep. 19, 2012 for U.S. Appl. No. 12/321,594.
Office Action Final dated Feb. 6, 2008 issued in U.S. Appl. No. 11/139,018.
Office Action issued in U.S. Appl. No. 15/117,053, dated May 7, 2018.
Office Action issued in U.S. Appl. No. 15/173,894, dated Jan. 23, 2018.
Office Action mailed Apr. 27, 2007 in U.S. Appl. No. 11/139,018.
Office Action mailed Jul. 12, 2007 in U.S. Appl. No. 10/750,533.
Oh, et al. A review of microvalves. J. Micromech. Microeng. 2006; 16:R13-R39.
Ohori, et al. Partly disposable three-way mirovalve for a medical micro total analysis system (muTAS). Sensors and Actuators. 1998;A64(1): 57-62.
Oleschuk, et al. Trapping of Bead-Based Reagents within Microfluidic Systems: On-Chip Solid-Phase Extraction and Electrochromatography. Analytical Chemistry. 2000;72:585-590.
Olsen, et al. Immobilization of DNA Hydrogel Plugs in Microfluidic Channels. Analytical Chemistry. 2002;74:1436-1441.
Paegel, et al. High-throughput DNA sequencing with a 96-lane capillary array electrophoresis bioprocessor. Proc Natl Acad Sci USA. 2002;99:574-579.
Paegel, et al. Microchip Bioprocessor for Integrated Nanovolume Sample Purification and DNA Sequencing. Analytical Chemistry. 2002;74(19):5092-5098.
Paegel, et al. Microfluidic devices for DNA sequencing: sample preparation and electrophoretic analysis. Current Opinion in Biotechnology. 2003;14(1):42-50.
Paegel, et al. Turn Geometry for Minimizing Band Broadening in Microfabricated Capillary Electrophoresis Channels. Analytical Chemistry. 2000;72:3030-3037.
PCT Notification of Transmittal of the International Search Report and The Written Opinion of the International Searching Authority, or the Declaration, dated Jun. 17, 2008, Application No. PCT/US2007/082568.
Peoples, et al. Microfluidic Immunoaffinity Separations for Bioanalysis. J. Chromat. B. 2008;866:14-25 (available online Aug. 30, 2007).
Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.
Ramsey, et al. Generating Electrospray from Microchip Devices Using Electroosmotic Pumping. Analytical Chemistry. 1997;69(6):1174-1178.
Reissue U.S. Appl. No. 90/011,453, filed Jan. 21, 2011.
Rohr, et al. Porous polymer monoliths: Simple and efficient mixers prepared by direct polymerization in the channels of microfluidic chips. Electrophoresis. 2001;22:3959-3967.
Rye, et al. High-sensitivity two-color detection of double-stranded DNA with a confocal fluorescence gel scanner using ethidium homodimer and thiazole orange. Nucleic Acids Research. 1991;19(2):327-333.
Scherer, et al. High-Pressure Gel Loader for Capillary Array Electrophoresis Microchannel Plates. Biotechniques. 2001;31(5):1150-1154.

(56) References Cited

OTHER PUBLICATIONS

Schomburg, et al. Design Optimization of Bistable Microdiaphragm Valves. Sensors and Actuators. 1998;A64:259-264.
Seifar, et al. Capillary electrochromatography with 1.8-mum ODS-modified porous silica particles. Journal of Chromatography. 1998; A808:71-77.
Shaikh, et al. A modular microfluidic architecture for integrated biochemical analysis. Proc Natl Acad Sci U S A. Jul. 12, 2005;102(28):9745-50. Epub Jun. 28, 2005.
Shendure, et al. Next-generation DNA sequencing. Nat Biotechnol. Oct. 2008;26(10):1135-45. doi: 10.1038/nbt1486.
Simpson, et al. High-throughput genetic analysis using microfabricated 96-sample capillary array electrophoresis microplates. Proc Natl Acad Sci USA. 1998;95:2256-2261.
Simpson, et al. Microfabrication Technology for the Production of Capillary Array Electrophoresis Chips. Biomedical Microdevices. 1998;1:7-26.
Soper, et al. Sanger DNA Sequencing Reactions Performed in a Solid-Phase Nanoreactor Directly Coupled to Capillary Gel Electrophoresis. Analytical Chemistry. 1998;70:4036-4043.
Spiering, et al. Novel microstructures and technologies applied in chemical analysis techniques. 1997 International Conference on Solid-State Sensors and Actuators. 1997;1:511-514.
Stevens, et al. Bacterial Separation and Concentration from Complex Sample Matrices: a Review. Crit. Rev. Microbiol. 2004;30(1):7-24.
Takao, et al. A Pneumatically Actuated Full In-Channel Microvalve With MOSFET-Like Function in Fluid Channel Networks. Journal of Microelectromechanical Systems. 2002;11(5):421-426.
Takao, et al. Microfluidic Integrated Circuits for Signal Processing Using Analogous Relationship Betweeen Pneumatic Microvalve and MOSFET. Journal of Microelectromechanical Systems. 2003;12(4):497-505.
Tanaka et al., An active valve incorporated into a microship using a high strain electroactive polymer, Sensors and Actuators B 184 (2013) 163-169, Apr. 20, 2013.
Thomas, et al. Application of Genomics to Toxicology Research. Environmental Health Perspectives. 2002;110(6):919-923.
Tice, et al. Formation of Droplets and Mixing in Multiphase Microfluidics at Low Values of the Reynolds and the Capillary Numbers. Langmuir. 2003;19:9127-9133.
Todd Thorsen, et al., "Microfluidic Large-Scale Integration", www.sciencemag.org, Science, vol. 298, Oct. 18, 2002, pp. 580-584.
U.S. Appl. No. 10/540,658 Office Action Final dated Feb. 19, 2008.
U.S. Appl. No. 14/032,173, filed Sep. 10, 2013.
U.S. Appl. No. 14/474,047, filed Aug. 29, 2014.
U.S. Appl. No. 61/709,417, filed Oct. 4, 2012.
Unger, et al. Monolithic microfabricated valves and pumps by multilayer soft lithography. Science. Apr. 7, 2000;288(5463):113-6.
Van Der Moolen, et al. A Micromachined Injection Device for CZE: Application to Correlation CZE. Analytical Chemistry. 1997;69(20):4220-4225.
Van Der Moolen, et al. Correlation Capillary Zone Electrophoresis, a Novel Technique to Decrease Detection Limits. Chromatographia. 1995;40(7/8):368-374.
Van Ness, et al. Isothermal Reactions for the Amplification of Oligonucleotides. Proc. Nat. Acad. Sci. USA. 2003;100(8):4504-4509.
Vazquez, et al. Electrophoretic Injection within Microdevices. Analytical Chemistry. 2002;74:1952-1961.
Notice of allowance dated Dec. 7, 2012 for U.S. Appl. No. 12/795,515.
Notice of allowance dated Feb. 19, 2013 for U.S. Appl. No. 12/845,650.
Notice of allowance dated Jan. 31, 2017 for U.S. Appl. No. 14/552,389.
Notice of allowance dated Jul. 8, 2013 for U.S. Appl. No. 13/717,585.
Notice of allowance dated Jun. 12, 2017 for U.S. Appl. No. 14/804,675.
Notice of allowance dated Jun. 22, 2017 for U.S. Appl. No. 14/824,333.
Notice of allowance dated Jun. 25, 2014 for U.S. Appl. No. 13/656,503.
Notice of allowance dated Jun. 9, 2011 for U.S. Appl. No. 12/831,949.
Notice of allowance dated Jun. 9, 2017 for U.S. Appl. No. 14/824,333.
Notice of allowance dated May 3, 2010 for U.S. Appl. No. 11/670,866.
Notice of allowance dated May 5, 2015 for U.S. Appl. No. 13/202,884.
Notice of allowance dated Nov. 12, 2014 for U.S. Appl. No. 13/967,957.
Notice of allowance dated Nov. 22, 2013 for U.S. Appl. No. 13/590,965.
Obeid, et al. Microfabricated Device for DNA and RNA Amplification by Continuous-Flow Polymerase Chain Reaction and Reverse Transcription-Polymerase Chain Reaction with Cycle No. Selection. Analytical Chemistry. 2003;75(2):288-295.
Ocvirk, et al. High Performance Liquid Chromatography Partially Integrated onto a Silicon Chip. Analytical Methods and Instrumentation. 1995;2:74-82.
Ocvirk, et al. Optimization of confocal epifluorescence microscopy for microchip-based miniaturized total analysis systems. The Analyst. 1998;123:1429-1434.
Office action dated Apr. 1, 2014 for U.S. Appl. No. 13/202,884.
Office action dated Jul. 1, 2016 for U.S. Appl. No. 14/253,622.
Office action dated Aug. 9, 2016 for U.S. Appl. No. 14/500,846.
Office action dated Sep. 15, 2014 for U.S. Appl. No. 13/886,068.
Office action dated Oct. 29, 2013 for U.S. Appl. No. 13/202,884.
Office action dated Apr. 15, 2015 for U.S. Appl. No. 13/896,581.
Office Action dated Apr. 27, 2007 in U.S. Appl. No. 11/139,018.
Office action dated Aug. 23, 2012 for U.S. Appl. No. 13/287,398.
Office action dated Aug. 24, 2012 for U.S. Appl. No. 12/026,510.
Office action dated Aug. 29, 2012 for U.S. Appl. No. 12/605,217.
Office action dated Dec. 29, 2016 for U.S. Appl. No. 14/824,333.
Office action dated Dec. 7, 2012 for U.S. Appl. No. 13/590,051.
Office action dated Feb. 14, 2017 for U.S. Appl. No. 14/804,675.
Office action dated Feb. 28, 2013 for U.S. Appl. No. 13/113,968.
Office action dated Jan. 13, 2017 for U.S. Appl. No. 14/253,622.
Office action dated Jan. 17, 2014 for U.S. Appl. No. 13/656,503.
Office action dated Jan. 22, 2013 for U.S. Appl. No. 12/845,650.
Office Action dated Jul. 12, 2007 in U.S. Appl. No. 10/750,533.
Office Action dated Jul. 2, 2007 in U.S. Appl. No. 10/540,658.
Office action dated Jul. 26, 2012 for U.S. Appl. No. 12/845,650.
Office action dated Mar. 19, 2009 for U.S. Appl. No. 11/670,866.
Office action dated Mar. 24, 2010 for U.S. Appl. No. 11/670,866.
Office action dated Mar. 24, 2015 for U.S. Appl. No. 13/202,884.
Office action dated Mar. 30, 2012 for U.S. Appl. No. 12/795,515.
Office action dated May 22, 2012 for U.S. Appl. No. 12/526,015.
Office action dated May 30, 2014 for U.S. Appl. No. 13/656,503.
Office action dated Nov. 14, 2012 for U.S. Appl. No. 12/526,015.
Office action dated Sep. 11, 2014 for U.S. Appl. No. 13/967,957.
European search report and search opinion dated Jun. 6, 2011 for Application No. 10011511.2.
European search report and search opinion dated Sep. 11, 2013 for EP Application No. 10784213.
European search report dated Dec. 18, 2009 for Application No. 03808583.3.
European search report dated Jul. 13, 2016 for EP Application No. 09714332.5.
European search report dated Oct. 29, 2012 for EP Application No. 07853470.8.
European search report dated Sep. 1, 2010 for Application No. 5804847.1.
European search report with written opinion dated Jul. 12, 2017 for EP14861199.
Ewing, et al. Base-Calling of Automated Sequencer Traces Using Phred. I. Accuracy Assessment. Genome Research. 1998;8:175-185.
Ewing, et al. Base-Calling of Automated Sequencer Traces Using Phred. II. Error probabilities. Genome Research. 1998;8:186-194.
Extended European Search Report dated Apr. 6, 2018, issued in EP Application No. 15851818.3.
Figeys, et al. A Microfabricated Device for Rapid Protein Identification by Microelectrospray Ion Trap Mass Spectrometry. Analytical Chemistry. 1997;69(16):3153-3160.

(56) References Cited

OTHER PUBLICATIONS

Figeys, et al. An Integrated Microfluidics-Tandem Mass Spectrometry System for Automated Protein Analysis. Analytical Chemistry. 1998;70(18):3728-3734.
Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998; 12:1435-1444.
Figeys, et al. Nanoflow Solvent Gradient Delivery from a Microfabricated Device for Protein Identifications by Electrospray Ionization Mass Spectrometry. Analytical Chemistry. 1998;70(18):3721-3727.
First Examination Report dated Oct. 9, 2018, issued in Application No. 14861199.9.
Francis, et al. Flow analysis based on a pulsed flow of solution: theory, instrumentation and applications. Talanta. 2002;58(6):1029-1042.
Fuentes, et al. Detecting minimal traces of DNA using DNA covalently attached to superparamagnetic nanoparticles and direct PCR-ELISA. Biosens Bioelectron. Feb. 15, 2006;21(8):1574-80. Epub Aug. 29, 2005.
Fuller, et al. The challenges of sequencing by synthesis. Nat Biotechnol. Nov. 2009;27(11):1013-23. doi: 10.1038/nbt. 1585. Epub Nov. 6, 2009. Ghadessy, et al. Directed evolution of polymerase function by compartmentalized selfreplication. Proc Natl Acad Sci USA. 2001 ;98:4552-4557.
Fuller, et al. The challenges of sequencing by synthesis. Nat Biotechnol. Nov. 2009;27(11):1013-23. doi: 10.1038/nbt.1585. Epub Nov. 6, 2009.
Ghadessy, et al. Directed evolution of polymerase function by compartmentalized self-replication. Proc Natl Acad Sci USA. 2001;98:4552-4557.
Giddings, et al. A software system for data analysis in automated DNA sequencing. Genome Research. 1998;8:644-665.
Goll, et al. Microvalves with bistable buckled polymer diaphragms. Journal of Micromechanics and Microengineering. 1996;6:77-79.
Grodzinski, et al. Microfluidic System Integration in Sample Preparation Chip-Sets—a Summary. Conf. Proc. IEEE Eng. Med. Biol. Soc. 2004;4:2615-2618.
Grover, et al. An integrated microfluidic processor for single nucleotide polymorphism-based DNA computing. Lab on a Chip. 2005;5(10):1033-1040.
Grover, et al. Development and multiplexed control of latching pneumatic valves using microfluidic logical structures. Lab on a chip. 2006;6:623-631.
Grover, et al. Monolithic membrane valves and diaphragm pumps for practical large-scale integration into glass microfluidic devices. Sensors and Actuators. 2003;689:315-323.
Grover, et al. Practical Valves and Pumps for Large-Scale Integration into Microfludic Analysis Devices. Micro Total Analysis Systems. 2002;1:136-138.
Hansen, et al. A robust and scalable microfluidic metering method that allows protein crystal growth by free interface diffusion. Proc Natl Acad Sci USA. 2002;99(26):16531-16536.
Harrison, et al. Micromachining a Miniaturized Capillary Electrophoresis-Based Chemical Analysis System on a Chip. Science. 1993;261(5123):895-897.
Hayes, et al. Edge: A Centralized Resource for the Comparison, Analysis, and Distribution of Toxicogenomic Information. Molecular Pharmacology. 2005;67(4):1360-1368.
Heath, et al. PCR primed with VNTR core sequences yields species specific patterns and hypervariable probes. Nucleic Acids Res. Dec. 11, 1993;21(24):5782-5.
Holland, et al. Point-of-care molecular diagnostic systems—past, present and future. Curr Opin Microbiol. Oct. 2005;8(5):504-9.
Hultman, et al. Bidirectional Solid-Phase Sequencing of In Vitro-Amplified Plasmid DNA. BioTechniques. 1991;10(1):84-93.
International Preliminary Report for corresponding PCT Application No. PCT/CA2000/001421 dated Feb. 14, 2002.
International Preliminary Report for corresponding PCT Application No. PCT/US2005/018678 dated Nov. 13, 2007.
International Preliminary Report for corresponding PCT Application No. PCT/US2005/033347 dated Mar. 20, 2007.
International Preliminary Report for corresponding PCT Application No. PCT/US2007/002721 dated Aug. 5, 2008.
International Preliminary Report for corresponding PCT Application No. PCT/US2007/007381 dated Sep. 23, 2008.
International Preliminary Report for corresponding PCT Application No. PCT/US2007/061573 dated Aug. 26, 2008.
International Preliminary Report of Patentability issued in Application No. PCT/US15/28510 dated Dec. 1, 2016.
International Preliminary Report of Patentability issued in Application No. PCT/US2016/037711 dated Dec. 19, 2017.
International Preliminary Report on Patentability, issued in PCT Application No. PCT/US14/66008, dated May 24, 2016.
International search report and written opinion dated Apr. 30, 2012 for PCT/US2012/021217.
International search report and written opinion dated Jan. 29, 2016 for PCT Application No. PCT/US2015/056764.
International search report and written opinion dated Jan. 5, 2012 for PCT Application No. PCT/US2011/048527.
International search report and written opinion dated Jul. 22, 2013 for PCT Application No. PCT/US2013/028462.
International search report and written opinion dated Jun. 9, 2011 for PCT Application No. PCT/US2011/030973.
International search report and written opinion dated Mar. 24, 2011 for PCT Application No. PCT/US2010/058227.
International search report and written opinion dated Mar. 3, 2015 for PCT Application No. PCT/US2014/066008.
International search report and written opinion dated Mar. 8, 2013 for PCT/US2012/061223.
Veenstra, et al. The design of an in-plane compliance structure for microfluidical systems. Sensors and Actuators. 2002;681:377-383.
Waller, et al. Quantitative Immunocapture PCR Assay for Detection of Campylobacter jejuni in Foods. Applied Environmental Microbiology. 2000; 66(9):4115-4118.
Weimer, et al. Solid-Phase Capture of Proteins, Spores, and Bacteria. Applied Environmental Microbiology. 2001;67(3):1300-1307.
Wen, et al. Microfabricated isoelectric focusing device for direct electrospray ionization-mass spectrometry. Electrophoresis. 2000;21:191-197.
Wikipedia brochure for defining stocahstic process. Sep. 2, 2009.
Williams, et al. Amplification of complex gene libraries by emulsion PCR. Nature Methods. 2006;3(7):545-50.
Woolley, et al. Functional Integration of PCR Amplification and Capillary Electrophoresis in a Microfabricated DNA Analysis Device. Analytical Chemistry. 1996;68(23):4081-4086.
Wright, et al. Behavior and Use of Nonaqueous Media without Supporting Electrolyte in Capillary Electrophoresis and Capillary Electrochromatography. Analytical Chemistry. 1997;69(16):3251-3259.
Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.
Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.
Xue, et al. Multichannel Microchip Electrospray Mass Spectrometry. Analytical Chemistry. 1997;69(3):426-430.
Yang, et al. A MEMS thermopneumatic silicone rubber membrane valve. Sensors and Actuators. 1998;A64(1):101-108.
Yu, et al. Preparation of Monolithic Polymers with Controlled Porous Properties for Microfluidic Chip Applications Using Photoinitiated Free Radial Polymerization. Journal of Polymer Science. 2002;40:755-769.
Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.

(56) References Cited

OTHER PUBLICATIONS

Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.
Zhang, et al. Microfabricated Devices for Capillary Electrophoresis-Electrospray Mass Spectrometry. Analytical Chemistry. 1999;71(15):3258-3264.
International search report and written opinion dated Oct. 26, 2011 for PCT Application No. PCT/US11/38180.
International search report and written opinion dated Oct. 26, 2015 for PCT/US2015/028510.
International search report and written opinion dated Sep. 1, 2010 for PCT Application No. PCT/US2010/040490.
International Search Report and Written Opinion issued in Application No. PCT/US2016/037711 dated Sep. 16, 2016.
International Search Report and Written Opinion, issued in PCT Application No. PCT/US14/66008, dated Mar. 3, 2015.
International search report dated Apr. 5, 2001 for PCT Application No. PCT/CA2000/001421.
International search report dated Aug. 18, 2009 for PCT Application No. PCT/US09/00419.
International search report dated Aug. 23, 2006 for PCT Application No. PCT/US2005/033347.
International search report dated Aug. 26, 2004 PCT Application No. PCT/US2003/041466.
International search report dated Jul. 11, 2008 for PCT Application No. PCT/US07/61573.
International search report dated Jul. 30, 2010 for PCT Application No. PCT/US2010/036464.
International search report dated May 14, 2010 for PCT Application No. PCT/US2009/006640.
International search report dated Oct. 6, 2010 for PCT Application No. PCT/US10/37545.
International search report dated Sep. 25, 2007 for PCT Application No. PCT/US2007/002721.
International written opinion dated Oct. 6, 2010 for PCT Application No. PCT/US10/37545.
International written opinion report dated Jul. 30, 2010 for PCT Application No. PCT/US2010/036464.
Jacobson, et al. Electrokinetic Focusing in Microfabricated Channel Structures. Anal. Chem., 1997, 69 (16), pp. 3212-3217.
Japanese Office Action dated Apr. 27, 2010 for Application No. JP2001-540363 (in Japanese with English translation).
Japanese Office Action dated Dec. 21, 2010 for Application No. JP2001-540363 (in Japanese with English translation).
Japanese office action dated Jul. 28, 2011 for Application No. 2008-553535 (in Japanese with English translation).
Japanese office action dated May 11, 2012 for Application No. 2008-553535 (English translation).
Japanese office action dated May 27, 2011 for Application No. 2007-532553 (in Japanese with English translation).
Ju, et al. Fluorescence energy transfer dye-labeled primers for DNA sequencing and analysis. Proc. Natl. Acad. Sci. USA. 1995;92:4347-4351.
Kan, et al. A novel thermogelling matrix for microchannel DNA sequencing based on poly-N-alkoxyalkylaclylamide copolymers. Electrophoresis. 2003;24(24):4161-4169.
Koh, et al. Integrating Polymerase Chain Reaction, Valving, and Electrophoresis in a Plastic Device for Bacterial Detection. Analytical Chemistry. 2003;75(17):4591-4598.
Kopp, et al. Chemical Amplification Continuous-Flow PCR on a Chip. Science. 1998;280:1046-1048.
Krsek, et al. Comparison of different methods for the isolation and purification of total community DNA from soil. Journal of Microbiological Methods 39.1 (1999): 1-16.
Lagally, et al. Fully integrated PCR-capillary electrophoresis microsystem for DNA analysis. Lab on a Chip. 2001;1(2):102-107.
Lagally, et al. Integrated Portable Genetic Analysis Microsystem for Pathogen/Infectious Disease Detection. Analytical Chemistry. 2004;76:3162-3170.
Lagally, et al. Monolithic integrated microfluidic DNA amplification and capillary electrophoresis analysis system. Sensors and Actuators. 2000;663(3)138-146.
Lagally, et al. Single-Molecule DNA Amplification and Analysis in an Integrated Microfluidic Device. Analytical Chemistry. 2001;73(3): 565-570.
Lai et al., Design and dynamic characterization of "single-stroke" peristaltic PDMS micropumps, Lab Chip. Jan. 21, 2011; 11(2): 336-342, Published online Oct. 19, 2010.
Lazar, et al. Subattomole-Sensitivity Microchip Nanoelectrospray Source with Time-of-Flight Mass Spectrometry Detection. Analytical Chemistry. 1999;71(17):3627-3631.
Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.
Li, et al. Rapid and sensitive separation of trace level protein digests using microfabricated devices coupled to a quadrupole-time-of-flight mass spectrometer. Electrophoresis. 2000;21:198-210.
Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.
Licklider, et al. A Micromachined Chip-Based Electrospray Source for Mass Spectrometry. Analytical Chemistry. 2000;72(2):367-375.
Lisec, et al. A bistable pneumatic microswitch for driving fluidic components. Sensors and Actuators. 1996;A54:746-749.
Liu, et al. Automated parallel DNA sequencing on multiple channel microchips. Proc. Natl. Acad. Sci. USA. 2000;97(10):5369-5374.
Liu, et al. Optimization of High-Speed DNA Sequencing on Microfabricated Capillary Electrophoresis Channels. Analytical Chemistry. 1999;71:566-573.
Lund-Olesen, et al. Capture of DNA in microfluidic channel using magnetic beads: Increasing capture efficiency with integrated microfluidic mixer. Journal of Magnetism and Magnetic Materials 311 (2007): 396-400.
Mamanova, et al. FRT-seq: amplification-free, strand-specific transcriptome sequencing. Nat Methods. Feb. 2010;7(2):130-2. doi: 10.1038/nmeth.1417. Epub Jan. 17, 2010.
Melin, et al. A Passive 2-Dimensional Liquid Sample Micromixer. 7th International Conference on Miniaturized Chemical and Biochemical Analysis Systems. 2003;167-170.
Metzker, M. Sequencing technologies—the next generation. Nat Rev Genet. Jan. 2010;11(1):31-46. doi: 10.1038/nrg2626. Epub Dec. 8, 2009.
MillGat pump user manual, version 2.12, published 2005, pp. 1-28.
Mitra, et al. Digital genotyping and haplotyping with polymerase colonies. Proc Natl Acad Sci USA. 2003.100(10):15926-5931.
Norris, et al. Fully-integrated, multiplexed STR-based human identification using a single microfluidic chip and automated instrument. Available at http://www.promega.com/geneticidproc/ussymp20proc/oralpresentations/lande-rsbienvenue.pdf. Accessed Jun. 2, 2010.
Notice of allowance dated Apr. 25, 2013 for U.S. Appl. No. 12/815,685.
Extended European Search Report dated Aug. 16, 2018 issued in Application No. EP 16787296.9 [ITGXP002EP].
Figarelli, Vince, "The Arizona DPS Rapid DNA Program," [Slides] Aug. 31, 2014, XP055497564, pp. 1-46. [retrieved on Aug. 6, 2018] <URL:https://integenx.comjwp-contentjuploadsj2014/08/Figarelli-ASCLD-Rapid-DNA_2014.pdf>.
Integenx, [Internet Article] "Announces First State-Wide deployment of the RapidHIT System with SmallPond(Trademark) at Arizona Department of Public Safety" Cases, Press Release, May 14, 2014. [retrieved on Aug. 6, 2018] <URL:https://integenx.comjintegenx-announce s-first-state-wide-deployment-of-the- rapid hit-system-with-smallpond-at-arizona-department-of-public-safety/> figures 1-3.
International Preliminary Report on Patentability dated Apr. 12, 2018 issued in Application No. PCT/US2016/054994 [ITGXP004WO].

(56) References Cited

OTHER PUBLICATIONS

International Preliminary Report on Patentability dated Apr. 5, 2018 issued in Application No. PCT/US2016/052930 [ITGXP003WO].
International Preliminary Report on Patentability dated May 3, 2018 issued in Application No. PCT/US2016/050003 [ITGXPO01WOC1 ].
International Preliminary Report on Patentability dated Nov. 9, 2017 issued in Application No. PCT/US2016/030331 [ITGXP002WO].
International Search Report and Written Opinion dated Jan. 12, 2017 issued in Application No. PCT/US16/50003 [ITGXPO01WOC1 ].
International Search Report and Written Opinion dated Jan. 19, 2017 issued in Application No. PCT/US16/54994 [ITGXP004WO].
International Search Report and Written Opinion dated Oct. 28, 2016 issued in Application No. PCT/US16/30331 [ITGXP002WO].
International Search Report dated Dec. 9, 2016 issued in Application No. PCT/US16/52930 [ITGXP003WO].
Wikipedia: "Extract, transform, load" [Internet Article] Apr. 25, 2015. XP055497574., pp. 1-10. [retrieved on Aug. 6, 2018] <URL:https:jjen.wikipedia.orgjwjindex.php?title=Extract.transform.load&oldid=659213002>.
Wikipedia: "Mobile Web," [Internet Article] Mar. 27, 2015, XP055497568, pp. 1-5. [retrieved on Aug. 6, 2018] <URL:https:jjen.wikipedia.orgjwjindex.php?title=Mobile Web&oldid=653815098>.
Wikipedia: "Unified communications," [Internet Article] Apr. 16, 2015, XP055497572., pp. 1-5. [retrieved on Aug. 6, 2018] <URL:https:jjen.wikipedia.orgjwjindex.php?title=Unified communications&oldid=656726520>.

* cited by examiner

FIG. 17

| Step # | chemistry steps | Cycler out (A0) | Lysis (A1) | Lysis (A2) | Waste Shut off (A3) | Waste in (A4) | Cycler in (B0) | Lysis Transfer (B1) | Product Bottom (B2) | Product Top (B3) | Vent (B4) |
|---|---|---|---|---|---|---|---|---|---|---|---|
| 1 | Load SC | o | o | o | o | o | o | o | o | o | o |
| 2 | Prime lysis to waste* | c | o | o | o | c | o | o | o | c | o |
| 3 | Dispense lysis to lysis chamber | o | o | o | c | o | o | c | o | c | o |
| 4 | Mix lysis with air | o | o | o | o | o | o | o | o | c | o |
| 5 | Mix and heat lysis | o | c | o | c | o | c | o | c | c | o |
| 6 | Pull lysate to waste via RC | o | c | c | o | c | c | o | c | o | c |
| 7 | Push PMx and MMx to RC | c | c | o | o | o | o | o | o | o | o |
| 8 | Thermal cycling | c | c | c | c | c | c | c | c | c | o |
| 9 | Push ILS and product thru RC to Mix chamber | c | c | c | c | c | c | c | c | o | o |
| 10 | Push residual ILS and product to Mix chamber with air pump | o | c | c | o | c | o | c | c | o | o |
| 11 | Push product to cathode | o | c | c | c | o | o | c | o | o | o |
| 12 | Output to Cathode Water rinse of MC and product | o | c | c | c | c | o | c | c | o | o |
| 13 | Water rinse of MC and RC | o | c | o | c | o | o | c | o | o | o |
| 14 | Flush water out of SC to waste Chamber | o | o | o | c | o | o | c | c | o | o |
| 15 | Cathode Flush water from SC and line to Cathode | o | c | c | c | c | o | c | c | o | o |
| 16 | Release | o | o | o | o | o | o | o | o | o | o |

FLUIDIC CARTRIDGE WITH VALVE MECHANISM

CROSS-REFERENCE TO RELATED APPLICATIONS

This application is a continuation of U.S. application Ser. No. 17/181,228, filed Feb. 22, 2021, which is a divisional of U.S. application Ser. No. 16/250,646, filed Jan. 17, 2019 (now U.S. Pat. No. 10,961,561), which is a divisional of U.S. application Ser. No. 15/117,053, filed Aug. 5, 2016 (now U.S. Pat. No. 10,208,332), which is the National Stage Application filed under 35 USC § 371 of PCT Application No. PCT/US2015/028510, filed Apr. 30, 2015, which claims the benefit of and priority to: U.S. Provisional Application No. 62/069,752, filed Oct. 28, 2014 (now expired); U.S. Provisional Application No. 62/069,473, filed Oct. 28, 2014 (now expired); U.S. Provisional Application No. 62/067,429, filed Oct. 22, 2014 (now expired); U.S. Provisional Application No. 62/067,404, filed Oct. 22, 2014 (now expired); U.S. Provisional Application No. 62/067,120, filed Oct. 22, 2014 (now expired); and U.S. Provisional Application No. 62/001,533, filed May 21, 2014 (now expired). Each of the foregoing applications is incorporated herein by reference in its entirety and for all purposes.

STATEMENT AS TO FEDERALLY SPONSORED RESEARCH

None.

BACKGROUND OF THE INVENTION

Versions of systems including sample cartridges and fluidic systems for sample extraction and analysis are described in, for example, U.S. Pat. Nos. 6,190,616; 6,551,839; 6,870,185; 7,244,961; 8,394,642 and 8,431,340; US patent applications 2006/0073484; 2009/0253181; 2011/0039303; 2011/0126911; 2012/0181460; 2013/0139895 and 2013/0115607; and International Patent Applications PCT/US2013/130910 and PCT/EP2012/001413.

US patent publication 2003/0197139 refers to a valve for use in microfluidic structures.

US patent publication 2009/0314970 refers to a mechanically-actuated microfluidic pinch valve.

US patent publication 2013/0240140 refers to a process for producing a microfluidic apparatus and related laminating devices.

International publication WO 2012/136333 refers to a heat weldable film for labeling plastic polymeric reaction tubes.

U.S. Pat. No. 6,883,774 refers to a microvalve and method of forming a microvalve.

U.S. Pat. No. 7,318,912 refers to microfluidic systems and methods for combining discreet fluid volumes.

U.S. Pat. No. 8,313,941 refers to integrated microfluidic control employing programmable tactile actuators.

U.S. Pat. No. 8,501,305 refers to a laminate.

SUMMARY OF THE INVENTION

Disclosed herein is a cartridge comprising: (a) a body comprising a malleable material; and (b) a layer comprising a deformable material bonded to a surface of the body and sealing one or more fluidic channels that communicate with one or more valve bodies formed in a surface of the body; wherein: (i) the one or more valve bodies comprise: (A) a segment of the channel comprising a wall having a pair of ridges and a floor depressed into the surface; and (B) reliefs depressed into the surface and defining depressions that flank the ridges on two sides of the segment of the channel; and (iii) the layer is bonded to the surface of the body and to the ridges such that the one or more channels, channel segments and reliefs are sealed; and wherein a valve body sealed with the layer forms a valve closable by forcing the layer against the floor of the segment of the channel. In one embodiment the cartridge of comprises elements of a fluidic circuit including a fluid inlet, a fluid outlet and at least one compartment, which elements are fluidically connected through fluidic channels, wherein at least one fluidic channel comprises a valve body. In another embodiment the cartridge comprises at least one compartment selected from a reagent compartment, a sample compartment, a mixing compartment, a reaction compartment and a waste compartment. In another embodiment a fluid inlet or a fluid outlet comprises a via through the body. In another embodiment the cartridge comprises at least one sample compartment configured to accept a cotton tipped swab. In another embodiment the cartridge comprises at least one mixing chamber configured for bubbling of air through the mixing chamber. In another embodiment the cartridge comprises a reaction chamber comprising a solid substrate, e.g., solid phase extraction material, for retaining analyte from a sample. In another embodiment the cartridge comprises a pump configured as a depression in the surface. In another embodiment the solid substrate comprises a material that binds nucleic acid. In another embodiment the solid substrate comprises Whatman paper, a carboxylated particle, a sponge-like material, a polymer membrane, magnetically attractable particles, or glass particles. In another embodiment the solid substrate binds a predetermined amount of material. In another embodiment the cartridge comprises a reaction chamber comprising one or more thermally conductive walls and configured for thermal cycling. In another embodiment the cartridge comprises at least one waste compartment. In another embodiment the cartridge comprises a waste chamber, wherein the waste chamber comprises a material that degrades nucleic acid. In another embodiment the material that degrades nucleic acid comprises a hypochlorite salt. In another embodiment the cartridge further comprises guide vias through the body. In another embodiment the body further comprises a barrel comprising a plunger and in fluid communication with at least one of the fluidic channels. In another embodiment the body further comprises at least one reagent compartment comprising a reagent, wherein the compartment comprises an openable seal that, when opened, puts the compartment in fluidic communication through a via with a fluidic channel on the surface. In another embodiment the body further comprises one or more reagent compartments comprising reagents including nucleic acid primers, nucleotides and DNA polymerases sufficient to perform PCR. In another embodiment the reagents are sufficient for performing multiplex PCR on STR loci. In another embodiment the body further comprises a pump configured as a depression in the surface. In another embodiment the deformable material has a durometer value of between 10 Shore D to 80 Shore D. In another embodiment the deformable material comprises a heat seal material. In another embodiment the deformable material comprises a material selected from polypropylene, polyethylene, polystyrene, cycloolefin co-polymer (COC), mylar, polyacetate) and a metal. In another embodiment a portion of the layer of deformable material covering a valve seat does not comprise an elastomeric material, e.g., is not PDMS. In another embodiment the layer of deformable material has a higher yield strength than the malleable material. In another embodiment the deformable material is attached to the body through an adhesive. In another embodiment the deformable material is welded to the body. In another embodiment the cartridge comprises (i) a surface, (ii) one or more channels formed in the surface and elements of a fluidic circuit including a fluid inlet, a fluid outlet and at least three chambers, which elements are fluidically communicating connected through fluidic channels, wherein each fluidic channel connecting two of the chambers comprises a valve body. In another embodiment one of the chambers is configured as a lysis chamber configured to accept a biological sample, one of the chambers is configured as a mixing chamber configured to bubble air when liquid is contained in the mixing chamber, and one of the chambers is configured as a reaction chamber comprising one or more thermally conductive walls and configured for thermal cycling. In another embodiment the cartridge further comprises, at least one reagent compartment comprising reagents for performing PCR (e.g., PCR primers, nucleotides and a DNA polymerase), wherein the at least one reagent chamber comprises an openable seal that, when opened, puts the reagent chamber in fluidic communication with the reaction chamber. In another embodiment at least one reagent chamber comprises PCR primers selected to amplify a plurality of STR loci. In another embodiment one of the chambers is configured as a lysis chamber configured to accept a biological sample, one of the chambers is configured as an isolation chamber configured to receive magnetically responsive capture particles and to immobilize said particles when a magnetic force is applied to the isolation chamber, and one of the chambers is configured as a reaction chamber comprising one or more thermally conductive walls and configured for thermal cycling. In another embodiment the cartridge further comprises, at least two sets of reagent compartments, wherein a first set of reagent compartments comprises reagents for performing PCR, and wherein a second set of reagent compartments comprises reagents for performing cycle sequencing, wherein each reagent compartment comprises openable seal that, when opened, puts the reagent compartment in fluidic communication with the reaction chamber. In another embodiment the cartridge further comprises a reagent compartment comprising reagents to degrade PCR primers and nucleotide triphosphates. In another embodiment the cartridge further comprises at least two sets of reagent compartments, wherein both the first set of reagent compartments and the second set of reagent compartments comprise reagents for performing PCR, and wherein each reagent compartment comprises openable seal that, when opened, puts the reagent compartment in fluidic communication with the reaction chamber. In another embodiment the PCR reagents in one of the sets of reagent compartments comprises reagents for performing adapted for performing quantification of human DNA. In another embodiment the cartridge comprises a branched fluidic circuit comprising chambers connected by fluidic channels and comprising a common portion and a plurality of branches, wherein the common portion comprises a fluid inlet and a lysis chamber, and wherein each branch comprises at least one reaction chamber comprising one or more thermally conductive walls and configured for thermal cycling, at least one isolation chamber and a fluid outlet, wherein at least the fluidic channels connecting a reaction chamber with an isolation chamber comprises a valve body. In another embodiment the common portion comprises a common isolation chamber. In another embodiment each branch further comprises at least one reagent chamber reagent compartment comprising an openable seal that, when opened, puts the reagent compartment in fluidic communication with the reaction chamber in the branch. In another embodiment the cartridge comprises two branches, wherein a first branch comprises reagents to perform a forward cycle sequencing reaction on a target polynucleotide and a second branch comprises reagents to perform a reverse cycle sequencing reaction on a target polynucleotide.

Also disclosed herein is an article comprising: (a) a body comprising a malleable material and comprising: (i) a surface, (ii) one or more channels formed in the surface and fluidically communicating with one or more valve bodies, (iii) one or more valve bodies formed in the surface comprising: (A) a segment of the channel comprising a wall having a pair of ridges raised above the surface and a floor depressed into the surface; and (B) reliefs depressed into the surface and defining depressions that flank the ridges on two sides of the segment of the channel. In one embodiment the malleable material comprises a plastic, a wax or a soft metal. In another embodiment the malleable material comprises a thermoplastic, a thermoset, a single component resin or a multi-component resin. In another embodiment the malleable material comprises polypropylene, polystyrene, polyethylene, polyethylene terephthalate, polyester, polyamide, vinyl, poly(vinylchloride) (PVC), polycarbonate, polyurethane, polyvinyldiene chloride, cyclic olefin copolymer (COC), or any combination thereof. In another embodiment the body is injection molded or 3D printed. In another embodiment the surface is substantially defined in a plane. In another embodiment one or more of the channels has at least one aspect no greater than any of 1 mm, 2 mm, 3 mm, 4 mm or 5 mm. In another embodiment one or more of the channels comprises a wall having a pair of ridges raised above the surface and a floor depressed into the surface. In another embodiment the ridges have a height above the surface between about 50µ and about 300µ. In another embodiment the floor of the channel segment has a depth below the surface between about 50µ and about 300µ. In another embodiment the valve body has a substantially oblong shape. In another embodiment the channel segment comprises a force concentration zone. In another embodiment the channel segment comprises a textured floor (e.g., corrugated or dimpled). In another embodiment the reliefs have a depth below the surface of between 100µ and 300µ. In another embodiment the valve body has an area of no more than any of 100 mm$^2$, 50 mm$^2$, 25 mm$^2$, 20 mm$^2$, 15 mm$^2$ or 10 mm$^2$.

Also disclosed herein is a method of making an article comprising: (a) providing a body comprising a malleable material and comprising: (i) a surface, (ii) one or more channels formed in the surface and fluidically communicating with one or more valve bodies, (iii) one or more valve bodies formed in the surface comprising: (A) a segment of the channel comprising a wall having a pair of ridges raised above the surface and a floor depressed into the surface; and (B) reliefs depressed into the surface and defining depressions that flank the ridges on two sides of the segment of the channel; (b) providing a layer comprising a deformable material; and (c) bonding the layer to the surface and the ridges, wherein bonding seals the one or more channels, channel segments and reliefs. In one embodiment the body comprises a thermoplastic. In another embodiment the layer of deformable material comprises a heat seal. In another embodiment wherein bonding comprises applying heat and pressure to the heat seal against the body surface sufficient to weld a heat seal against the ridges and areas of the surface flanking the one or more channels and the reliefs. In another embodiment the pressure is applied with a heated die.

Also disclosed herein is a method of making an article comprising: (a) providing a body comprising a malleable material and comprising: (i) a surface, (ii) one or more channels formed in the surface and fluidically communicating with one or more valve bodies, (iii) one or more valve bodies formed in the surface comprising: (A) a segment of the channel comprising a wall having a pair of ridges and a floor depressed into the surface; and (B) reliefs depressed into the surface and defining depressions that flank the ridges on two sides of the segment of the channel; (b) providing a layer comprising a deformable material; and (c) bonding the layer to the surface and the ridges, wherein bonding seals the one or more channels, channel segments and reliefs. In one embodiment bonding comprises thermal bonding (e.g., heat sealing, welding, laser welding), chemical bonding (e.g., chemical bonding of oxide to PDMS, vapor bonding) or application of selectively placed adhesives.

Also disclosed herein is an instrument comprising a cartridge interface and a cartridge engaged with the cartridge interface, wherein: (I) the cartridge is a cartridge of this disclosure; (II) a cartridge interface comprising a plurality of rams, each ram positioned to actuate a valve and comprising a head having a widest dimension that is wider than a channel segment and less wide than the relief width, so that, when actuated toward the valve, the ram head presses the deformable material against the ridges and the floor, thereby closing the valve, but clearing the reliefs. In one embodiment the cartridge interface has a substantially planar face configured to mate with a substantially planar surface of the fluidic cartridge. In another embodiment the rams are retractable toward the interface and are spring biased toward the cartridge. In another embodiment the ram head has a length:width ratio of at least any of 2:1, 3:1, 4:1, 5:1, 6:1, 7:1, 8:1, 9:1 or 10:1. In another embodiment the ram head has an edge in its longest aspect that is substantially straight and either substantially flat or curved no more than a depth of a valve relief. In another embodiment at least one ram is comprised in a cam mechanism, wherein rotation of the cam actuates the ram toward or away from the valve. In another embodiment the cartridge interface further comprises a cover plate configured to receive the cartridge and comprising at least one plunger positioned to actuate at least one valve in cartridge. In another embodiment the cartridge interface further comprises a cover plate comprising a fluid inlet line that engages an inlet port on the cartridge and/or a fluid outlet line that engages an exit port on the cartridge. In another embodiment the sample cartridge is configured to receive one or more samples and to perform nucleic acid extraction and isolation, and DNA amplification when the cartridge is engaged with a cartridge interface. In another embodiment the instrument further comprises a sample analysis module in fluidic communication with a port in the cartridge interface that communicates with a reaction chamber of the engaged cartridge. In another embodiment the sample analysis module comprises an electrophoresis assembly comprising a capillary comprising a medium adapted for capillary electrophoresis and a cathode and anode configured to place a voltage across the capillary. In another embodiment the sample analysis module further comprises a detection assembly for detecting molecules in the capillary. In another embodiment the detection assembly comprises a laser and a detector for detecting laser light. In another embodiment the sample analysis module comprises a chromatograph, a DNA sequencer, an electrometer, an electrophoresis instrument, an ellipsometer, an interferometer, a mass spectrometer, an NMR spectrometer, a spectrometer a thermometer, a voltmeter. In another embodiment the instrument further comprises a source of magnetic force configured to exert a magnetic force against a chamber in the cartridge In another embodiment the instrument comprises an actuator, e.g., a plunger, configured to move one or more reagents from sealed compartments on the cartridge into fluidic channels of the cartridge.

Also disclosed herein is a method of controlling fluid flow in a fluid channel of fluidic cartridge comprising: (A) providing an instrument of this disclosure wherein at least one of the fluidic channels comprises a liquid; (B) closing a valve by actuating a ram head against the valve to force the deformable layer against the channel segment floor; (C) releasing the valve by retracting the ram head from the layer; and (D) moving the liquid through the valve by applying pressure to liquid in a fluidic channel, wherein fluid under pressure opens the valve. In one embodiment the method further comprises, after step (D): (E) re-closing the valve by actuating a ram head against the valve to force the deformable layer against the channel segment floor. In another embodiment the pressure is sourced through a pump internal to the cartridge or a pump external to the cartridge (e.g., a syringe) and delivered, optionally, through an inlet in the cartridge connected to a fluidic channel in the cartridge. In one embodiment a nearly incompressible fluid is moved through any fluidic channel in one direction only. In another embodiment no valve is closed and then opened before a liquid passes through the valve.

Also disclosed herein is a method of moving fluid in a fluid channel of fluidic cartridge comprising: (I) providing a fluidic cartridge comprising: (a) a body comprising a malleable material; and (b) a pump comprising a pump body defining a pump chamber and formed at least in part from a portion of the malleable material, wherein the pump chamber contains a liquid or a gas; (c) a fluidic channel internal to the cartridge and fluidically connected to the pump chamber, wherein the fluidic channel contains a liquid; and (II) deforming the pump body, e.g., with a piston, so that liquid or gas in the pump chamber exerts pressure on the fluid in the fluidic channel, whereby fluid in the fluidic channel moves through the fluidic channel.

Also disclosed herein is a method performed using a cartridge of this disclosure comprising: a) moving an extraction medium through at least one open valve in the cartridge to an extraction chamber in the cartridge comprising a biological sample and lysing cells in the biological sample to create an extract; b) moving the extract through at least one open valve in the cartridge to a reaction chamber in the cartridge; c) moving reagents for performing a biochemical reaction into the reaction chamber to create a mixture; d) performing a biochemical reaction on the mixture to create a reaction product; and e) performing analysis on the reaction product. In one embodiment the extraction medium comprises lysis buffer and the extract comprises a lysate. In another embodiment the analysis is capillary electrophoresis. In another embodiment performing capillary electrophoresis comprises moving the reaction product out of the cartridge and injecting it into an electrophoresis capillary. In another embodiment the one or more target sequences are STR sequences. In another embodiment the reagents comprise reagents for performing cycle sequencing, the biochemical reaction is cycle sequencing of a target sequence and the reaction product is a set of dideoxy-terminated polynucleotides. In another embodiment biochemical analysis comprises sequencing the set by performing capillary electrophoresis. In another embodiment the reagents comprise reagents for performing PCR and the biochemical reaction is PCR amplification of one or more target sequences. In another embodiment the method further comprises, before cycle sequencing, moving reagents for performing PCR into the reaction chamber and performing PCR on a target sequence and, optionally, purifying PCR product before performing cycle sequencing. In another embodiment the method comprises, moving a liquid from a first chamber in the cartridge through a fluidic channel comprising at least one open valve to a second chamber in the cartridge and, after the liquid has moved past the open valve, closing the valve. In another embodiment the method comprises, moving liquid from an inlet in the cartridge through a fluidic circuit in cartridge and out an outlet in the cartridge, wherein the fluidic circuit comprises a plurality of valves and wherein a biochemical reaction is performed on the liquid in the cartridge; and wherein no valve is closed and then opened before the liquid passes through the valve.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative claims, in which the principles of the disclosure are utilized, and the accompanying drawings of which:

FIG. 17 shows a sequence of steps in sample preparation. "O" indicates a ram does not press against a valve. "X" indicates a ram presses against and closes a valve.

DETAILED DESCRIPTION OF THE INVENTION

Fluidic Cartridge

A. Introduction

A cartridge of this disclosure (also referred to as a "sample cartridge") includes one or more valves formed from a malleable valve body and a layer of deformable material. Such valves are shut, at least initially, by application of concentrated force against the valve which both deforms the deformable layer toward the valve body and compresses at least a part of the malleable valve body to form a closure that shuts the flow of liquid through a fluid passage entering the valve. After initial closure, the valve can be opened by relieving the force that pinches the valve shut, and applying pressure to a fluid in a fluidic channel sufficient to force the membrane away from the valve body. The valve can be shut again by pressing the layer against the valve body, e.g., with mechanical or pneumatic pressure.

Unlike valves in which force on the closing member is more or less evenly distributed against the entire surface of a valve seat, valves of this disclosure use pressure that concentrates closing force against a portion of a valve body. This force is similar to a pinching action. In certain embodiments, the contact area between the deformable layer and the valve body that closes the valve is substantially linear, e.g., straight, rather than occurring over a more two-dimensional shape, such as a circle or a wide oval. Pressure can be applied mechanically, pneumatically or hydraulically. In certain embodiments, pressure is applied mechanically using a ram. The ram can have a head adapted to exert concentrated pressure. The tip or edge of the ram head can have a generally long and thin edge. That is, the ram can have a length aspect that is considerably longer than the width aspect. For example, the ram head can have a substantially straight and substantially flat tip, similar to the tip of a flat end screw driver or a knife. Alternatively, the longer aspect of the tip can be rounded. For example, the contact area between the deformable layer and the valve body can have an aspect ratio of length:width of at least any of 2:1, 3:1, 4:1, 5:1, 6:1, 7:1, 8:1, 9:1 or 10:1. The ram head can assume other shapes, for example, a rounded shape, as long as pressure exerted by the ram closes the valve.

Figure 1:
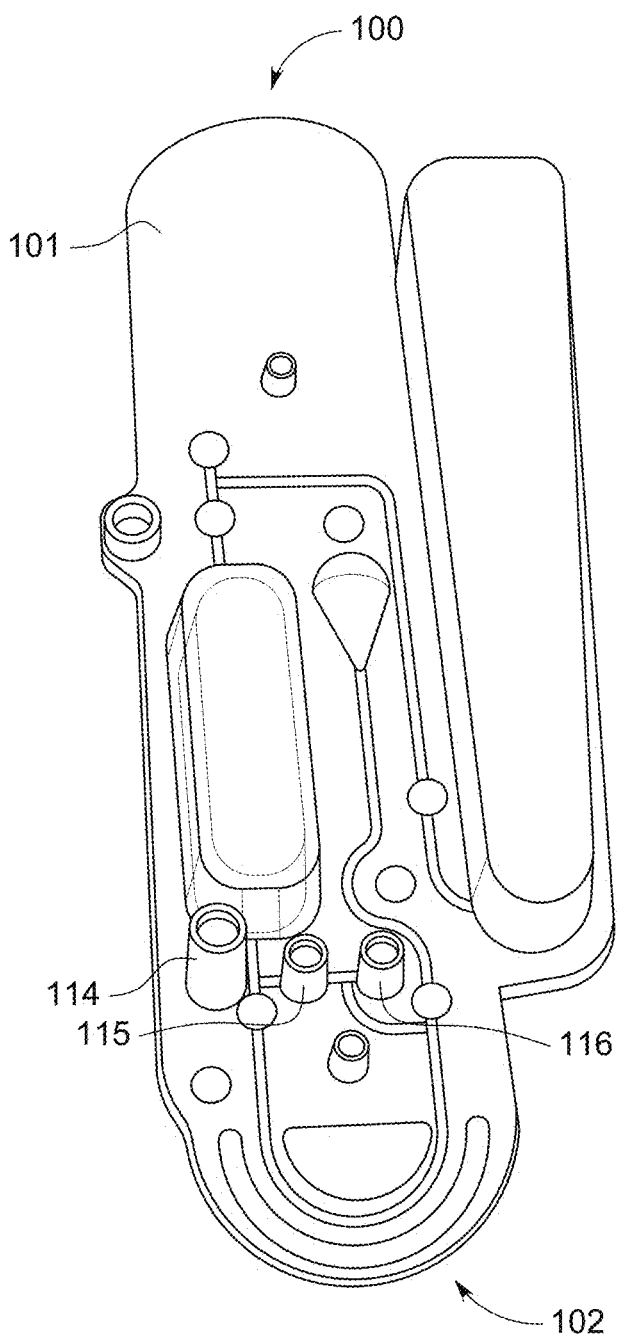
FIG. 1 shows an exemplary cartridge of the disclosure.

Referring to FIG. 1, cartridge 100 comprises a cartridge body 101 backed by a deformable layer 102. In this embodiment, body 101 is made of injection molded polypropylene. Deformable layer 102 is a layer of heat seal material which is a laminate including a polypropylene layer on a polyethylene backing.

Materials for the cartridge body and the deformable layer are selected which can be deformed by pressure exerted by the source of positive pressure, e.g., a mechanical ram. Typically, the deformable layer has the ability to stretch under pressure, and the valve body has the ability to compress or flow under pressure. In this way, concentrated pressure can be exerted against the valve sufficient to compress portions of the valve body without breaking (e.g., cracking) the deformable layer. Combinations of materials for the cartridge body and the deformable layer include, for example, polypropylene and heat seal, polyethylene and laser-welded polyethylene and Teflon and aluminum foil bonded with a patterned adhesive.

Figure 2:
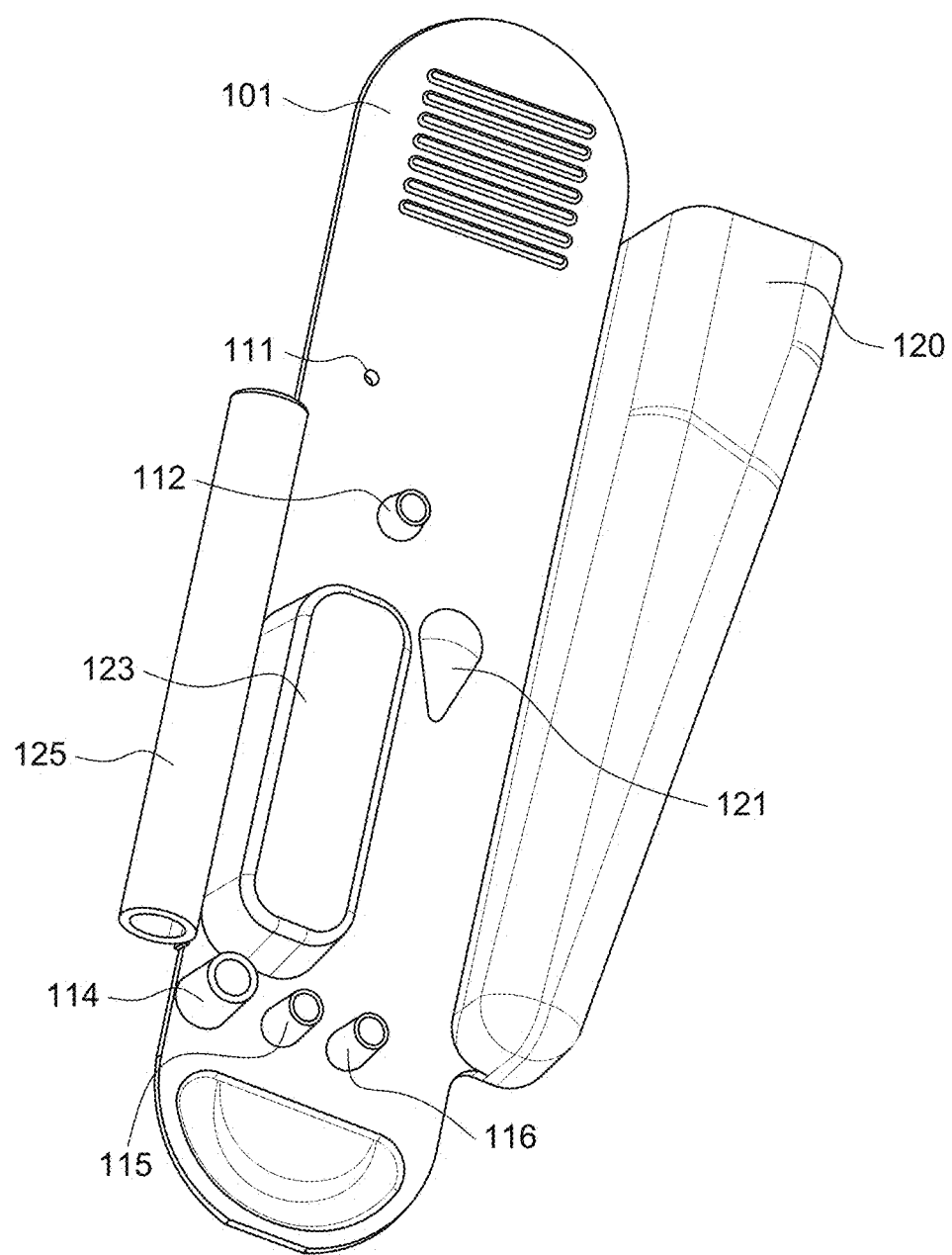
FIG. 2 shows an exemplary cartridge body this disclosure.

FIG. 2 shows a side of body 101, including ports 111, 114, 115 and 116; walls of chambers 120, 121 and 123; and piston barrel 125. In an alternative embodiment piston barrel 125 is replaced with port 112 as shown in FIG. 3 through which positive or negative pressure can be applied to the fluidic circuit to move liquids in the circuit.

Figure 8:
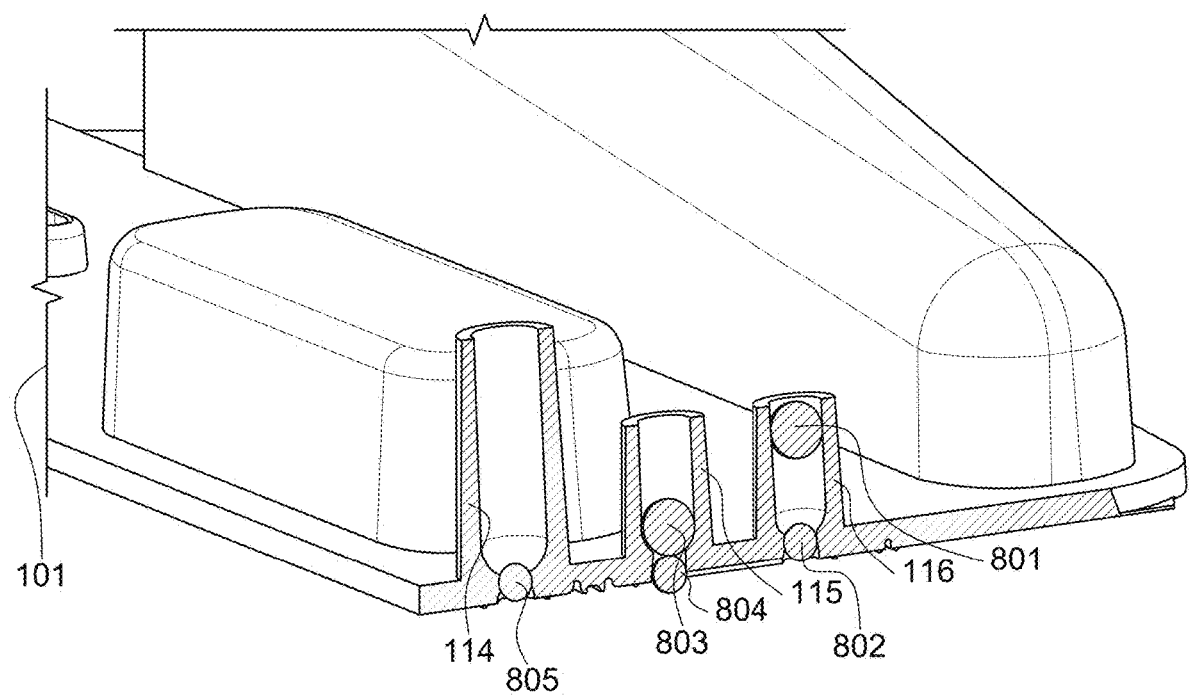
FIG. 8 shows a cutaway view of reagent containers of a cartridge sealed with ball valves.

FIG. 8 shows ports 114, 115 and 116 configured as chambers communicating with fluidic channels through vias. The chambers are configured to contain reagents and to deliver reagents to a fluidic circuit. The reagent delivery member is shown here as a dual plunger sealed chamber 116 having a first stopper 801 and a second stopper 802, in this case configured as balls. The stoppers 801 and 802 seal a receptacle (e.g., a column or tube 116) having a reagent (e.g., premix, master mix), such as an STR master mix. The application of force to the first stopper ball 801 (such as, e.g., with the aid of a plunger or a syringe) actuates the movement of the second stopper ball 802 ball away from the via, creating a flow path for the reagent to pass into channels 131 and 134.

Figure 3:
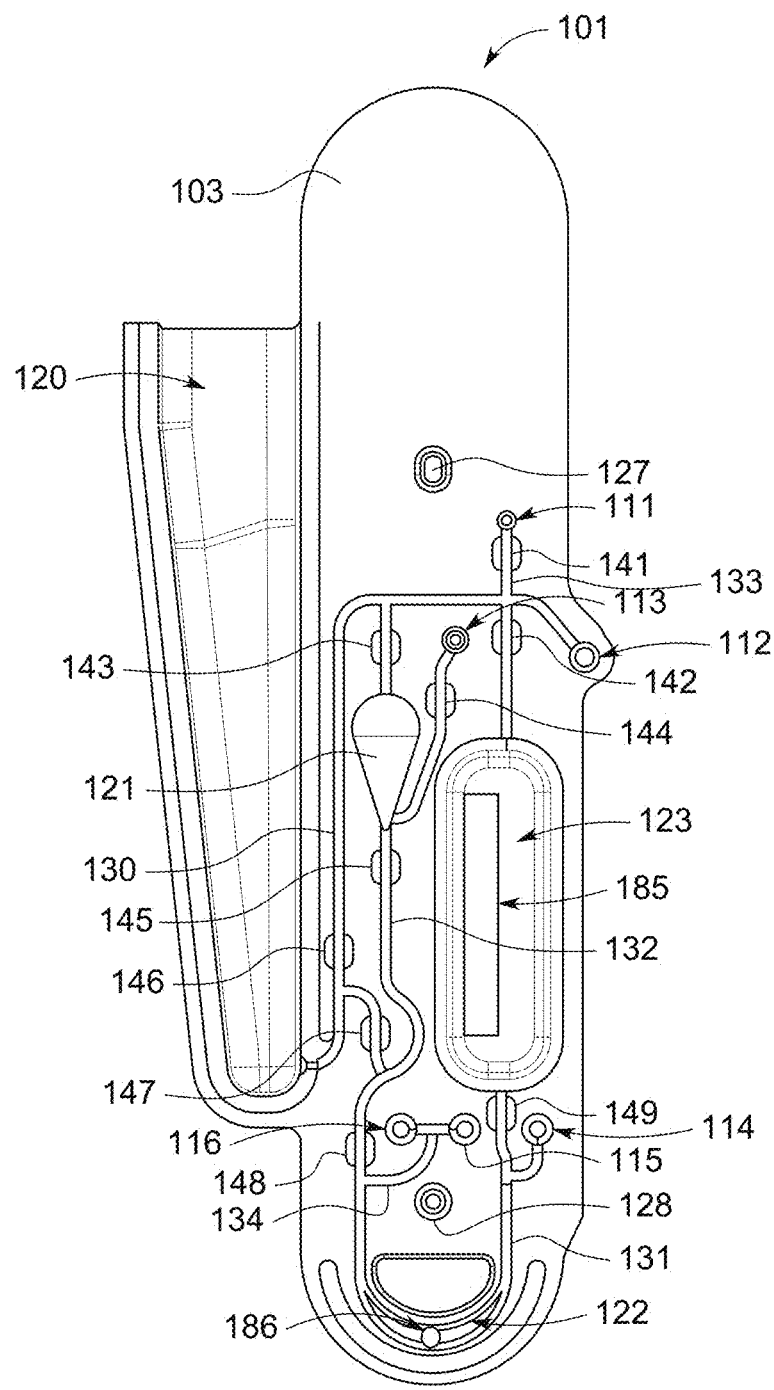
FIG. 3 shows a face of an exemplary cartridge body of the disclosure with elements of a fluidic circuit.

FIG. 3 shows the fluidic side of body 101. The fluidic side has a substantially planar surface 103 into which various elements of a fluidic circuit are formed by methods known to one skilled in the art, e.g., injection molding, hot embossing, laser cutting and 3D printing. A fluidic circuit includes ports 111-116 that communicate through vias with a non-fluidic side of the cartridge body and from which liquids can be introduced into the fluidic channels. Wells formed in the cartridge body create chambers 120, 121, 122, and 123. A fluidic circuit can comprise fluidic elements such as inputs, outputs, valves and chambers which are fluidically connected with fluidic channels. Fluidic elements, such as channels, chambers and valve bodies, typically include depressions in the body surface. A via, that is, a passage from one side of a cartridge body to another, is distinguished from a depression, which is formed in, rather than through, the body. For example, valve reliefs typically are formed as depressions.

Sample chamber 120 is configured to accept a swab, punch, or other sample type. This compartment can also serve as a lysis chamber. To accommodate the swab, punch, or other sample type, it can have a volume ranging from, e.g., 10 µL to 15 mL, e.g., 250 µL to 1 ml. Cells are lysed and analytes, such as DNA, RNA or protein, can be extracted from the swab, punch, or other sample type in this chamber.

Figure 26:
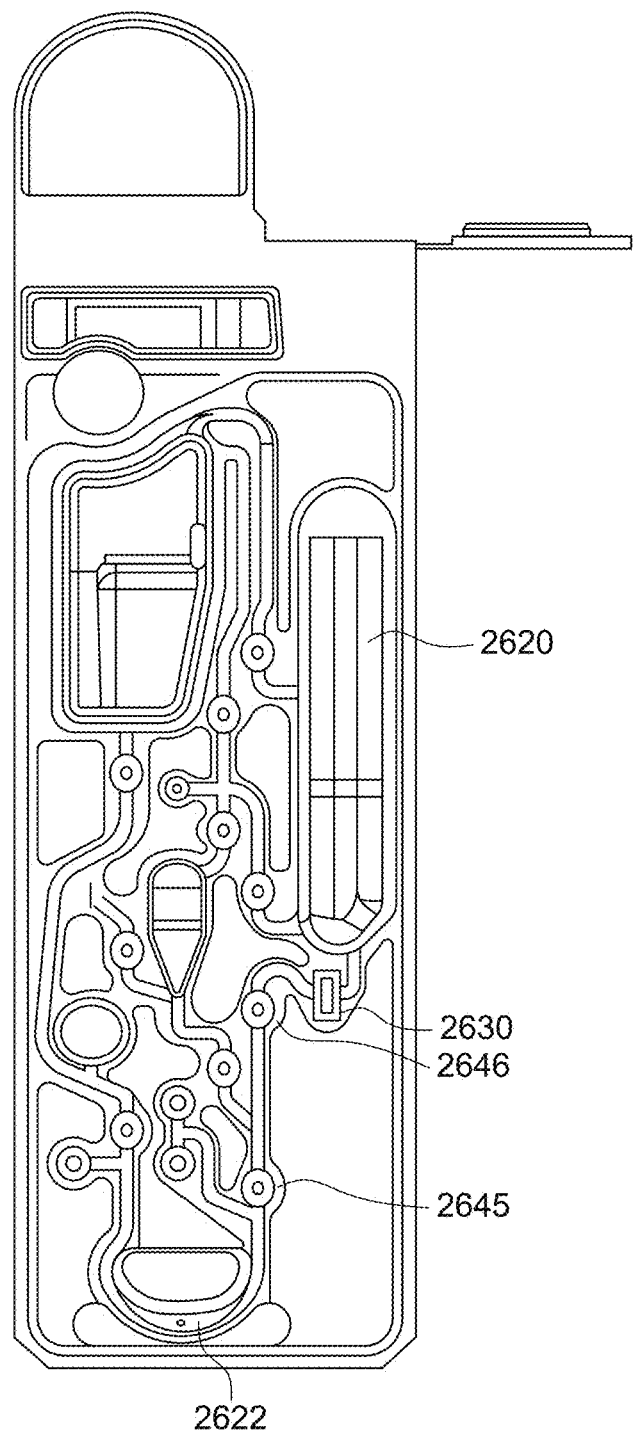
FIG. 26 shows an exemplary cartridge configuration of this disclosure comprising a chamber for a filter.

In some embodiments, the cartridge comprises a filter to filter liquid from a biological sample, such as a cell lysate. One such embodiment is shown in FIG. 26. The exemplary cartridge comprises filter chamber 2630 comprising a filter, in a flow path between lysis chamber 2620 and reaction chamber 2622, and typically between the sample chamber and a first valve, e.g., 2646. The filter can be a size exclusion filter having pores no greater than any of 100 microns, 50 microns, 25 microns, 10 microns or 5 microns. The filter can be, for example, a mixed cellulose ester, such as a Millipore™ Membrane Filter. Such a filter can be useful to capture particles that may clog valves or chambers in the flow path. In another embodiment, the filter is included around the outlet of the lysis chamber.

Chamber 121 functions as a mixing chamber. A mixing chamber can have a tapered shape such that air delivered from a channel on a side toward gravity bubbles air toward a side away from gravity.

Chamber 122 functions as a reaction chamber. This chamber can be temperature regulated, for example, to perform PCR. The reaction chamber can serve to capture DNA or house a small amount of lysate for direct amplification. It can also be used for cleanup and amplification. To minimize the duration of thermocycling and the amount of energy required, this chamber should have minimal volume, perhaps ranging from 2 µl to 25 µl, although other configurations are practical.

In one embodiment a fluidic device of this disclosure comprises a reaction chamber that comprises a solid substrate, e.g., solid phase extraction material 186, for retaining analyte from the sample. The solid substrate can comprise a material that binds the analyte, such as a nucleic acid such as DNA. The amount of solid substrate in a chamber can be selected to retain the predefined amount of analyte. For example, the material can be Whatman paper or carboxylated particles. Alternatively, the solid substrate can be an absorbent or sponge-like material that absorbs a predetermined volume of fluid. The material can be in the form of a monolith. The material can be, for example, PVDF (polyvinyldiene fluoride) or other membranes, filter paper, glass fiber filters, magnetically attractable particles, chromatography media, solid phase extraction materials, or glass particles. In operation, lysate is pumped through the chamber and a predetermined amount of analyte is retained on a solid substrate. Then, retained material is contacted with reagents, e.g., reagents for PCR. The resulting material can be incubated to form a reaction product. For example, the chamber can be put into thermal contact with a thermal-control device, such as a Peltier, and the reaction mixture can be thermally cycled. In another embodiment, the chamber can include a pocket or container designed to retain a defined volume of liquid. In another embodiment, the chamber can have a surface coating that retains the desired analyte, e.g. an antibody to capture epitopes or a single stranded nucleotide to capture a target nucleic acid. In another embodiment, the chamber could have a coating, e.g. PEG, that will retain a desired volume of liquid.

Chamber 123 functions as a waste chamber. A waste chamber can contain material 185 that degrades nucleic acids, polypeptides, or other analytes. For example a material can comprise a chlorinated material, such as calcium hypochlorite. In another embodiment, the material can comprise an enzymatic activity such as a DNAase, RNAase, protease, etc. Alternatively, the waste chamber can include an absorbent material that absorbs waste containing liquid. In another embodiment the nucleic acid degrading material is contained in a water-soluble capsule. In yet another embodiment the nucleic acid degrading material is combined with an absorbent material such as cellulose or polypropylene fibers.

These functional elements are fluidically connected by fluidic channels, for example, channels 130, 131, 132, 133 and 134. Liquid flow along the channels is regulated by valves. The valves include valve bodies formed in the cartridge body and portions of the deformable layer covering the valve body that can be deformed into the valve body, blocking flow in the fluidic channel. Valve bodies are shown in FIG. 3 as oblong elements, e.g., 141-149. More specifically, these valves include vent valve 141, waste vent valve 142, product top valve 143, product bottom valve 145, lysis valve 164, lysis transfer valve 147, cycler in valve 148, cycler out valve 149, product out valve 144. Alignment guide holes 127 and 128 mate with alignment pins in the cartridge interface.

Figure 4:
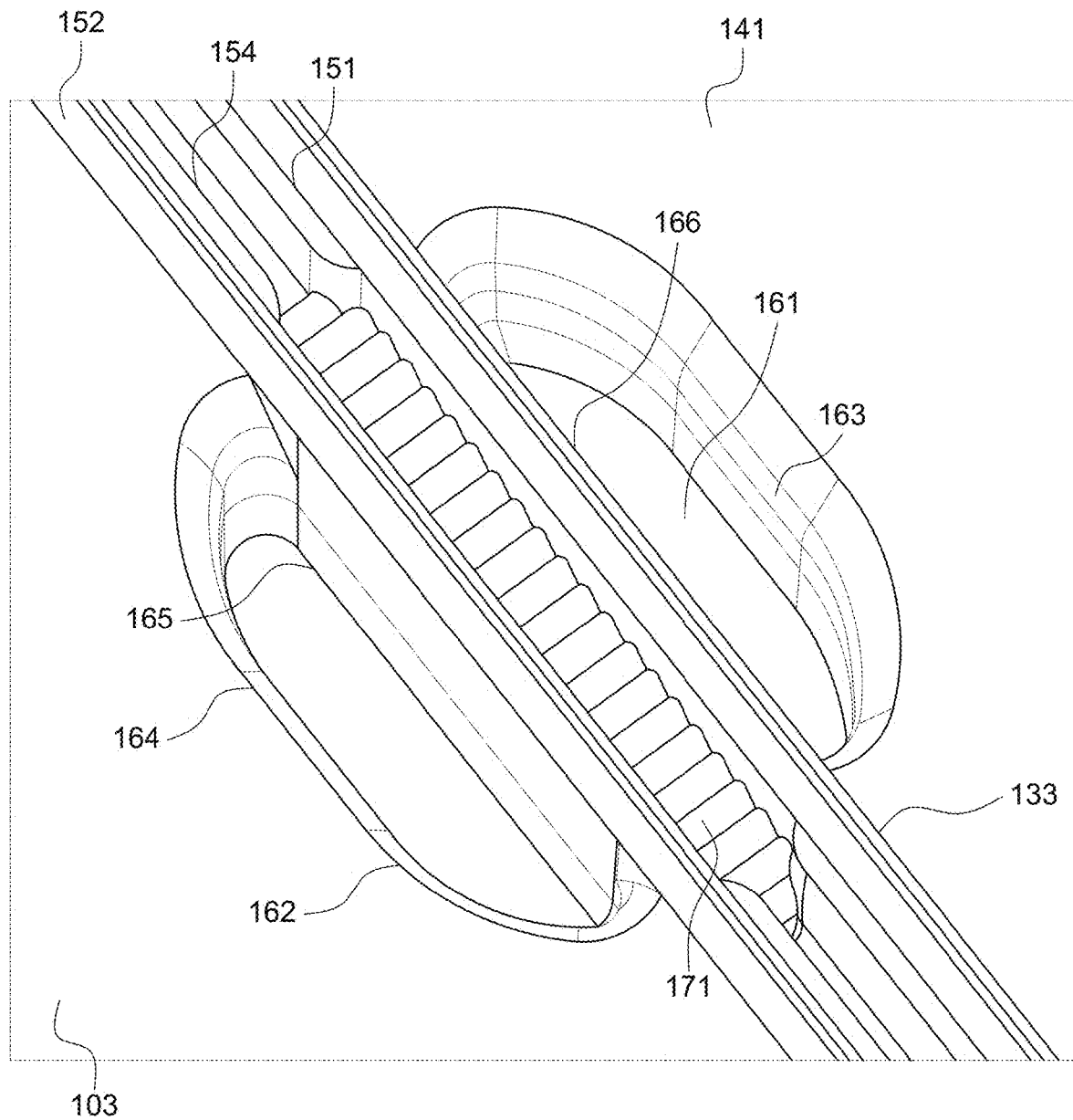
FIG. 4 shows an exemplary valve body of this disclosure.
Figure 5:
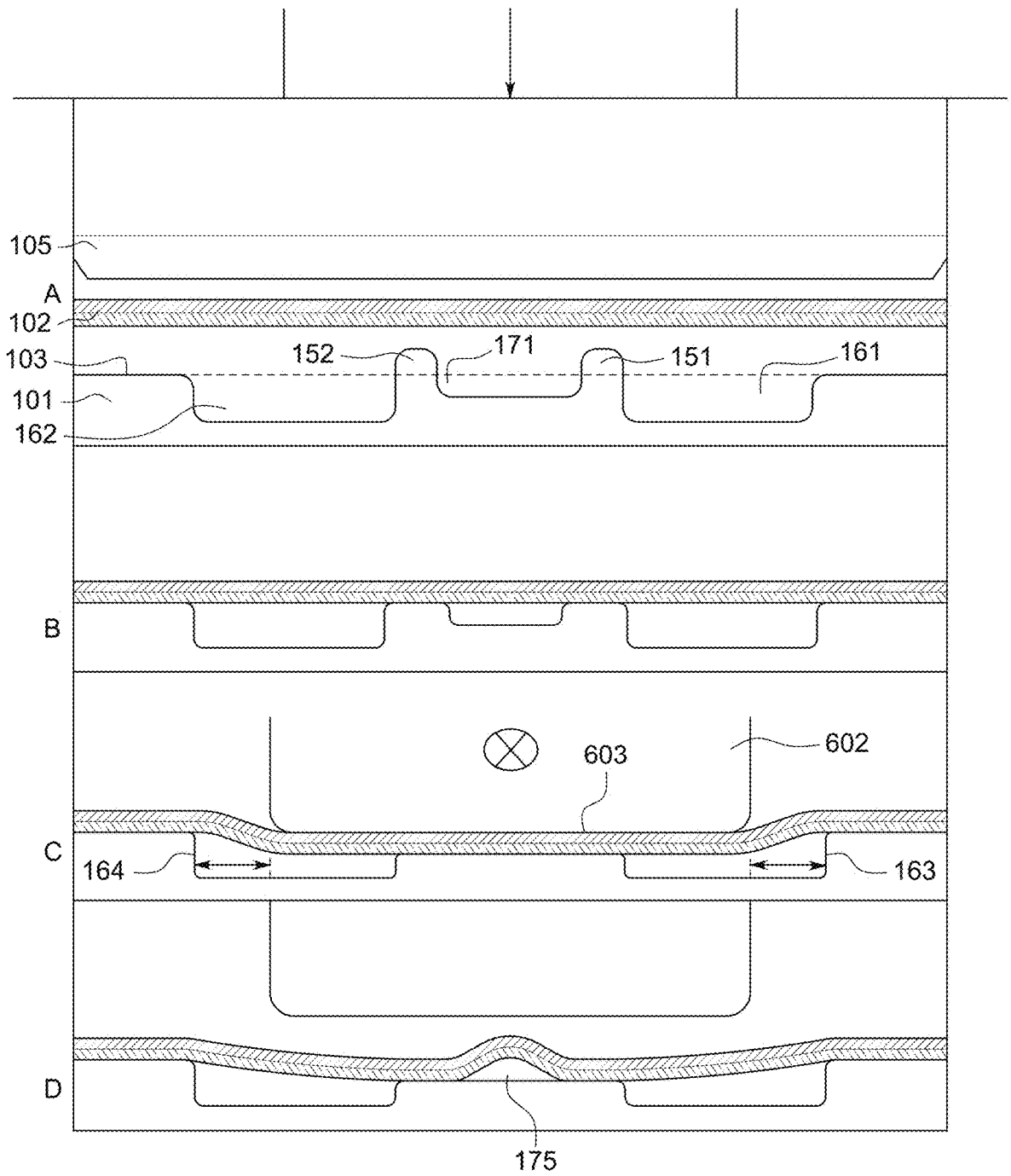
FIG. 5 shows an exemplary formation of a valve of this disclosure.

FIG. 4 is a detailed view of a valve body, e.g., element 141. Fluidic channel 133 includes raised ridges 151 and 152. These ridges are raised above the plane (i.e., away from the body) of the generally flat surface 103 of the fluidic side of the cartridge body 101. Furrow 154 of channel 133 forms a recessed channel in surface 103 of the fluidics side, that is, disposed below the plane (i.e., into the body) of surface 103. Valve body 141 includes walls that define reliefs 161 and 162 that flank channel 133. Relief 161 is defined in part by near wall 166 and far wall 163. Relief 162 is defined in part by near wall 165 and far wall 164. The reliefs also are disposed below the plane of surface 103. Corrugated area 171 is shallower than furrow 154 and functions as a force concentrator.

Figure 18:
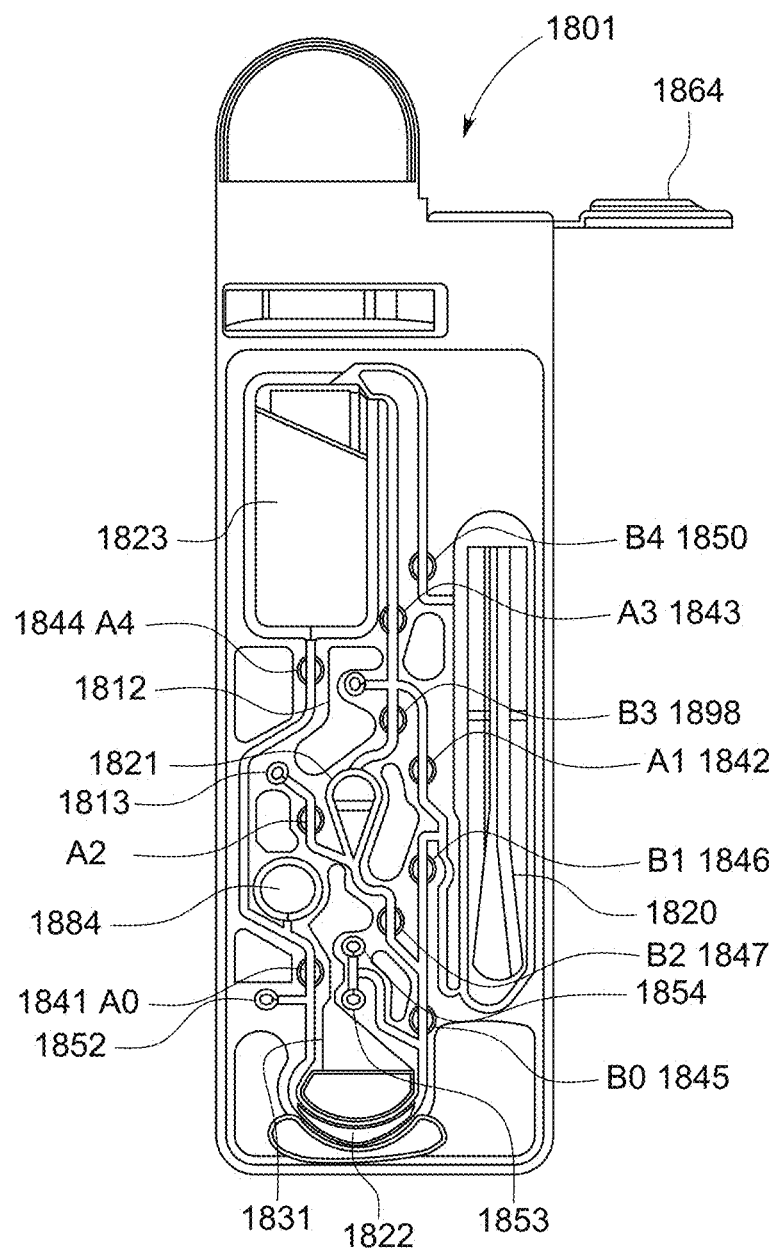
FIG. 18 shows an exemplary cartridge body of this disclosure.

FIG. 18 shows another embodiment of a cartridge body. Cartridge body 1801 includes the following valve bodies: 1841 Cycler Out (A0), 1842 Lysis (A1), 1843 Waste Shut Off (A3), 1844 Waste In (A4), 1845 Cycler In (B0), 1846 Lysis Transfer (B1), 1847 Product Bottom (B2), 1848 Product Top (B3) and 1850 Vent (B4).

Valve bodies can include various types of valves, such as valves actuated with the aid of rams described in U.S. Provisional Patent Application Ser. No. 62/001,533, filed Mar. 21, 2014, and U.S. Provisional Patent Application Ser. No. 62/067,120, filed Oct. 22, 2014, each of which is entirely incorporated herein by reference. As an alternative, the valve bodies can include Micro-Robotic on-Chip Valve and Pump valves (MOVe), as described, for example, in U.S. Pat. Nos. 8,394,642 and 8,672,532, each of which is entirely incorporated herein by reference.

In the embodiment of FIG. 18, cartridge body 1801 includes lysis chamber 1820. Cartridge 1801 can include reagent chambers (e.g., 114, 115 and 116) filled with, e.g., nucleic acid size standards (molecules of known sizes), PCR master mix and PCR primers, respectively, and sealed with, e.g., balls (801, 802, 803, 804, 805) acting as closures for ball valves. When opened, the reagent chambers come into fluidic communication with fluidic channels in sample cartridge 1801, for example, through ports 1852 (internal lane standard), 1853 and 1854 (PCR Master Mix and PCR Primer Mix). Pistons, 1511 and 1512 actuate the ball valves, pushing fluids through the ports and into the channels to which they are connected. Sample cartridge 1801 also can include inlet port 1812 and output port 1813. Upon engagement with the cartridge interface, inlet port 1812 and outlet port 1813 each engage a fluid line. The fluid line connected to inlet port 1812 can be attached to a pressure source, e.g., a syringe, to exert positive or negative pressure to fluidic channels via the inlet port, transporting liquids, such as lysis buffer, water or air, into or out of the cartridge. The fluid line connected to output port 1813 can conduct analyte from the cartridge to a sub-system for analyte analysis.

In the embodiment of FIG. 18, cartridge body 1801 includes lysis chamber 1820 and, optionally, closable cap 1864 to close lysis chamber 1820. Cartridge 1801 includes pump 1884. Pump 1884 (e.g., an air pump) is configured as a chamber defined by walls of the cartridge body. Pump 1884 is fluidically connected to at least one fluidic channel in the cartridge body. Walls of the pump comprise, at least in part, the malleable material of the cartridge body. Accordingly, the walls can be deformed, for example by mechanical force, increasing pressure in the chamber to pump liquid or air in fluidic channels in fluidic communication with the pump. Pump 1884 can be actuated with a plunger or piston 1513 that depresses walls of pump 1884 and forces, for example, air from the pump body through the fluidic channel to which it is connected. Pump 1884 can be used to clear fluid from a fluidic channel. For example, in this embodiment, reagent introduced from port 1882 into reaction chamber 1822 may leave dead volume in channel 1831. Pump 1884 can be used to pump this dead volume of reagent into reaction chamber 1822.

B. Materials

1. Cartridge Body

At least the valve body of the cartridge body comprises a malleable material, that is, a material capable of plastic deformation. The material, after being deformed, does not return to its original shape. In certain embodiments the malleable material is a plastic, a wax or a soft metal (e.g., lead). The plastic can be, for example, a thermoplastic, a thermoset, a single component resin or a multi-component resin. In one embodiment, the cartridge can comprise an injection molded body, for example, a thermoplastic, and a deformable layer bonded to the body. The thermoplastic can include any thermoplastic known to those skilled in the art, such as polypropylene, polystyrene, polyethylene, polyethylene terephthalate, polyester, polyamide, vinyl, poly(vinylchloride) (PVC), polycarbonate, polyurethane, polyvinylidene chloride, cyclic olefin copolymer (COC), or any combination thereof.

The body can have an external surface comprising elements of fluidic circuits, such as channels, compartments, vias, and valve seats. The body can be made by injection molding of the thermoplastic, 3D printing or other methods well known to one skilled in the art. These features can be covered with a layer of deformable material attached to the surface of the cartridge body. The layer can function to seal otherwise open features such as channels and compartments. The layer of deformable material can deform to contact a valve seat, thereby closing the valve.

The material can be attached to the surface of the body using a selective bonding process in which the material bonds to selected portions of the surface during the bonding process and does not bond to un-selected portions of the circuit after the bonding process is complete. For example, the material may bond to surfaces other than fluidic elements during the bonding process, and not bond to fluidic elements, such as channel floors, chamber walls and valve seats, after the bonding process. Methods for selective bonding include, for example, thermal bonding (e.g., heat sealing, welding, laser welding), chemical bonding (e.g., chemical bonding of oxide to PDMS, vapor bonding) and selectively placed adhesives.

In one embodiment a layer of the deformable material is attached to a surface of a cartridge body through thermal bonding. This can include thermally bonding the material directly to the surface, or thermally bonding the material through an intermediate layer of material. In the latter case the material can be a laminate in which a deformable material is coated with a layer of material that contacts the surface and that melts at lower temperature than the deformable material. In either case bonding typically comprises contacting the layer of deformable material to the body to form a combination and using a die to apply heat and pressure to the combination. Application of heat and pressure melts substrates in locations at which the material and body are in contact and fuse them, e.g., through coalescence. This process is more generally referred to as welding.

2. Layer of Deformable Material

The layer of deformable material (also called a "deformable layer") used in cartridges disclosed herein can comprise a plastic material (plastic deformation) or an elastic material (elastic deformation). The plastic material can comprise, without limitation, a polymer or a metal. Suitable plastic materials for the layer of deformable material include, without limitation, polypropylene and polyethylene. Suitable metals include, for example, aluminum. Suitable elastic materials include, for example, elastomeric materials such a polysiloxanes, e.g., PDMS. Other deformable materials are further described herein.

A material that bonds to a body through application of heat and pressure is referred to herein as a "heat seal". Heat seals are well known in the art and are commercially available. For example, 4titude (Wolton, Surrey, UK) commercializes a variety of heat seals. These heat seals are described on the www website 4ti.co.uk/sealing/heat-seals/. These include, for example, Clear Seal, Clear Weld Seal, and Foil Seal. Heat seals also are produced by Axygen, a Corning brand (Corning, Tewksbury, MA, USA). These include Axygen® PlateMax heat sealing film and sealing film rolls. See the website: catalog2.corning.com/Life-Sciences/en-US/Shopping/Product.aspx?categoryname=Genomics+and+Proteomics(Lifesciences)%7cPCR+Products(Lifesciences)%7cSealing+Films+and+Tapes+for+Microplates(Lifesciences)%7cHeat+Sealing+Films+and+Tapes+for+Microplates(Lifesciences).

The deformable material can be a homogenous or non-homogenous material. In certain embodiments, the heat seal material is made from the same material as the body of the cartridge. It can comprise a thermoplastic (e.g., polypropylene, polyethylene, polystyrene, cycloolefin co-polymer (COC), mylar, polyacetate) or a metal (e.g., aluminum). See, e.g., WO 2012/136333. The heat seal can be produced by contacting a heat seal layer with the body and applying heat and pressure. Non-homogeneous films include laminates having a first side for contact with the heater and a second side for contact with the body. The first side has higher melting temperature ("high melt") than the second side ("low melt"). This permits use of a heat source to bring the second side to its melting temperature before the first side allowing bonding to the body without bonding to the heater.

FIGS. 5A-5D show the attachment of a layer of deformable material to the fluidics face 103 of cartridge body 101 and the formation of a closed valve. FIG. 5 depicts a cross-section of valve 141.

FIG. 5A shows cartridge body 101, heatable die 105 and laminated seal 102 sandwiched between them. Cartridge body 101 includes surface 103, reliefs 161 and 162, ridges 151 and 152, and shallow corrugated area 171. This figure also shows that ridges 151 and 152 are formed as areas raised against the planar surface 103, while reliefs 161 and 162, and channel floor 171 are formed as areas depressed or recessed against the plane of surface 103.

Ridges can be between about 25 microns and about 100 microns above the plane of the surface of the cartridge that mates with the deformable layer, e.g., about 50 microns. The channel floor in the valve body can have a depth below the plane between about 50 microns and about 300 microns. If the deformable layer is attached by a method other than heat sealing, e.g., with a patterned adhesive or with laser welding, then the ridges do not need to rise above the plane of the surface. Fluidic channels that are either microfluidic, that is, having an aspect less than 500 microns) or macrofluidic, that is, having no aspect less than 500 microns (e.g., having no aspect less than 1000 microns). Fluidic channels can have a depth of about 100 microns to about 400 microns.

Figure 24:
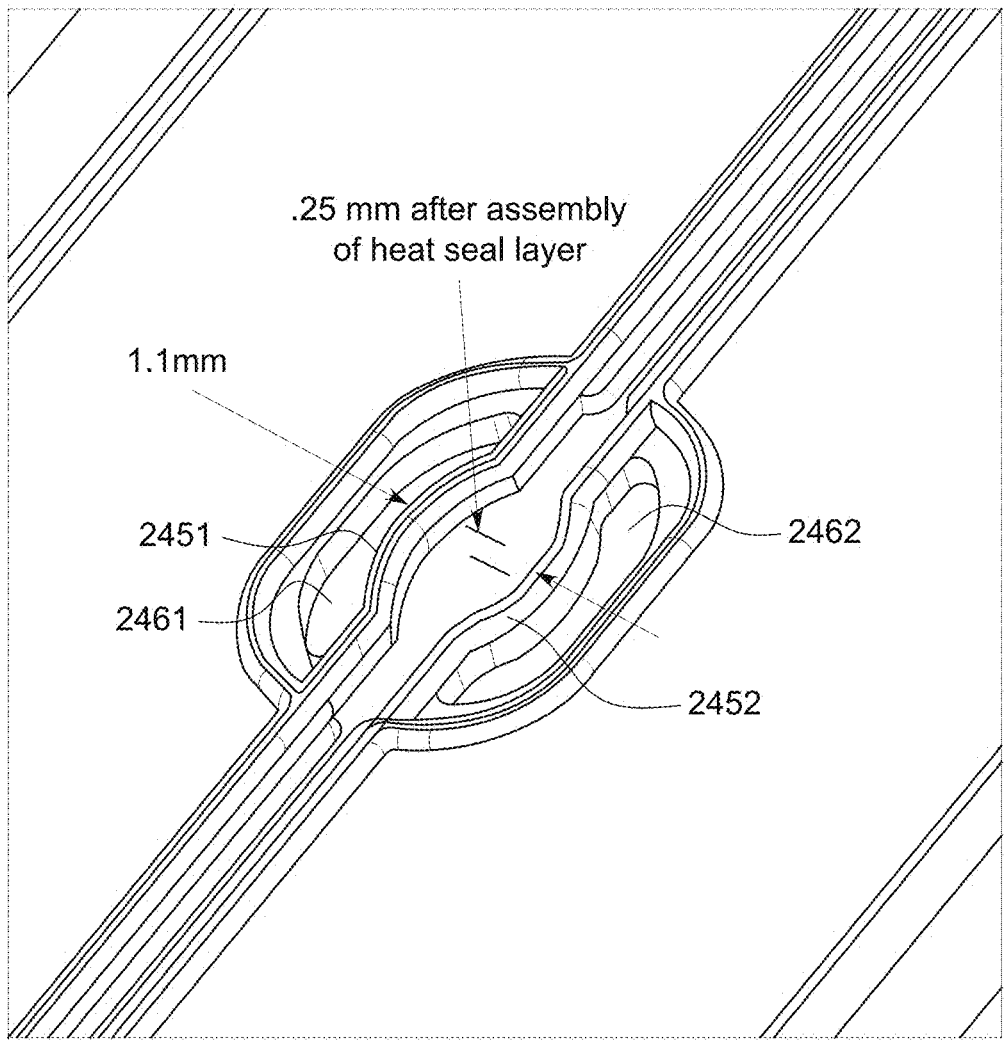
FIG. 24 shows an exemplary valve body.

FIG. 24 shows another embodiment of a valve body. In this embodiment ridges 2451 and 2452 take a curved shape, in this case a convex shape that bulges away from the lines of the fluidic channel and toward the walls of valve reliefs 2461 and 2462. At their most distant, they are separated by a distance of about 1100 microns. The channel floor in the valve body has a depth below the plane in this embodiment of about 100 microns. After application of the heat seal, the distance between the heat seal and the bottom of the channel is about 250 microns.

The layer of deformable material 102 is bonded to cartridge body 101 by pressure and heat applied by die 105. The layer of deformable material 102 is a laminate. One side of the laminate contacts the die. This side has a melting temperature higher than the temperature of the die. Therefore, when the heated die is pressed against the deformable material 102 the higher melting side does not melt or stick to the die surface. The other side of the laminate contacts surface 103 of cartridge body 101 and has a melting temperature lower than the temperature of the die. Accordingly, this material melts when the heated die is applied. The cartridge body also comprises a malleable material that melts when pressed against the heated die.

Consequently, as shown in FIG. 5B, after application of pressure and heat by the die, ridges 151 and 152 are compressed or crushed. Also, the layer of deformable material is selectively bonded to the cartridge body, in this case, to surface 103 and to ridges 151 and 152. Through this bonding the deformable layer seals fluidic elements of the fluidic circuit, including ports, chambers, channels and valves.

Figure 6:
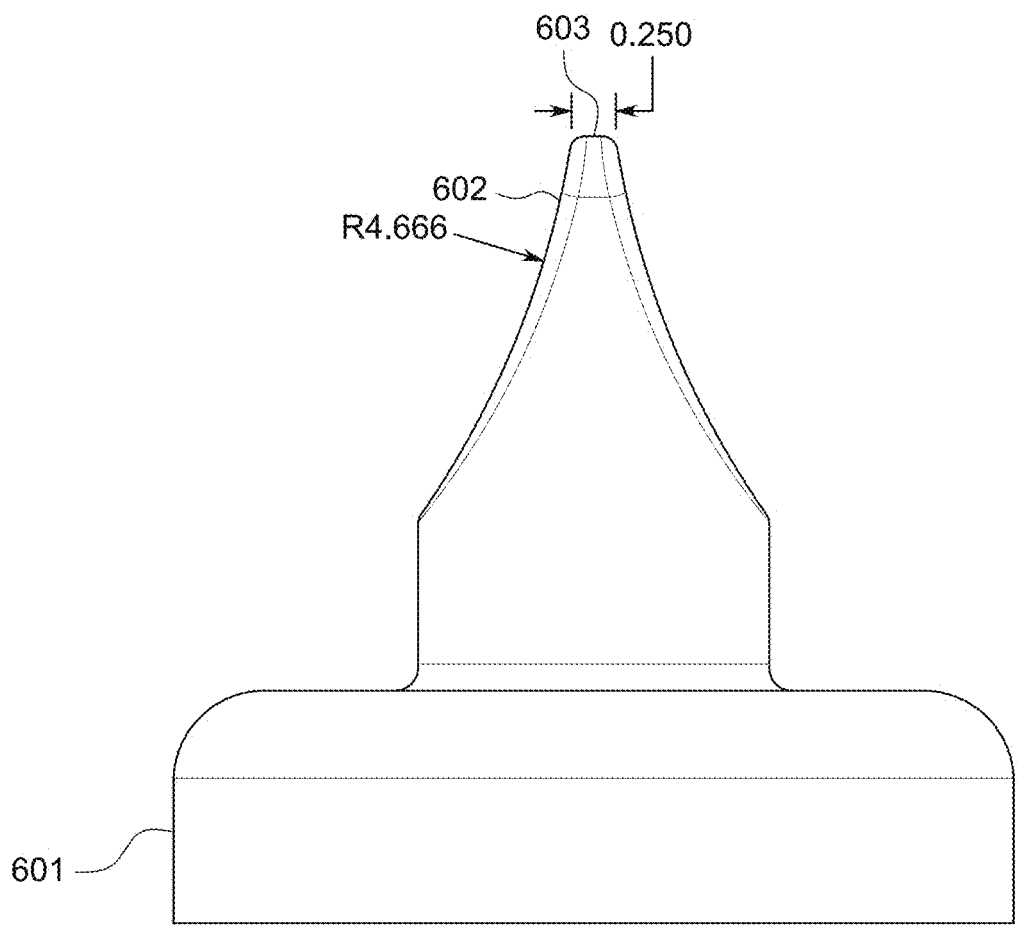
FIG. 6 shows an exemplary ram head this disclosure.
Figure 7:
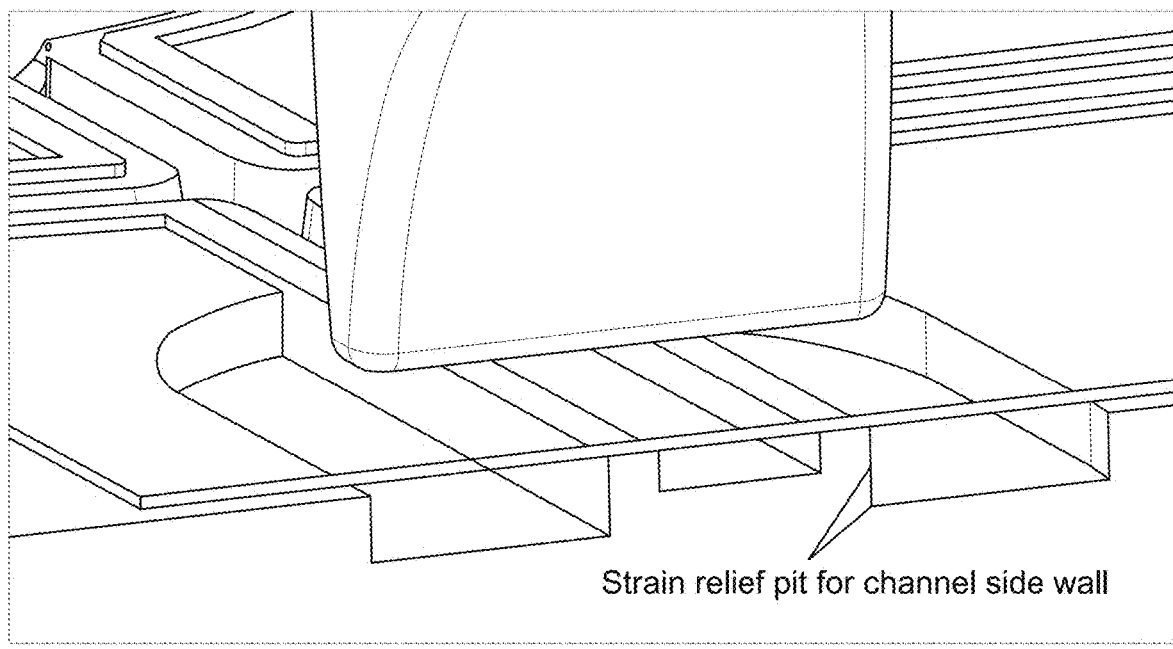
FIG. 7 shows a ram head positioned against a valve of this disclosure.

Valves are closed by use of force applied by a ram. FIG. 6 shows an embodiment of the head of ram 601. Ram has a tapered head 602 and a flat edge 603. FIG. 7 shows the ram head oriented against a valve.

FIG. 5C shows closing of the valve in cross-section. Ram head 602 is wider than the distance between the outside walls of ridges 151 and 152. However, ram head 602 is not as wide as the distance between the far walls 163 and 164 of reliefs 161 and 162.

The distance between the far walls provides clearance for ram 602 to be laterally shifted toward either wall 163 or 164 (depicted by double arrow lines) while still completely contacting ridges 151 and 152. Furthermore, the oblong shape of the relief area allows for the ram head to be shifted along the axis depicted by the circle X, while still clearing the walls of the valve reliefs. Accordingly, in an instrument in which a plurality of rams in a cartridge interface must be aligned with a plurality of valves in a cartridge engaged with the interface, the valve reliefs provide greater tolerance for the relative positioning of rams and valves.

The pressure of the ram presses the layer of deformable material against the valve body and, in an initial application, crushes the raised ridges against the corrugated base of the channel. This coins or stamps the valve body into a closed or closable position. For this purpose, the layer of deformable material must have a strength (e.g., yield strength or ultimate strength) that is greater than the strength of the ridges, such that pressure from the ram crushes the ridges but does not break the deformable layer. In this configuration the valve is closed and no liquid can pass through the valve.

Referring to FIG. 5D, to open the valve to allow the passage of liquid, the ram is retracted from the cartridge. The deformable layer is bonded to the remains of the ridges but is not bonded to the floor of channel 171. Accordingly, when pressure is exerted against liquid in a channel entering the valve, the liquid applies enough force to create an opening between the floor and the layer of deformable material, creating open passage 175. To close the valve, ram head 602 is pressed against the layer of deformable material, actuating the layer of deformable material against the valve seat and closing the passage, as shown in FIG. 5C.

Figure 9:
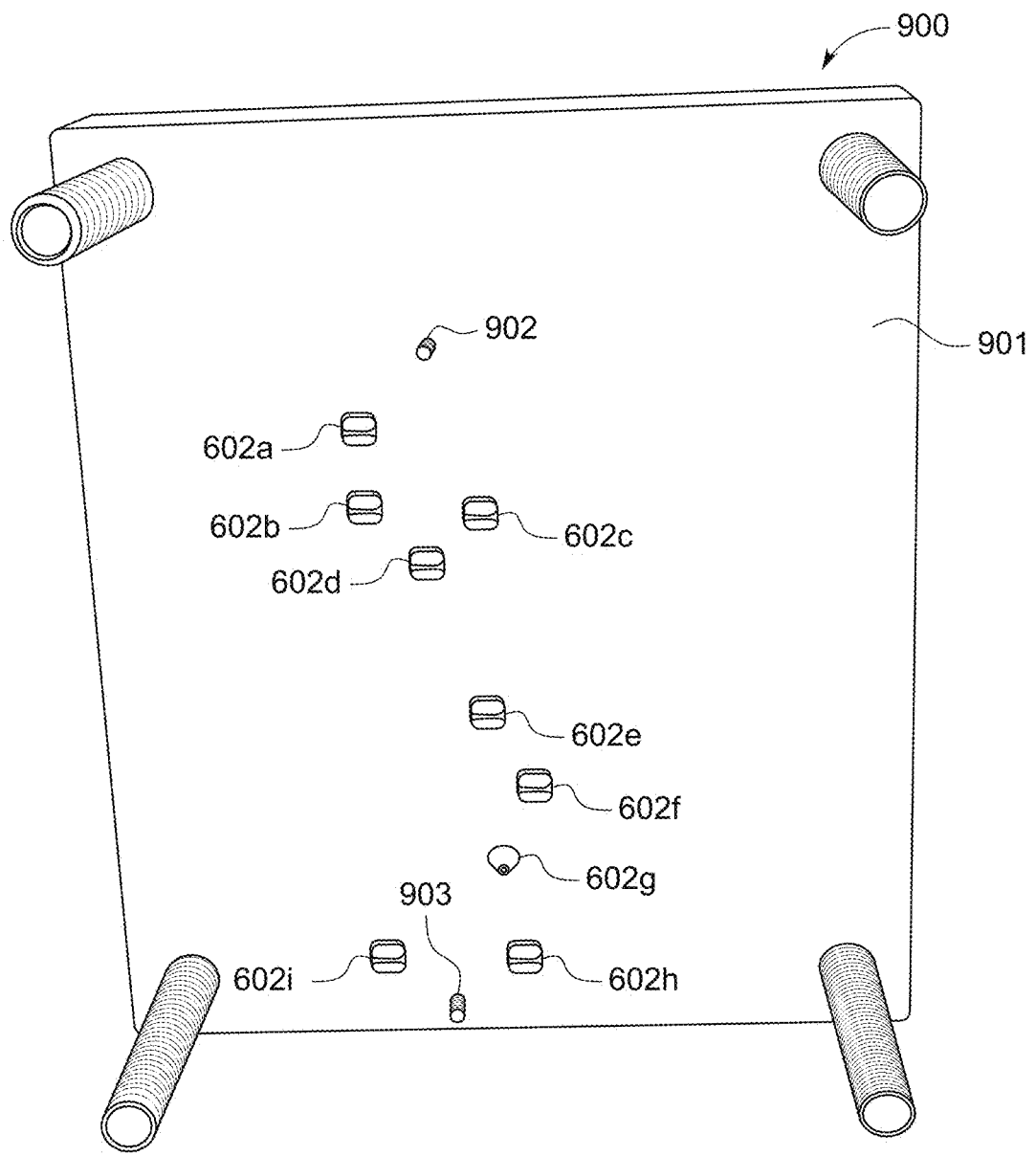
FIG. 9 shows an exemplary base plate of a cartridge interface of this disclosure.

FIG. 9 shows an example of a base plate 901 of cartridge interface 900. The planar face of the interface is configured to mate with the planar side 103 of the fluidic cartridge. Retractable, spring-biased rams are shown in a protruding position from the surface of the interface as ram heads 602a-602i. In this position, the rams hold valves shut. Also shown are two guideposts 902 and 903 that position the cartridge using alignment guide holes 127 and 128.

Figure 10:
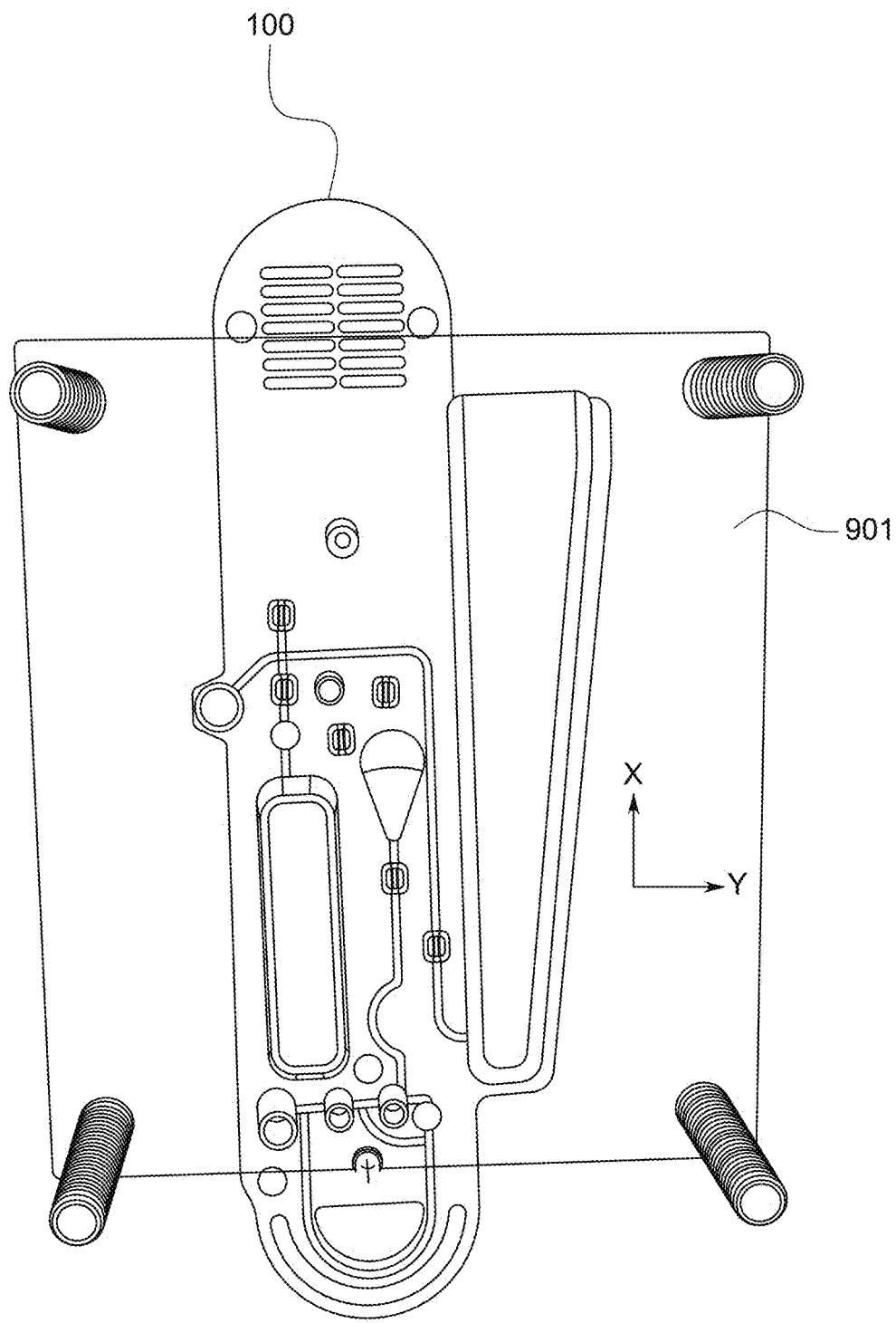
FIG. 10 shows an exemplary cartridge mated with an exemplary base plate of a cartridge interface of this disclosure.

FIG. 10 shows cartridge 100 engaged with base plate 901 of cartridge interface 900. As discussed above, the valve reliefs provide clearance for the rams in the X-Y plane.

Figure 11:
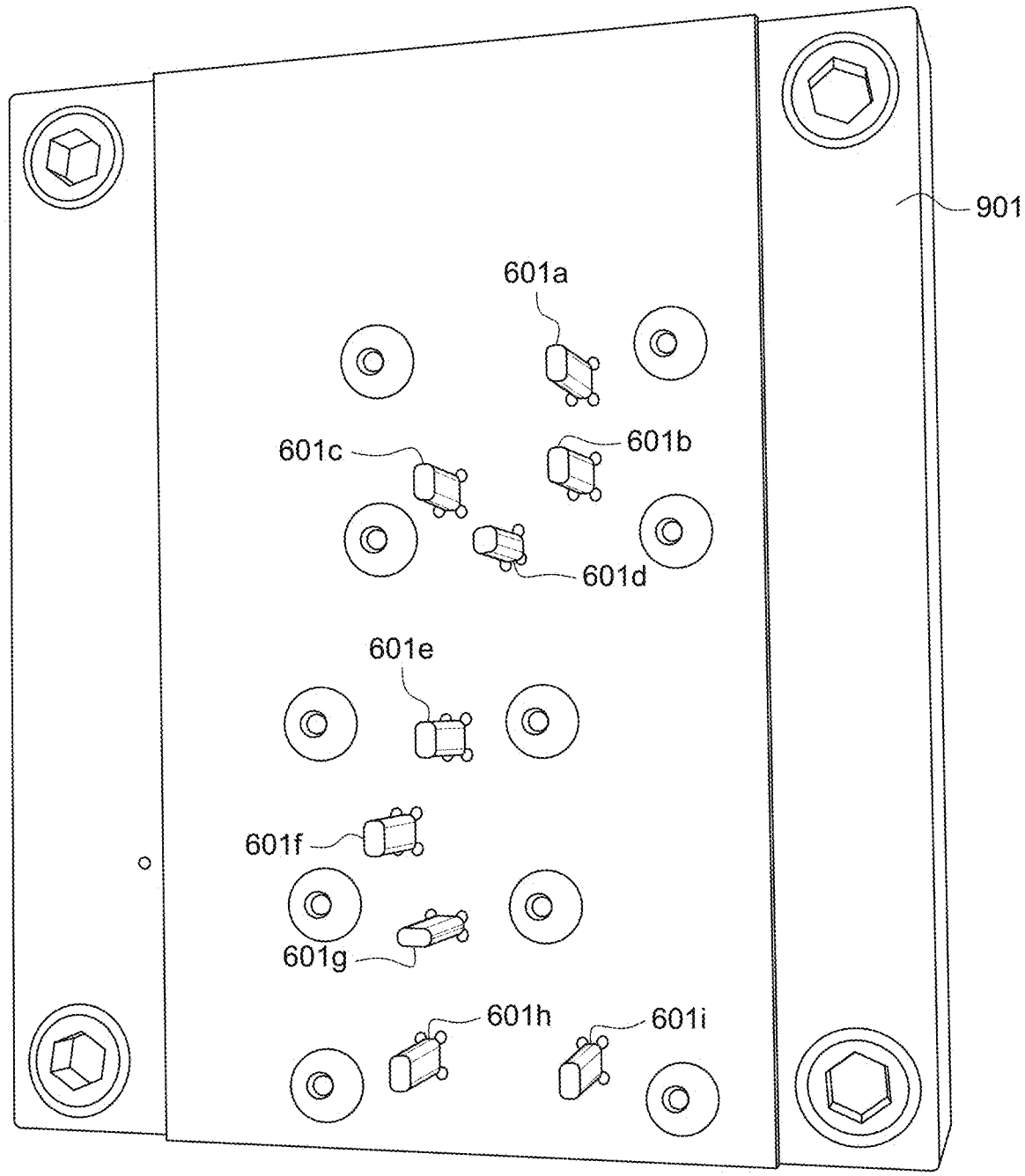
FIG. 11 shows the reverse side of a base plate of the cartridge interface of FIG. 9.

FIG. 11 shows the opposite side of base plate 901 of cartridge interface 900. Rams 601a-601i, protruding from the back, can be pulled and/or pushed. Pulling retracts the ram heads from the engagement surface of the cartridge interface. Pushing the rams makes them protrude from the plane of the engagement surface, actuating neighboring valves in the cartridge. Rams may be pushed through a bias exerted by an internal spring or by an external force made part of the cartridge interface assembly.

FIGS. 13-16 show an alternative embodiment of a cartridge interface 1500 mated with a sample cartridge 1801. In this embodiment rams are comprised in a cam mechanism 1300. Cam mechanism 1300 comprises cam 1313 and cam follower 1311. Cam 1313 has cam surface 1321, cam protrusion 1319 and cam aperture 1315 configured with a cam key 1317 adapted to position the cam on a rotating element. Cam follower 1311 is mounted on lever 1303, which rotates about axle 1301. Ram 1309 (sometimes referred to as a "knife") is configured as a protrusion on lever 1302. Ram 1309 can be configured as a piece held in place by a holder on lever 1303. The lever can be biased toward the valve with a biasing element 1305, for example with a spring. A spring can be mounted on mount 1304. In one embodiment, a biasing element exerts a force of at least any of 5 pounds, 6 pounds, 7 pounds, 8 pounds, 9 pounds or 10 pounds. The cam can be a plate cam, e.g., can take the shape of an eccentric disc comprising an eccentricity 1319. The cam can include an aperture 1317 adapted for mounting the cam on a rotation device, such as a drum driven by a motor. The cam aperture can include a key 1317 to align the cam on the drum. Rise of the cam follower pushes the ram away from the valve. Return of the cam follower allows the ram to push against the valve from the force of the biasing element. In certain embodiments, the cam surface 1321 may pull away from cam follower during valve closure, to allow biasing element 1305 to exert full force against the valve.

Cartridge interface 1500 includes ram actuation assembly 1517, base plate 1515 and cover plate 1516. Sample cartridge 1801 is inserted into a slot formed by the mating of base plate 1515 and cover plate 1516.

Ram actuation assembly 1517 can include cam array 1501; ram array 1509 and an array of biasing elements. The cam array can comprise a plurality of cams 1313 mounted on rotating drum 1507. The ram array can comprise a plurality of ram effectors, each comprising lever 1303 mounted on axle 1301, ram 1309 and cam follower 1311. Each ram mechanism is configured to engage a cam, and each ram to engage a valve of the sample cartridge.

Base plate 1515 includes a surface against which a surface of a cover plate can mate and apertures through which rams can protrude. Rams can be biased against a wall of the aperture for guidance.

Figure 20:
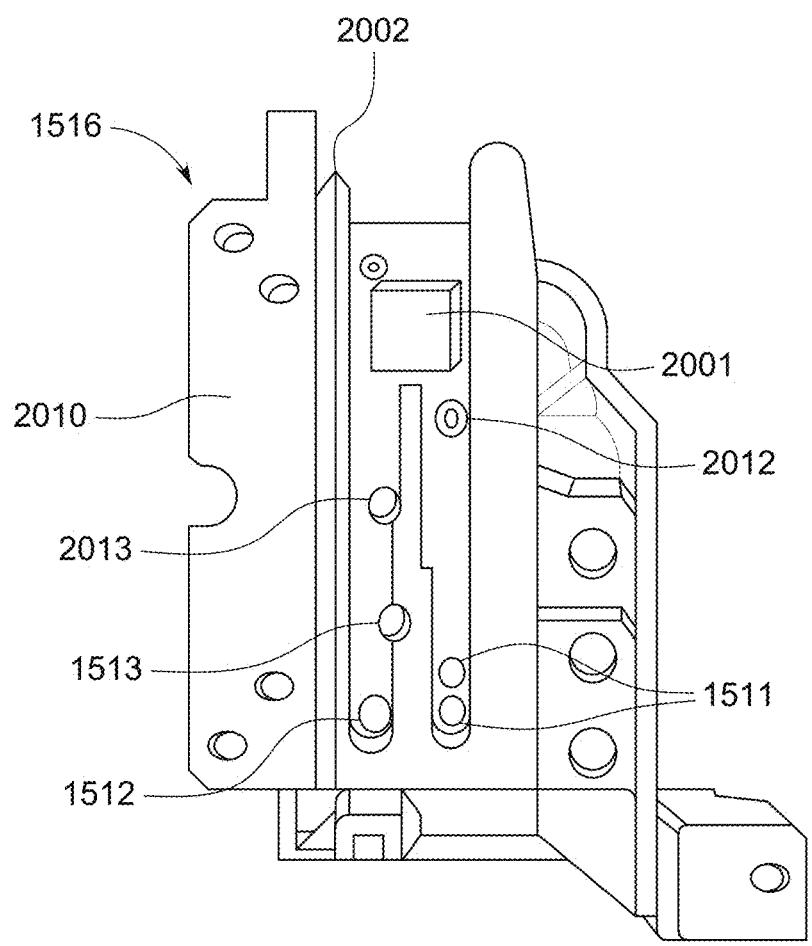
FIG. 20 shows an exemplary cover plate of an exemplary cartridge interface of this disclosure.

Cover plate 1516, also shown in FIG. 20, includes face 2010 configured to mate with a face of base plate 1515. It also includes recess 2001 configured to fit a cartridge, and cartridge guide 2002. Cover plate 1516 includes piston or plunger 1511 (a dual plunger) configured to actuate ball valves to chamber connected to ports 1853 and 1854, plunger 1512, configured to actuate ball valves to a chamber connected to port 1852, and plunger 1513, configured to actuate pump 1884. Cover plate 1516 also includes port 2012, adapted to mate with port 1812 in cartridge 1801, and port 2013, adapted to mate with port 1813 in cartridge 1801. Port 2012 can be fluidically connected to a fluidic assembly including a source of positive or negative pressure to move fluids within the cartridge. Port 2013 can be fluidically connected to a sample analysis sub-assembly, to convey analyte for analysis.

Turning the drum through a rotation closes and releases valves when the eccentricity engages and disengages the cam follower. In one embodiment, the eccentricities on the drum are staggered, such that during a rotation of the drum valves are closed in a pre-determined sequence. The eccentricities can be staggered, for example, by positioning the eccentricity relative to the key such that mounting the cam on the drum placed the eccentricity in a pre-selected position. One such sequence is shown in FIG. 17. The sequence is executed by one full turn of the drum, which can be turned by a stepper motor to each next position in the rotation.

Integrated System

Systems provided herein may be capable of preparing, processing and analyzing a single sample or a plurality of samples. Several operations can be performed by the system provided herein, for example, (a) receiving one or more samples; (b) isolating and extracting target material from the received sample; (c) purifying and amplifying the whole target material or selective portion of the target material to produce an analyte ready to be examined; and (d) separating, detecting and analyzing the prepared analyte. These operations can be conducted and performed in a system that comprises several integrated sub-systems, for example, a sample preparation sub-system, a sample analysis sub-system and a control-sub-system. In some cases, a system may comprise a user interface, a sample cartridge interface, and an electrophoresis interface. The sample cartridge interface and the electrophoresis interface are configured to releasably engage with a sample cartridge for sample processing, and an electrophoresis cartridge for sample analysis respectively.

Systems provided herein can be fully automated, enabling a user to receive, process and analyze a sample without substantial labor and input. Sample preparation, processing and analysis can be accomplished in provided systems without the necessity of manually removing and transferring the sample, reagents and analytes among different parts in the system. Since the incorporated sub-units (e.g., sample cartridge and electrophoresis cartridge) are highly integrated and bear small sizes, systems provided herein can be dimensioned to minimize footprint, enabling the portability and usefulness in a wide context of applications. For example, the systems may be used in on-the-go situations, such as remote locations, or they may be used in situations in which transportation is not readily available or user mobility is desired, such as battlefields scenarios and crime scenes.

The cartridges of this disclosure are useful in integrated and automated sample-to-answer systems that, starting from a sample comprising biological material, generate an analysis of the sample. In other embodiments, the cartridges can be used for stand-alone sample preparation. In certain embodiments, the biological material is DNA and the genetic profile involves determining one or a plurality of alleles at one or a plurality of loci (e.g., genetic loci) of a subject, for example, a STR (short tandem repeat) profile, for example as used in the CODIS system. The system can perform several operations, including (a) extraction and isolation of nucleic acid; (b) amplification of nucleotide sequences at selected loci (e.g., genetic loci); and (c) detection and analysis of amplification product. These operations can be carried out in a system that comprises several integrated modules, including an analyte preparation module; a detection and analysis module and a control module.

Various chemistries are commercially available to perform STR analysis and, in particular, CODIS-compatible STR analysis. These include, for example, Globalfiler® and Globalfiler® Express (6-dye, 24-locus STR kit, from Life Technologies/Thermo Fisher Scientific (Grand Island, NY) (worldwide web site: lifetechnologies.com/us/en/home/industrial/human-identification/globalfiler-str-kit.html), and PowerPlex® Fusion (e.g., PowerPlex® Fusion 6C) from Promega Corporation (Madison, WI) (worldwide web site: promega.com/Products/Genetic-Identity/STR-Analysis-for-Forensic-and-Paternity-Testing/PowerPlex-Fusion-STR-Kits?utm_medium=print&utm_source=ishi_poster&utm_campaign=powerplex&utm_content=October).

Systems provided herein may be fully integrated. Sample processing can be accomplished in a single system without having to remove a sample and transfer it to another system. Systems provided herein can be fully automated, enabling a user to process a sample without substantial input from the user.

Figure 19:
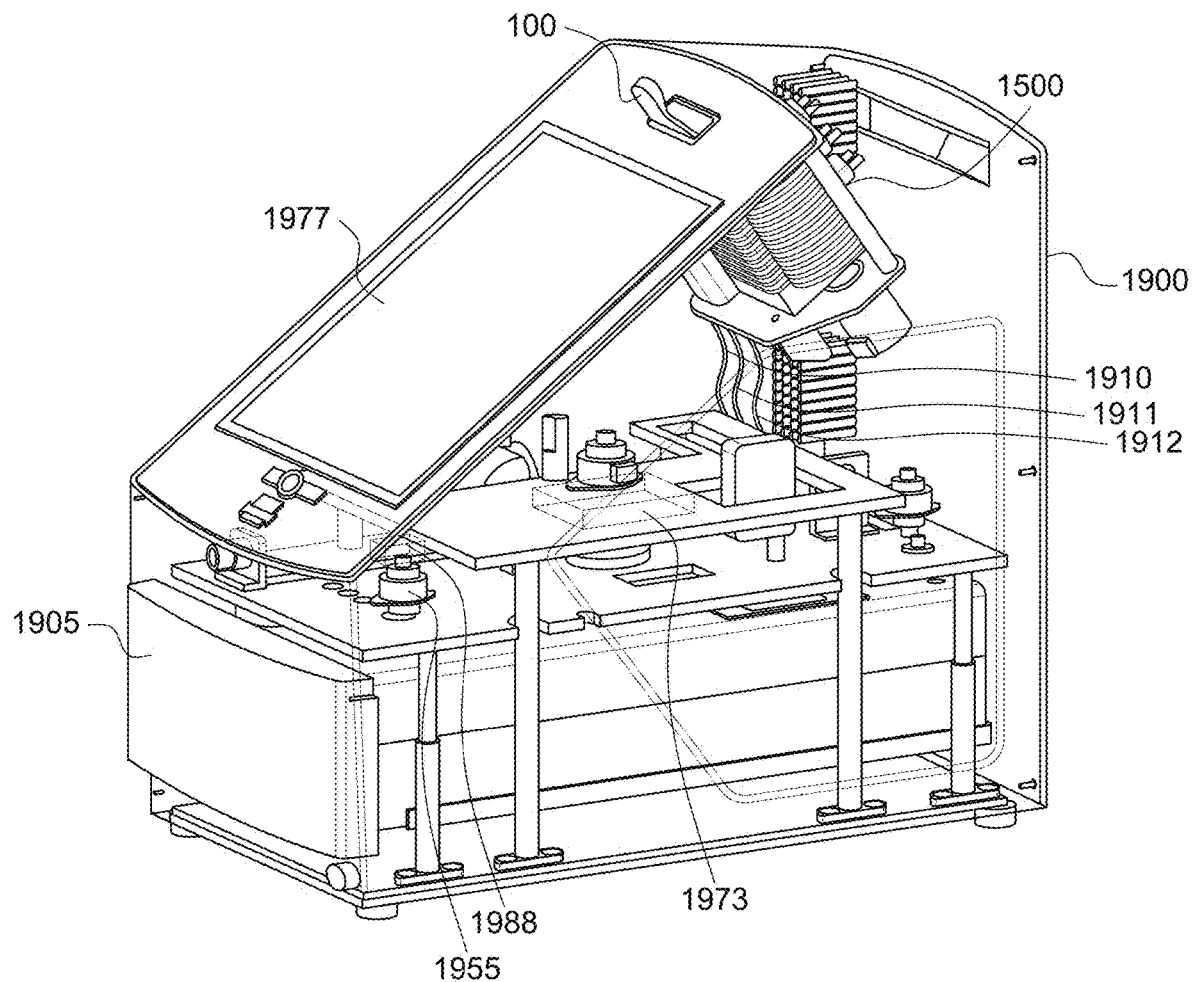
FIG. 19 shows an exemplary system of this disclosure.

FIG. 19 shows an exemplary system of this invention. System 1900 includes several functional elements. System 1900 can include a sample preparation sub-system, a sample analysis sub-system and a control sub-system. Such an instrument comprising an interface for engaging a cartridge of this disclosure, actuating valves and moving liquids is described in U.S. Provisional Patent Application Ser. No. 62/069,752, filed Oct. 28, 2014, which is incorporated herein by reference in its entirety.

A sample preparation sub-system can include a sample cartridge interface 1501 configured to engage a sample cartridge 100, sources of reagents for performing a biochemical protocol, a fluidics assembly configured to move reagents within the sample preparation sub-system. A fluidics assembly can include a pump, such as a syringe pump. The pump is fluidically connectable through valves to the outlets for reagents such as water and lysis buffer and to a source of air. The pump is configured to deliver lysis buffer and water through fluidic lines 1910 and 1911, respectively, to inlet port 1812 in the sample cartridge. Air or liquid pressure applied by the pump to inlet port 1812 can pump analyte out outlet port 1813 and through line 1912 into the analyte inlet in the electrophoresis cartridge.

A sample analysis sub-system can include an electrophoresis assembly including an anode, a cathode and an electrophoresis capillary in electric and fluidic communication with the anode and cathode, and a sample inlet communicating between a sample outlet in the sample cartridge and an inlet to the capillary. These can be contained, e.g., within an electrophoresis cartridge 1905. The sample analysis sub-system can further include an optical assembly including a source of coherent light, such as laser 1988, an optical train, including, e.g., lenses 1955, and a detector, configured to be aligned with the electrophoresis capillary and to detect an optical signal, e.g., fluorescence, therein. In this embodiment, the electrophoresis cartridge also includes a source electrophoresis separation medium and, optionally (d) sources of liquid reagents, such as water and lysis buffer, delivered through outlets in the electrophoresis cartridge to the system.

A control sub-system can include a computer 1973 programmed to operate the system. The control sub-system can include user interface 1977 that receives instructions from a user which are transmitted to the computer and displays information from the computer to the user. The user interface 1977 may be as described in U.S. Provisional Patent Application Ser. No. 62/067,429, filed Oct. 22, 2014, which is entirely incorporated herein by reference. Optionally, the control sub-system includes a communication system configured to send information to a remote server and to receive information from a remote server.

A sample preparation module includes a cartridge module assembly configured to engage and operate one or more than one sample cartridge. A sample cartridge is configured to receive one or more samples and to perform nucleic acid extraction and isolation, and DNA amplification when the cartridge is engaged with a cartridge module assembly in the system. It can also include controls and standards for assisting in analysis.

The sample preparation module can include a receptacle for receiving one or more cartridges, an engagement assembly to engage the cartridge; a fluidic manifold configured to engage ports in a cartridge and to deliver pressure and/or fluids to the cartridge through the ports; a delivery assembly configured to deliver reagents, such as amplification premix, from a compartment in the sample cartridge to an amplification compartment (e.g., plungers to push ball valves into an open position; a pneumatic manifold configured to engage ports in a cartridge and to deliver positive or negative pressure to the cartridge through the ports for moving fluids and operating valves, pumps and routers in the cartridge; a pump configured to deliver pressure to the fluidic and pneumatic manifold. Consumable reagents can be carried in a module, e.g., a buffer module, that is, removably engageable with the cartridge module.

The system also can include an interface adapted to mate with a pressure port in the cartridge and to transmit positive or negative pressure from a pressure source to the port and into the fluidic circuit. The interface can include a nozzle which the port fits. It can include a syringe for applying positive or negative pressure from another source.

PCR can be carried out using a thermal cycler assembly. This assembly can include a thermal controller, such as a Peltier device, infrared radiation source, circulating water, movement of constant temperature blocks, or other material, which can be configured to heat and cool for thermal cycling and can be comprised in the cartridge module which can be configured to move the thermal controller into thermal contact with the thermal cycling chambers, for example, through a heat spreader (or thermoconductor that can spread/distribute heat and cooling) disposed over each reaction chamber. In some embodiments, the cartridge comprises a temperature regulator assembly having one or more (e.g., a plurality) of thermocycling chambers and the sample cartridge can be in fluid communication with a fluidic channel.

An analysis and detection module is configured to receive analyte from the sample preparation module and perform capillary electrophoresis on the analyte to detect analytes separated by electrophoresis and to analyze the detected analytes. It can include a capillary electrophoresis assembly, a detection assembly, and an analysis assembly.

The capillary electrophoresis assembly can include an injection assembly, that can include a denature heater assembly, a positioning assembly for positioning an analyte for capillary injection; a cathode assembly; a capillary assembly; an anode assembly; a capillary filling assembly for filling a capillary with separation medium and a power source for applying a voltage between the anode and the cathode.

A detection assembly can comprise a laser configured to illuminate the capillaries and a detector. The laser can be configured to excite fluorescent dyes in the analyte. In alternative embodiments, the laser can be replaced by an alternate light source such as an LED. The detector can include a CCD array, CMOS array, photomultiplier, diode array, or other detector, for detecting light produced by excited dyes and for producing an output signal.

An analysis assembly can include a computer comprising memory and a processor for executing code (e.g., code on a tangible medium) for analyzing the output signal and producing a computer file containing an analysis of the signal. Such an analysis can include, for example, identification of alleles from various STR loci. The computer file can be in a format that is compatible with public databases. For example, the file can be in CODIS format which is compatible with the National DNA Index System (NDIS) operated by the FBI.

The system can be operated by a control module. The control module can include a user interface configured to receive instructions from and deliver information to a user. It can include software programmed to execute routines for performing the operations mentioned, above, and transmit and receive information, such as computer files, from remote locations, for example, over the internet.

Figure 27A:
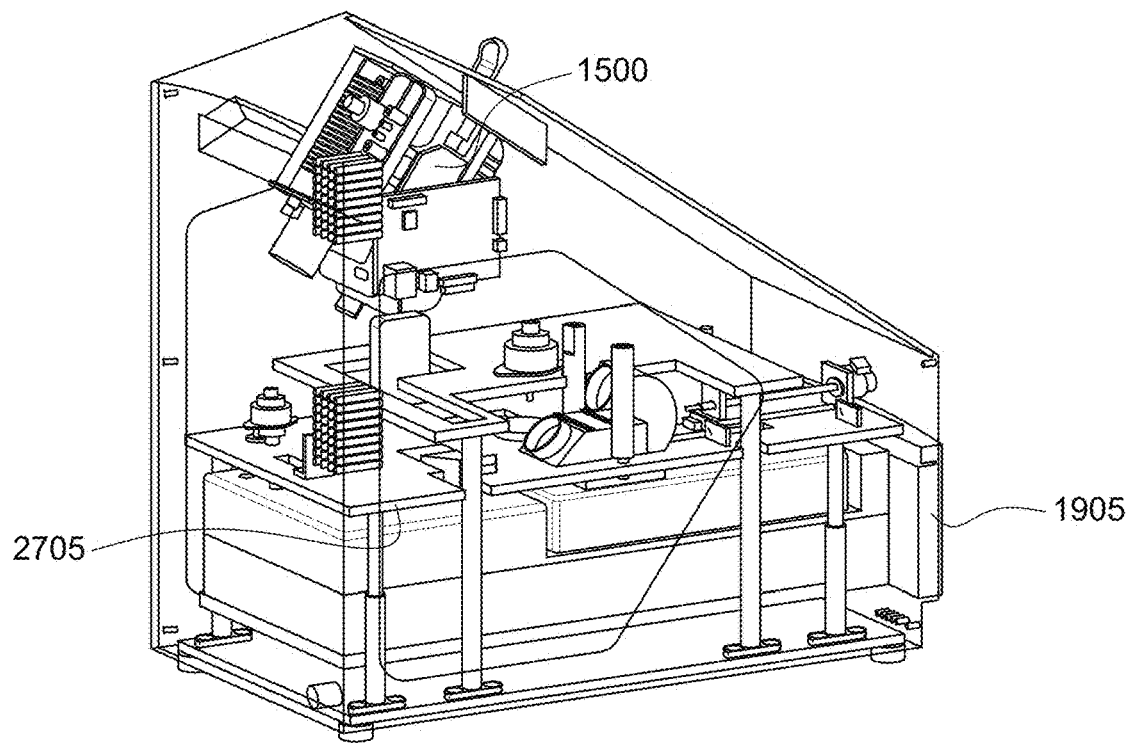
FIGS. 27A and 27B are isometric views of the system of FIG. 19.
Figure 27B:
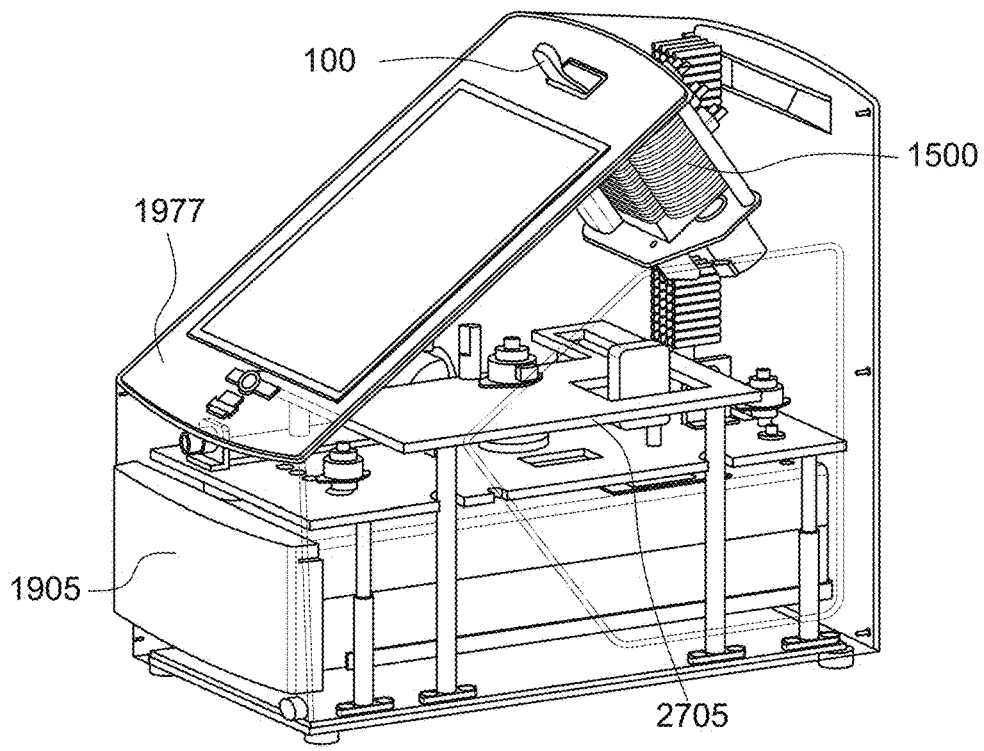

FIGS. 27A and 27B present the system of FIG. 19 in further detail. As described above and elsewhere herein, a sample cartridge interface 1500 and an electrophoresis interface 2705 are comprised in the system, for engaging the sample cartridge and the electrophoresis cartridge. Both the sample cartridge and the electrophoresis cartridge can be releasably or removably engaged with the system. The system of FIGS. 19, 27A and 27B can be used in forensic analysis to decode the genetic information of a single sample. In some cases, the system may be used to determine the genetic profile of a sample in less than about 6 hours, 5 hours, 4 hours, 3 hours, 2.5 hours, 2 hours, 1.5 hours, 1 hour, 30 minutes, 20 minutes, 10 minutes, 5 minutes 1 minute or less. Such time may depend upon, for example, the number of steps included in sample processing operations.

Figure 28:
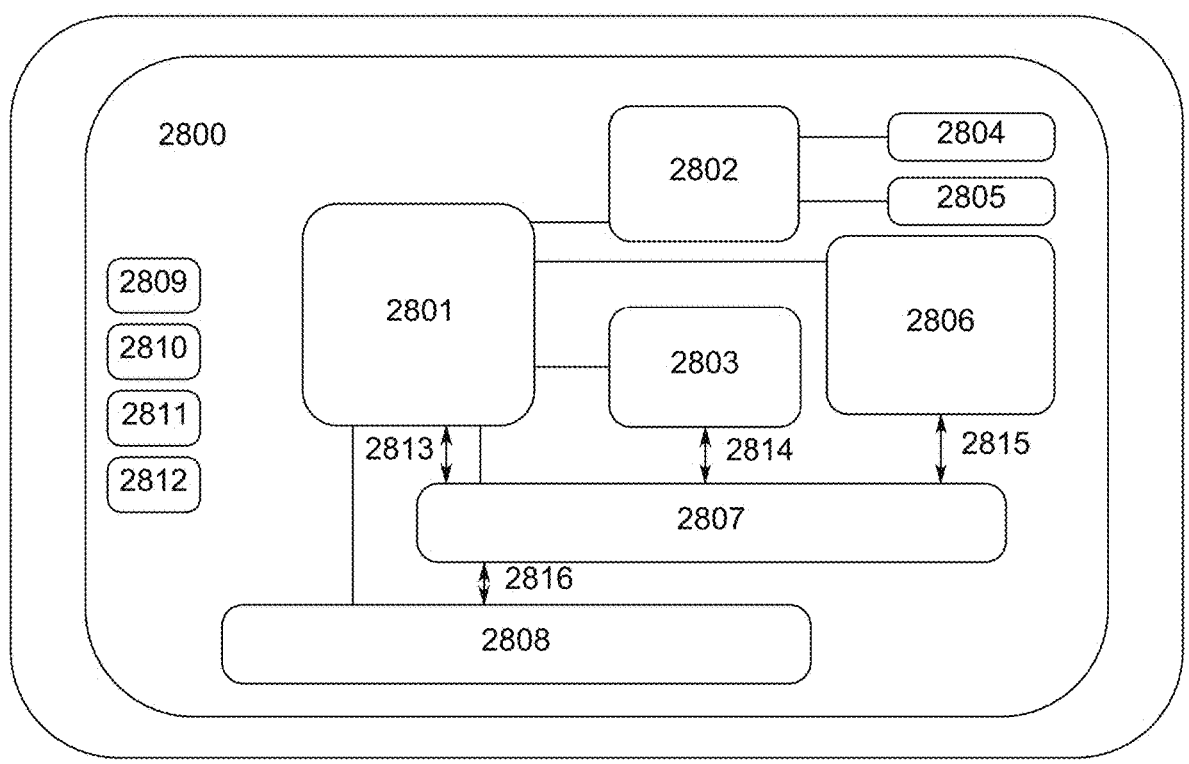
FIG. 28 shows a schematic of an example electrophoresis cartridge-comprising system.

A schematic of the system of FIGS. 19, 27A and 27B is illustrated in FIG. 28. A chassis 2800 is included for structural support, which may be formed of a metallic material, such as aluminum or steel, a polymeric material, or a combination thereof. In some cases, the chassis may be structured to minimize the weight of the system. A user interface which comprises system electronic controls 2801, embedded computer 2802, and a user interface screen capable of identifying and reading fingerprint 2804 and sample patch barcode 2805, is included in the system. The user interface receives and processes requests or instructions from and delivers information to a user. It can include software programmed to execute routines for performing the operations mentioned, above, and transmit and receive information, such as computer files, from remote locations, e.g., over the internet. The user interface can also enable the user to monitor the progress of the operation and make changes to the operation of system if measurements are not within selected parameters. A sample cartridge interface 2806 is provided for receiving a sample cartridge for sample processing. The sample cartridge described herein can be configured to receive one or more samples and to perform at least one of sample isolation, extraction, purification, amplification or dilution, when the sample cartridge is engaged with the sample cartridge interface of the system. Sample amplification can include polymerase chain reaction (PCR). One or more reagents that are needed for performing one or more steps of sample processing may be pre-loaded or comprised in the sample cartridge, for example, washing buffer, lysis buffer, diluent, amplification reagents, or internal lane standards. Also comprised in the system is a fully integrated electrophoresis cartridge 2807 which is releasably engageable with the system via an electrophoresis cartridge interface. The electrophoresis system comprises all essential parts for performing an electrophoretic analysis, such as an electrophoresis capillary, electrodes (e.g., anode and cathode), electrophoresis separation medium, or electrophoresis buffer. In some cases, it may comprise reagent that can be used to perform STR analysis. It may further comprise one or more reagent container for holding reagents that are used for sample processing, e.g., a lysis buffer container. The lysis buffer may be placed in fluidic communication with the sample cartridge and used for isolating the target material out of the sample during sample processing, after both the sample cartridge and the electrophoresis cartridge are engaged with the system. Once the engagement of the electrophoresis cartridge is completed, at least one automatic communication between the electrophoresis cartridge and the system may be established, for example, an electrical communication 2813 between the electrophoresis cartridge and the system electronic controls 2801, an optical communication 2814 between a portion of the electrophoresis capillary in the electrophoresis cartridge and an optics module 2803 of the system, a fluidic communication 2815 between a sample inlet port of the electrophoresis cartridge and a sample outlet port of the sample cartridge, a mechanical and thermal 2816 communication between the electrophoresis cartridge and a motorized drives and cooling module 2808 of the system.

In one example, the integrated electrophoresis cartridge 2807 has all or substantially all of the components necessary for electrophoresis in a compact unit that is readily insertable into and removable from the electrophoresis cartridge interface. This may permit a user to readily engage the cartridge 2807 with the system without having to open the system. In some examples, all or substantially all of the components necessary for electrophoresis (e.g., anode, cathode and at least one electrophoresis capillary are included on a single board or support or multiple boards or supports that are securably integrated with one another.

The system provided herein may further comprise a power source 2812 for supplying the power for the system, AC power source 2811 for applying a voltage gradient across the anode and the cathode, one or more fans 2810 for dissipate the heat for one or more parts of the system, and one or more USB ports 2809 for collecting and transferring data either within the system or outside the system.

Figure 29:
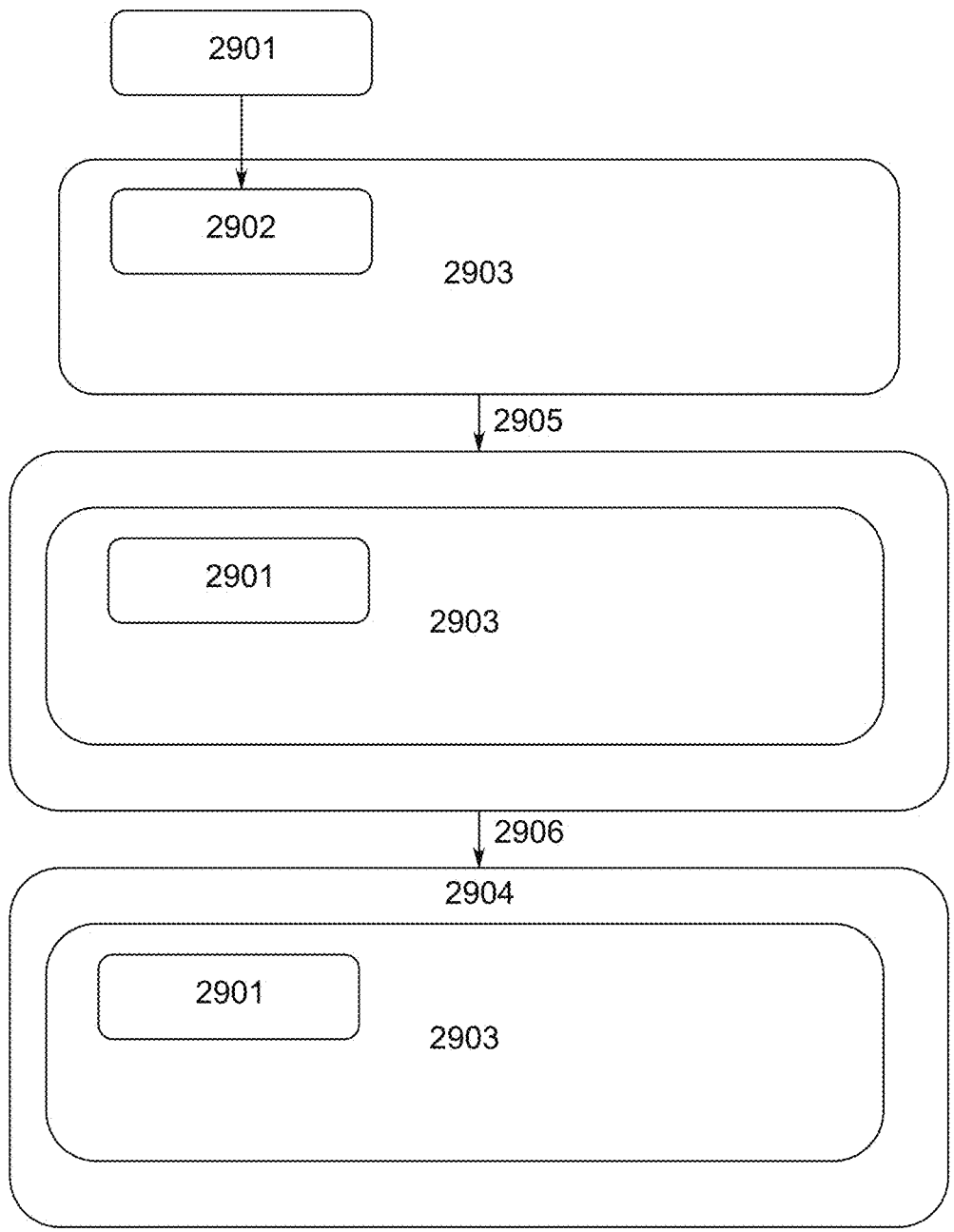
FIG. 29 schematically illustrates an example system engaging an electrophoresis cartridge.

Also provided herein, the electrophoresis cartridge may comprise one or more of sub-containers or sub-cartridges that are removably insertable in the electrophoresis cartridge, such as, sub-containers for holding electrophoresis separation medium, reagents for sample processing, or reagents for sample analysis. FIG. 29 shows an example of an electrophoresis cartridge comprising an electrophoresis separation medium sub-container. As shown in FIG. 29, an electrophoresis cartridge is manufactured to have a space 2902 configured to specifically receive and accommodate a secondary or sub-container. A sub-container 2901 used for holding the electrophoresis separation medium can be stored outside the electrophoresis cartridge 2903 before the engagement of the electrophoresis cartridge with the system. The sub-container which holds the electrophoresis separation medium may be installed 2905 into the electrophoresis cartridge a short time before the engagement of the electrophoresis cartridge with the system, for example, less than 1 hour, 50 minutes, 40 minutes, 30 minutes, 20 minutes, 15 minutes, 10 minutes, 5 minutes before engaging the electrophoresis cartridge with the system. Once the electrophoresis cartridge is installed 2906 into the system, the sub-container may be placed in thermal communication with a thermal control module of the system, which may adjust the temperature of the sub-container to a desired value and maintain it for a period of time.

Figure 30A:
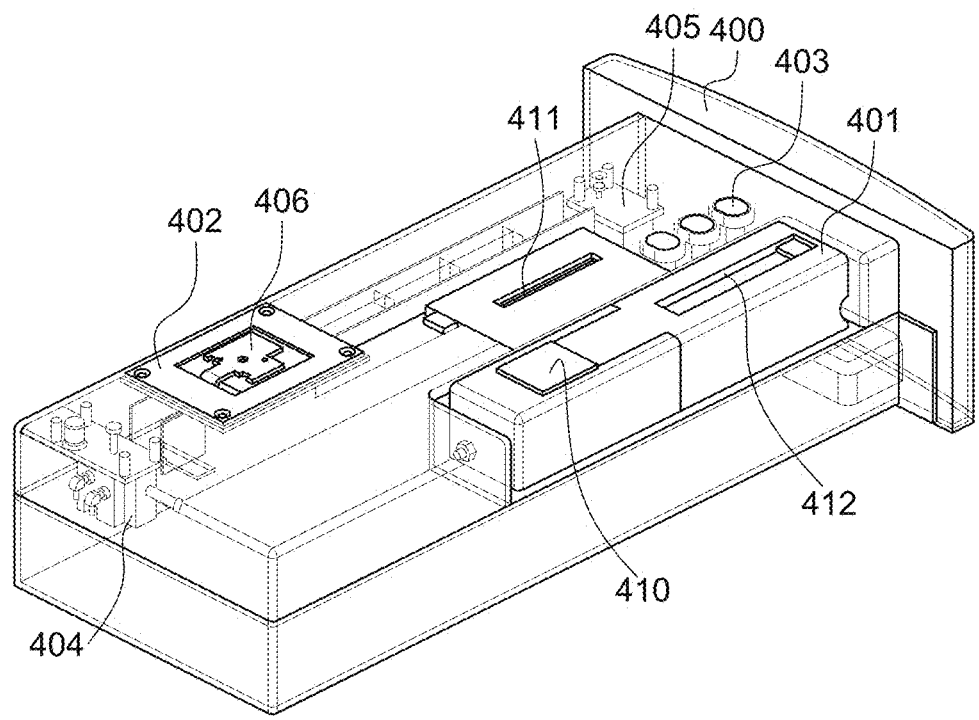
FIGS. 30A and 30B are isometric view of an example electrophoresis cartridge.
Figure 30B:
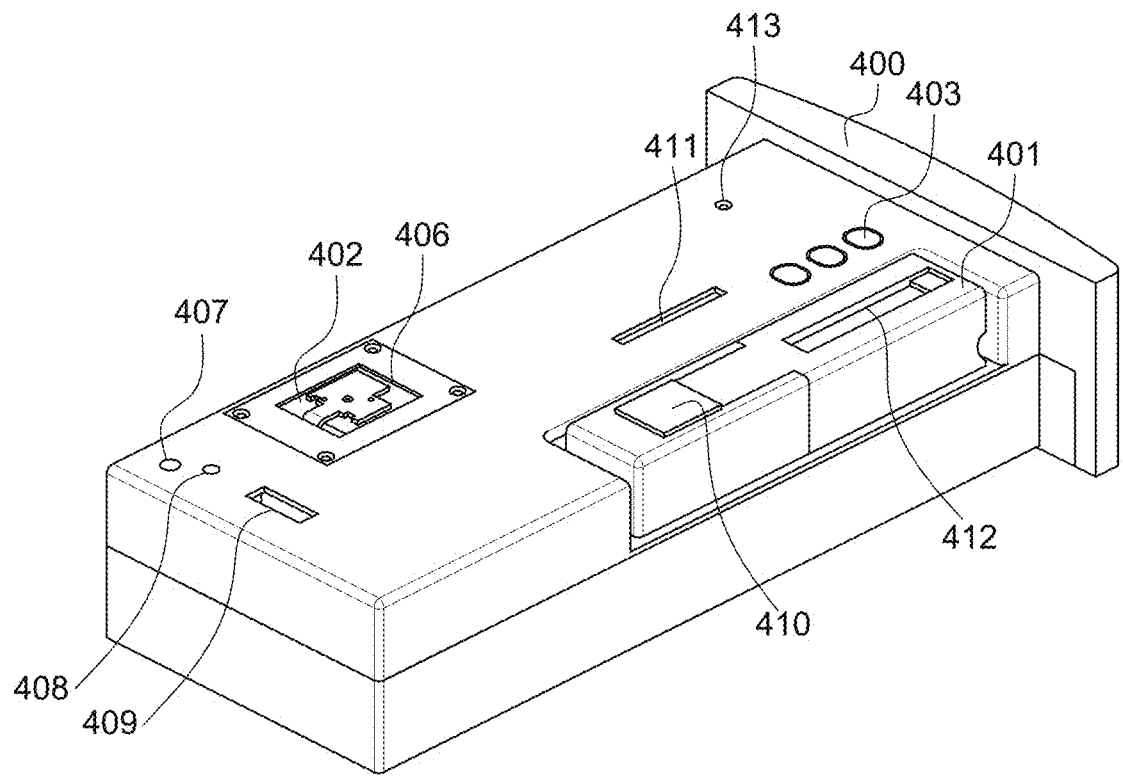

FIGS. 30A and 30B show clear shell views of an example electrophoresis cartridge of the present disclosure. In general, the electrophoresis cartridge may comprise a cartridge casing 400, a sub-container (or sub-cartridge) casing 401, an optical interface 402 for providing a light source and detecting signals from analytes, one or more hydrodynamic devices (e.g., fluid coupling) 403, an anode sub-assembly 404, a cathode sub-assembly 405, an electrophoresis capillary 406, an electrical interface 407, one or more mechanical interfaces (e.g., 408, 409, 412 and 413) for applying pressure or forces on parts of the electrophoresis cartridge, a thermal interface 410 for control the temperature of the sub-container 401, and an electrical interface 411 for providing a voltage between at least one anode in the anode sub-assembly and at least one cathode in the cathode sub-assembly.

Figure 31:
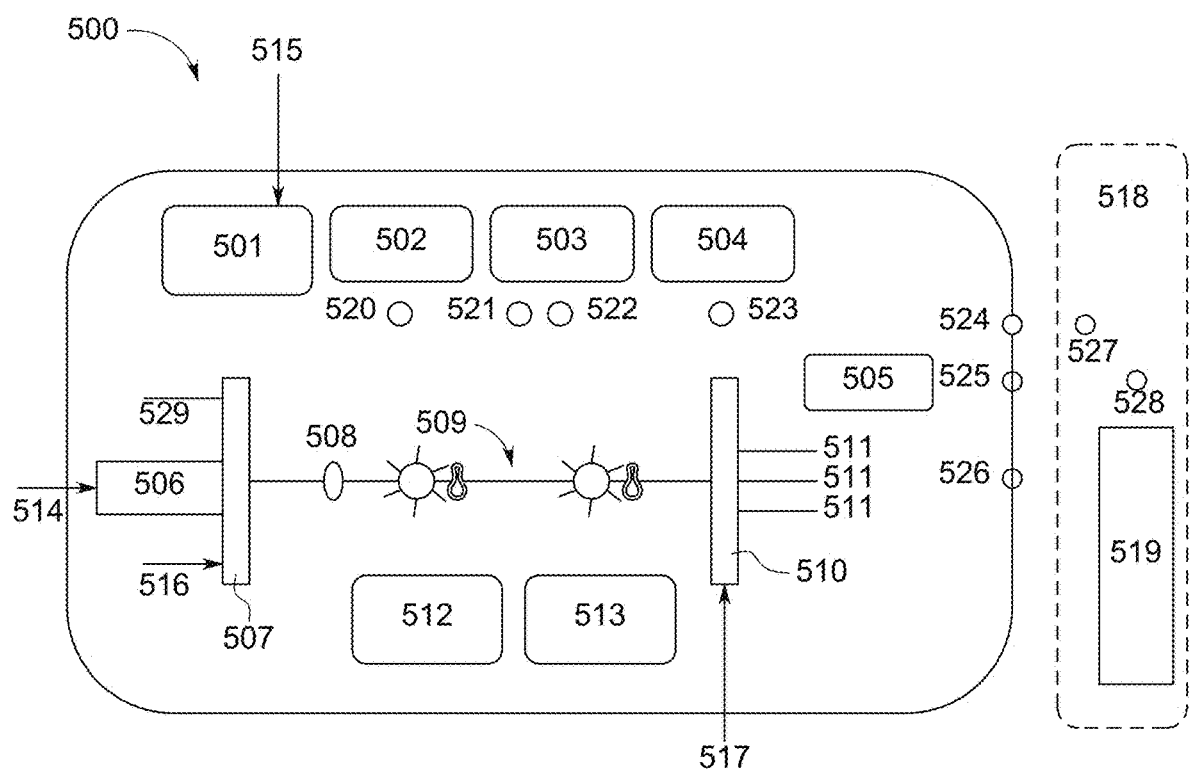
FIG. 31 shows a schematic of an example electrophoresis cartridge.

A schematic of an example electrophoresis cartridge 500 is shown in FIG. 31. The electrophoresis cartridge 500 may comprise an electrophoresis assembly which includes an anode sub-assembly 507, a cathode sub-assembly 510, and at least one electrophoresis capillary 509 to be used in sample separation and analysis for at least one sample.

As shown in FIG. 31, three cathode nodes 511 can be included in the cathode sub-assembly and in fluidic and electrical communication with a first end of the electrophoresis capillary. At least one anode node 529 is comprised in the anode sub-assembly and in fluidic and electrical communication with a second end of the electrophoresis capillary. Although presented in the present disclosure are an anode sub-assembly and a cathode sub-assembly comprising one anode node and three cathode nodes, it shall be appreciated that any positive number of anodes and cathodes may be used, dependent upon, different applications.

The electrophoresis cartridge may also comprise more than one container for holding electrophoresis separation medium and more than one reagent for sample processing and analysis. As shown in FIG. 31, an electrophoresis separation medium container 501, a first reagent container 502, a second reagent container 503, a third reagent container 504, and a fourth reagent container 505 are included in the electrophoresis cartridge 500. The containers may be configured to be removably insertable into the electrophoresis cartridge. After each run of sample analysis, one or more containers may be replaced or reused, depending upon, the applications. In some cases, it may be desirable to store or transport one or more containers at a pre-determined temperature, for example, if a thermal-sensitive electrophoresis separation medium or electrophoresis reagent is used and the trivial change of temperature may impair its performance and thereafter result in the degradation or failure of the whole analysis. Once the containers are installed in the electrophoresis cartridge, they may be kept at the same or a different temperature. Installation of the containers may be realized manually or automatically.

Once the electrophoresis separation medium container 501 is properly engaged with the electrophoresis cartridge, with the aid of a first mechanical interface 515 for controlling one or more fluid handling devices (e.g., a pump), the electrophoresis separation medium may be driven and moved into the anode sub-assembly 507. The electrophoresis separation medium may be further pushed into at least one of the electrophoresis capillary with the application of a second and a third mechanical interface 514 and 516 by exerting a force (or pressure) on a high pressure piston 506 and an anode main piston (not shown).

Any suitable reagent may be used in the present disclosure. Reagents may be solid, semi-solid or liquid. In cases where liquid reagents are used, they may comprise organic fluid, inorganic fluid, or a mixture thereof. For example, reagents may comprise water, electrophoresis buffer, sample processing buffer (e.g., a lysis buffer), loading buffer, regeneration fluid, or combinations thereof. For example, reagents can be provided (e.g., stored) in an aqueous solution, or can be provided (e.g., stored) in a solid or dry (e.g., lyophilized) form and then placed into solution by addition of a liquid (e.g., an aqueous solution) as appropriate. Alternatively, reagents can be provided (e.g., stored) in a substantially water-free non-ionic organic solvent (e.g., an alcohol solvent) or in a substantially water-free ionic organic solvent (e.g., a deep eutectic solvent) and can be re-hydrated by addition of an aqueous solution as appropriate, as described in PCT Patent Publication No. WO 2014/055936, which is entirely incorporated herein by reference. As used in the present disclosure, the term "regeneration fluid" generally refers to a fluid that is able to renew or restore the function or performance of one or more parts of the electrophoresis cartridge, for example, the electrophoresis capillary. In some cases, the regeneration fluid may comprise an aqueous solution. In some cases, the regeneration fluid may comprise an alkaline fluid. In some cases, the regeneration fluid may comprise one or more alkali hydroxides.

To collect any liquid or fluid from, for example, an electrophoresis capillary, the anode sub-assembly, or the cathode sub-assembly, two waste containers 512 and 513 may be included in the electrophoresis cartridge and communicate with the anode-subassembly and the cathode sub-assembly, respectively. Any number of waste containers (e.g., at least 1, 2, 3, 4, or 5) may be included in the electrophoresis cartridge, as provided in the present disclosure. For example, besides the waste containers that are in communication with the anode sub-assembly and cathode sub-assembly, each of the reagent containers and the electrophoresis separation medium container may be provided with its water container.

In some aspects of the present disclosure, the electrophoresis cartridge may further comprise a plurality of fluid handling devices which place various parts or components of the electrophoresis cartridge in fluidic communication. As described above and elsewhere herein, any type of devices that is capable of moving or transferring the fluid may be used, such as valves, pumps, electrostatic fluid accelerators, and various other forms of process equipment. As shown in FIG. 31, pumps 520 and 521 are used to drive the reagents stored in the first and the second reagent containers 502 and 503 to the anode sub-assembly 507, through their respective fluid conduits. Similarly, pumps 522 and 523 are utilized to transfer the reagents kept in the second and the third reagent containers 503 and 504 to the cathode sub-assembly 510, through two separate fluid conduits.

In some cases, it may be desirable that at least one of the reagent containers communicate with more than one part of the electrophoresis cartridge or the system. For example, as illustrated in FIG. 31, the second and the third reagent containers 503 and 504 are placed in communication with parts outside of the electrophoresis cartridge, besides their communication with the cathode sub-assembly 510 of the electrophoresis cartridge as described above. In detail, both of the reagent containers are in fluidic communication with the sample cartridge interface 519 and a fluid handling device 518 through a fluid line. A four-port valve 528 and a three-port valve 527 are utilized to direct, control and regulate different types of fluid flow in the fluid line. Alternatively or additionally, it may be advantageous to have one or more reagent containers installed inside the electrophoresis cartridge which communicate directly with parts or components which are outside of the electrophoresis cartridge. For example, in the present example as shown in FIG. 31, a fourth reagent container 505 is engaged with the electrophoresis cartridge and placed in fluidic communication with the sample cartridge interface 519 through a fluid line. In some cases, one or more hydrodynamic devices (e.g., fluid couplings 524, 525 and 526) may be included in the electrophoresis cartridge which may aid in delivering and transferring the reagents, analytes or samples through the fluid line.

The electrophoresis cartridge may also comprise a sample delivery assembly comprising at least one sample inlet port and at least one sample line, with each sample line placing a sample inlet port in communication with the first end of the electrophoresis capillary through a passage in the cathode sub-assembly. The sample inlet port may be further configured to communicate with a sample outlet port comprised in a sample cartridge interface 519, via a hydrodynamic device 526, for example, a fluid coupling or a hydraulic coupling. With the sample delivery assembly, the processed sample from a sample cartridge that is engaged with the sample cartridge interface may be directed to a separation channel (e.g., an electrophoresis capillary) via the sample line. Any suitable method for moving the prepared sample into the separation channel may be used in the context of the present disclosure. For example, field-amplified stacking (FAS) may be performed by positioning in an electrophoresis sample line a diluted mixture comprising the sample of lower salt concentration or lower ionic strength than used in the separation gel. In another example, a bolus of a material (e.g., air) can be positioned downstream of the sample in the sample line, wherein the material has an electrical conductivity that differs from the electrical conductivity of the electrophoresis buffer or the sample. When the sample is positioned across the separation channel, the sample can be electrokinetically injected into the separation channel at an appropriate voltage (e.g., about 3 kV to about 5 kV, or about 4 kV) over an appropriate amount of time (e.g., about 10 sec to about 20 sec, or about 15 sec). In some other examples, a pump may be used to drive the sample into the separation channel.

Once the prepared sample is moved into the separation channel, the sample may then be subjected to sample separation and analysis within the separation channel, with the aid of an electric field, as can be generated upon the application of a voltage gradient across the anode 529 and the cathode 511. Upon the effect of the electric field, analytes in the electrophoresis capillary move through the matrix (i.e., electrophoresis separation medium) at different rates, determined by one or more factors, such as mass, charge, or a combination thereof.

A portion of the electrophoresis capillary can be used as an optical window 508 which is capable of receiving a light from a light source and emitting signals that can be captured and detected by one or more detectors included in a detection assembly. In some cases, an optics module may be provided, which may comprise both the light source and the detection assembly. The light source is positioned to deliver a beam to at least one electrophoresis capillary via the optical window. One or more optical detectors (e.g., charge-coupled device (CCD), complementary metal-oxide-semiconductor (CMOS), photodetector, photo diode, or photomultiplier detector) may be optically coupled to receive signals emitted from at least one electrophoresis capillary through the optical window. As discussed elsewhere in the present disclosure, the optical communication between the optical window in the electrophoresis cartridge and both the light source and the optics module may be automatically established at the same time as the occurrence of the engagement of the electrophoresis cartridge.

The capillary can be heated to maintain an appropriate running temperature. The capillary can be heated by, for example, flowing temperature-controlled air over the capillary, by placing the capillary in thermal contact with a thermoelectric heater (e.g., a Peltier), or by placing the capillary in thermal contact with a resistive heater. An example of an assembly using a resistive heater to heat a capillary is described in U.S. Pat. No. 8,512,538. In another embodiment, a capillary heater assembly can comprise a flexible heater circuit comprising a resistive heater (e.g., a wire trace) in a polymeric substrate. Such flexible heater circuits are commercially available from Mod-Tronic (Thermofoil®), Kapton (polyimide heater) and McMaster-Carr (ultrathin heat sheet).

Method of Use

The cartridges of this disclosure can be used in an integrated system for preparing a sample, for example, DNA isolation and amplification. For example, in one embodiment, a sample contained on for example a swab or a card punch, can be introduced into sample chamber 120. The cartridge can be engaged with cartridge interface 901. Cell lysis buffer contained in an off-chip reservoir can be feed through port 112 into the fluidic channel in the cartridge and into the sample chamber 120 by closing valves 141, 142, 143, and 147. Port 112 can be connected to a syringe or to another source of positive or negative pressure. After lysis, lysate can be moved through a fluidic channel on the cartridge, for example, with a plunger that applied vacuum through port 112 to draw the fluid into reaction chamber 122 by opening valves 147, 148, 149, and 142; and closing valves 146, 145, 143, 144, and 141. In one embodiment, the DNA reaction chamber can include material that captures a pre-determined amount of analyte. Excess fluid can be moved into waste chamber 123 while the reaction chamber is filled. Reagents for performing PCR or other reactions can be introduced into the reaction chamber through ports 115 and 116. In one embodiment, as detailed in US Patent application US 2013/0115607 and International Patent Application WO 2013/130910, an actuator pushes on ball valves, e.g., 803, to push the master mix in port 115 and the primers in port 116 into reaction chamber 122. A thermal control mechanism in the system can apply heat to perform thermal cycling in reaction chamber 122 of the cartridge with valves 148 and 149 closed. Following thermal cycling, valves 148, 145, 143 and 141 are opened and valves 149, 146, 147, 144, 142 are closed, and internal lane standard is dispensed from port 114 into reaction chamber 122 and pushed into mix chamber 121. Following mixing, valves 141, 142, 145, 146 are closed; valves 143 and 144 are opened and the amplified STR mixture with internal lane standard is pushed to through port 113 to a capillary electrophoresis analysis module for separation, detection, and analysis.

A. Amplification and Cycle Sequencing—One Channel

In another embodiment, cartridges of this disclosure can be used to perform DNA amplification and subsequent preparation for cycle sequencing. The target for sequencing can be, for example, a diagnostic target, such as a gene for genotyping, a polynucleotide bearing a somatic mutation, e.g., from a tumor, or a polynucleotide from an infectious microorganism such as a bacterium or a virus.

Figure 21:
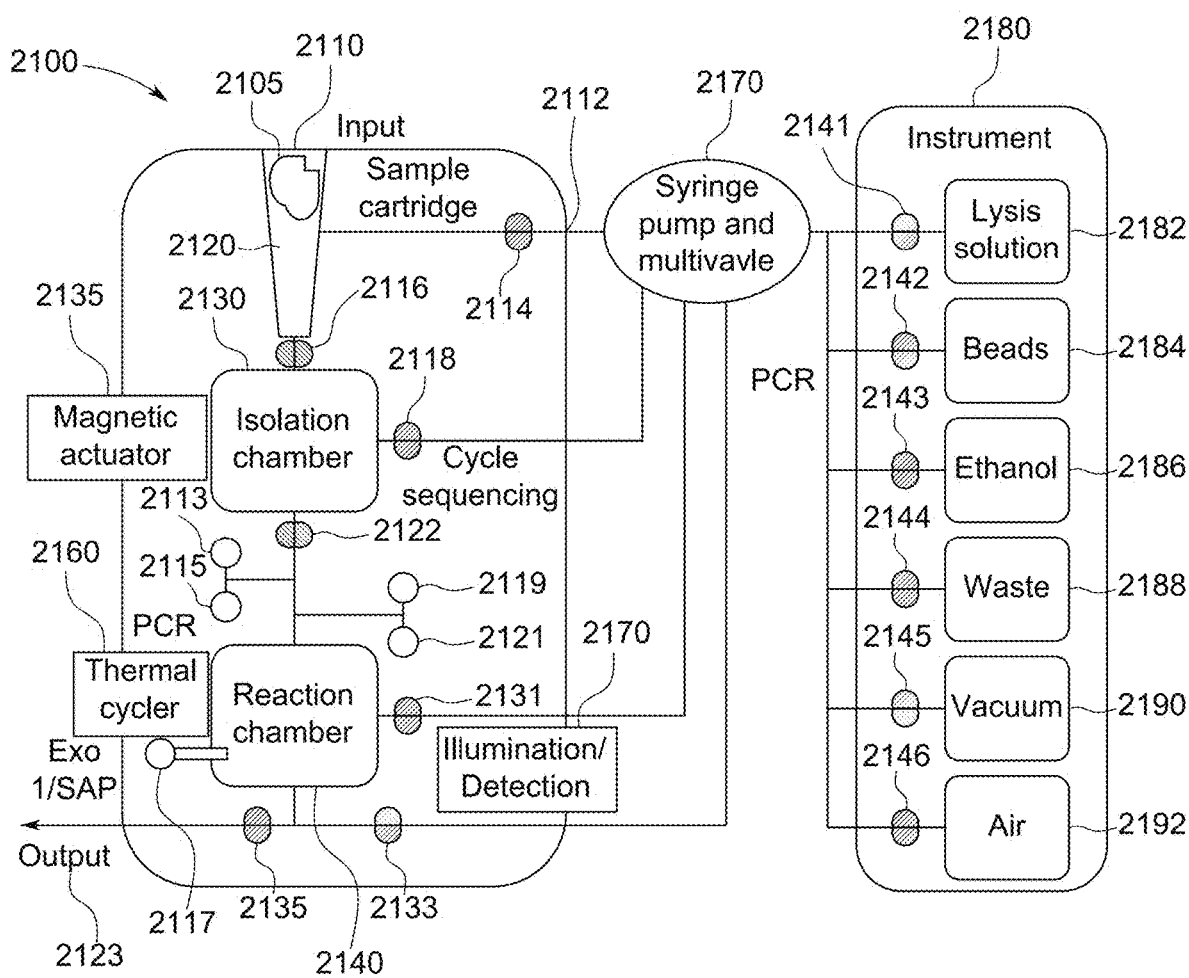
FIG. 21 shows an exemplary cartridge configuration of this disclosure.

An exemplary cartridge 2100 for such an embodiment is shown in FIG. 21. Cartridge 2100 has input 2110. A sample 2105 can be introduced into sample chamber 2120. The cartridge can be engaged with an interface of instrument 2180 configured to supply reagents and motive forces. Cell lysis buffer contained in an off-chip reservoir 2182 can be fed through port 2112 into a fluidic channel in the cartridge and into the sample chamber 2120 by opening valve 2114. Port 2112 can be connected to a syringe 2170 or to another source of positive or negative pressure.

After lysis, lysate can be moved through a fluidic channel on the cartridge into isolation chamber 2130 by opening valve 2116; if required vacuum can be applied by syringe 2170 by opening valve 2118. Magnetically responsive particles, e.g., beads 2184, can be introduced into the isolation chamber before or after introduction of the lysate by opening valve 2118. In another embodiment, the beads can be preloaded into isolation chamber 2130. Polynucleotides can be captured on the particles and immobilized by application of a magnetic force to the isolation chamber 2130 by magnetic actuator 2135. The particles can be washed with, e.g., ethanol 2186, and the wash moved to a waste chamber on cartridge (not shown) or off-cartridge 2188.

Then the polynucleotides can be moved into a reaction chamber 2140 for PCR by opening valve 2122. Reagents for amplifying a specific nucleotide sequence can be introduced into the reaction chamber from sealed compartments through ports 2113 and 2115 or these sealed compartments can contain the reagents in an integrated vial with seals by for example Teflon balls. These include primers, nucleotides, and hot start DNA polymerase. Primers are typically kept separate in a "primer mix" from the other ingredients, mixed as "master mix". A thermal control mechanism in the system, e.g., thermal cycler 2160, can apply heat to perform thermal cycling in reaction chamber 2140 of the cartridge. Following thermal cycling, remaining primers and nucleotide triphosphates can be degraded by adding, for example, exonuclease I and shrimp alkaline phosphatase from a sealed compartment through port 2117. Following reaction, the exonuclease I and shrimp alkaline phosphatase can be degraded by heating to 80 C. by thermal cycler 2160.

Reagents for performing cycle sequencing can then be introduced into the reaction chamber, for example, from sealed compartments on the cartridge through ports 2119 and 2121. These include a sequencing primer, nucleotides, hot start DNA polymerase, and labeled dideoxynucleotides (e.g. BigDye® terminators form Life Technologies®) for dye terminator sequencing. Primers are typically kept separate in a "primer mix" from the other ingredients, mixed as "master mix". Thermal cycling produces dideoxynucleotide-terminated polynucleotides with base specific fluorescent label.

This mixture can then be moved back into isolation chamber 2130. Magnetically responsive particles can be introduced into isolation chamber 2130 for polynucleotide capture and clean up.

Cleaned up polynucleotides can then be pushed, e.g., with air 2192 through output port 2123 to a capillary electrophoresis analysis module for separation, detection, and analysis.

In alternative embodiments, some or all reagents are stored in compartments on the cartridge for movement into the fluidic circuit as needed.

Figure 32A:
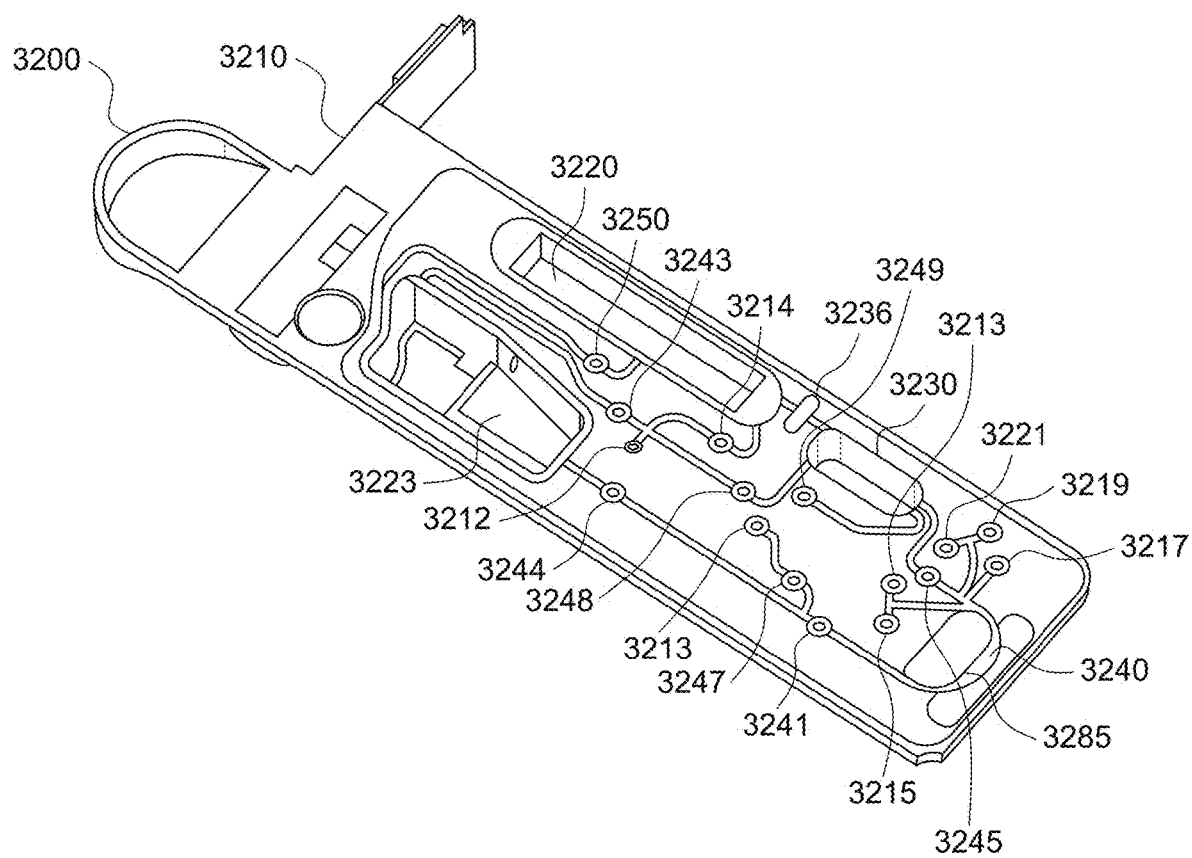
FIG. 32A shows a circuit face of an exemplary cartridge of this disclosure.
Figure 32B:
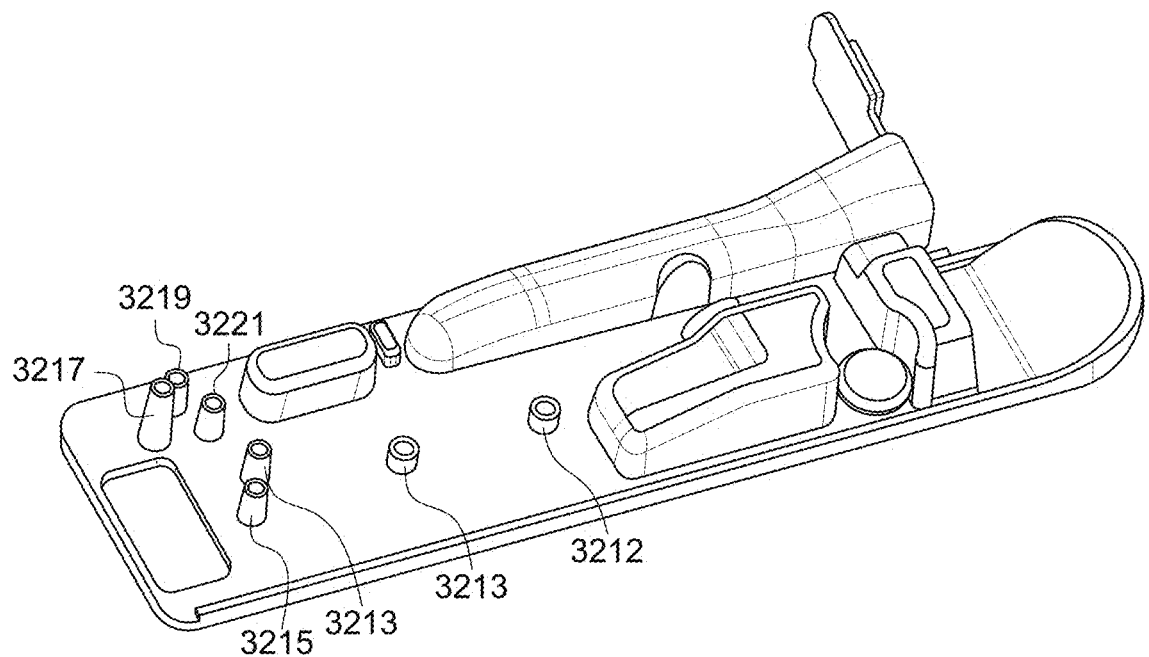
FIG. 32B shows an external view of an exemplary cartridge configuration of this disclosure.

Another embodiment of a cartridge configured to perform this method is depicted in FIGS. 32A and 32B. Cartridge 3200 includes inlet 3210, pressure port 3212, lysis chamber 3220, filter chamber 3236, isolation chamber 3230, reaction chamber 3240, magnetically attractable beads 3285 in the reaction chamber, ports 3213 and 3215 for PCR reagents, ports 3219 and 3221 for cycle sequencing reagents, exit port 3213, and valves 3213, 3214, 3241, 3243, 3244, 3245, 3248, 3249 and 3250. The cartridge aspect in FIG. 32B shows ports 3212 and 3213, as well as open compartments for ports 3213, 3215, 3217, 3219 and 3221.

B. Amplification and Cycle Sequencing—Multi-Channel

In an alternative embodiment, a cartridge of this disclosure has a fluidic circuit with a plurality of branches, each branch adapted to perform a separate biochemical reaction. For example, each of two branches can be used to perform one of forward and reverse strand cycle sequencing on a sample. The forward strand can be prepared for sequencing in a first branch and the reverse strand can be prepared for sequencing in a second branch. Alternatively, different branches can be used to amplify different target nucleotide sequences from the same sample.

Figure 22:
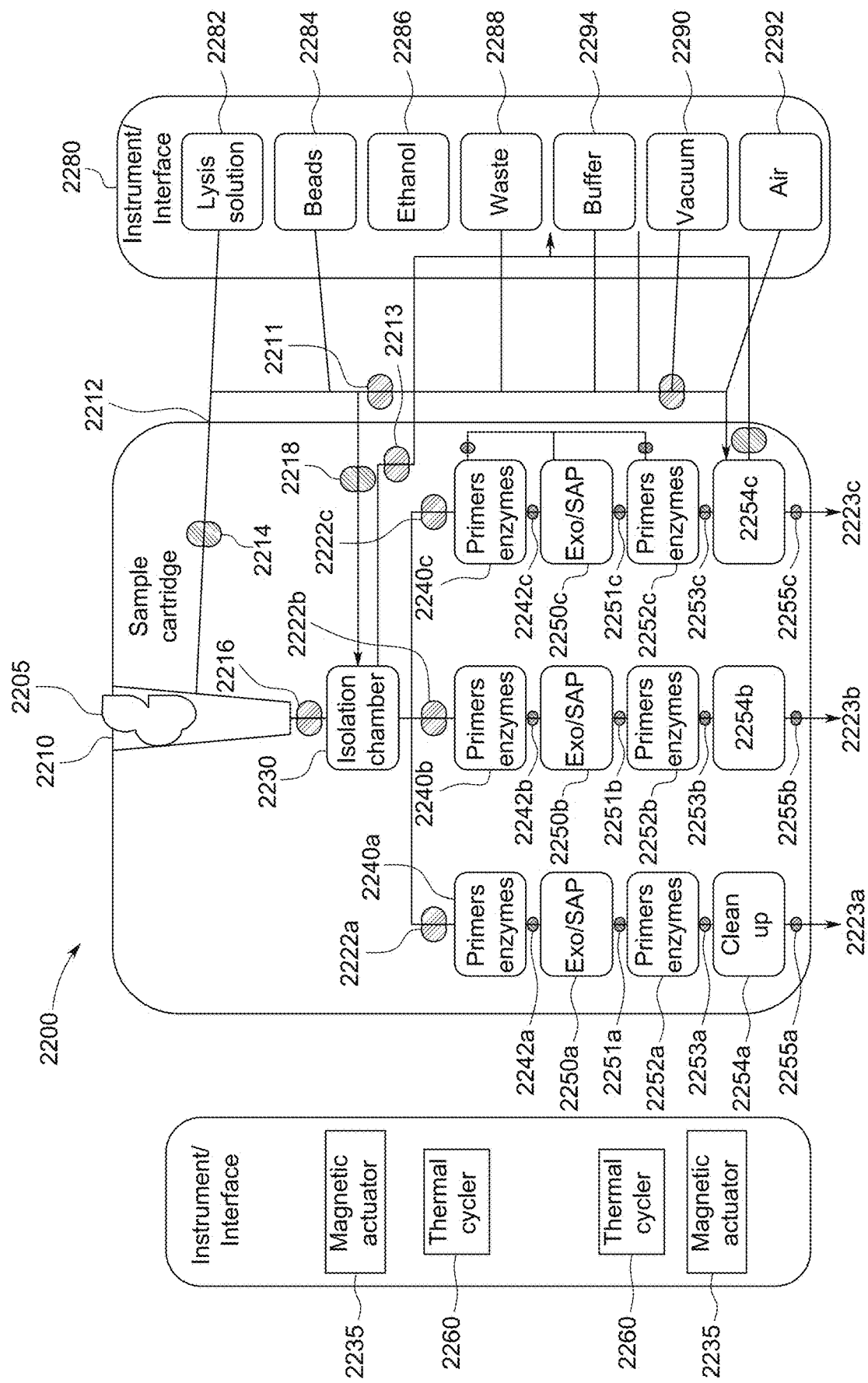
FIG. 22 shows an exemplary cartridge configuration having a circuit with three branches.

An exemplary cartridge 2200 for such an embodiment is shown in FIG. 22. Cartridge 2200 has input 2210. A sample 2205 can be introduced into sample chamber 2220. The cartridge can be engaged with an interface of instrument 2280 configured to supply reagents and motive forces. Cell lysis buffer contained in an off-chip reservoir 2282 can be fed through port 2212 into a fluidic channel in the cartridge and into the sample chamber 2220 by opening valve 2214. The lysis solution can be compatible with particles used to capture polynucleotides. Port 2212 can be connected to a syringe or to another source of positive or negative pressure.

After lysis, lysate can be moved through a fluidic channel on the cartridge into isolation chamber 2230 by opening valve 2216. Magnetically responsive particles, e.g., beads 2284, can be introduced into the isolation chamber before or after introduction of the lysate by opening valve 2218. Polynucleotides can be captured on the particles and immobilized by application of a magnetic force to the isolation chamber 2230 by magnetic actuator 2235. The particles can be washed with, e.g., ethanol 2286, and the wash moved to a waste chamber or off-cartridge 2288.

Then, aliquots of the polynucleotides can be moved into reaction chambers 2240a-c for PCR by opening valves 2222a-c. This can be done, for example, by opening and closing these valves sequentially, and moving material into each open chamber. Reagents for amplifying a specific nucleotide sequence can be introduced into the reaction chamber from sealed compartments or may be present in lyophilized form. A thermal control mechanism in the system, e.g., thermal cycler 2260, can apply heat to perform thermal cycling in reaction chamber 2240 of the cartridge.

Following thermal cycling, the products can be moved into chambers 2250a-c by opening valves 2242a-c. Here, primers and nucleotide triphosphates are degraded by, for example, exonuclease I and shrimp alkaline phosphatase present in lyophilized form or added from a sealed compartment. Following reaction, the exonuclease I and shrimp alkaline phosphatase can be degraded by heating to 80 C. by thermal cycler 2260.

The samples are then moved into reaction chambers 2250a-c by opening valves 2251a-c for preparation for cycle sequencing. Again, reagents for performing cycle sequencing can be introduced into the reaction chamber, for example, from sealed compartments on the cartridge or may be present in lyophilized form. Thermal cycling produces dideoxynucleotide-terminated polynucleotides with base specific labels.

The product of the thermal cycling reactions is then moved into clean-up chambers 2254a-c by opening valves 2253a-c. Magnetically responsive particles can be introduced into clean-up chambers 2254a-c for polynucleotide capture and clean up.

Cleaned up polynucleotides can then be pushed, e.g., with air 2292 through output ports 2223a-c by opening valves 2255a-c to a capillary electrophoresis analysis module for separation, detection, and analysis.

C. DNA Quantification

In another embodiment, cartridges of this disclosure include a DNA quantification function. Such a function can be useful to meter an amount of DNA for amplification determined appropriate for down-stream applications such as STR amplification.

Figure 23:
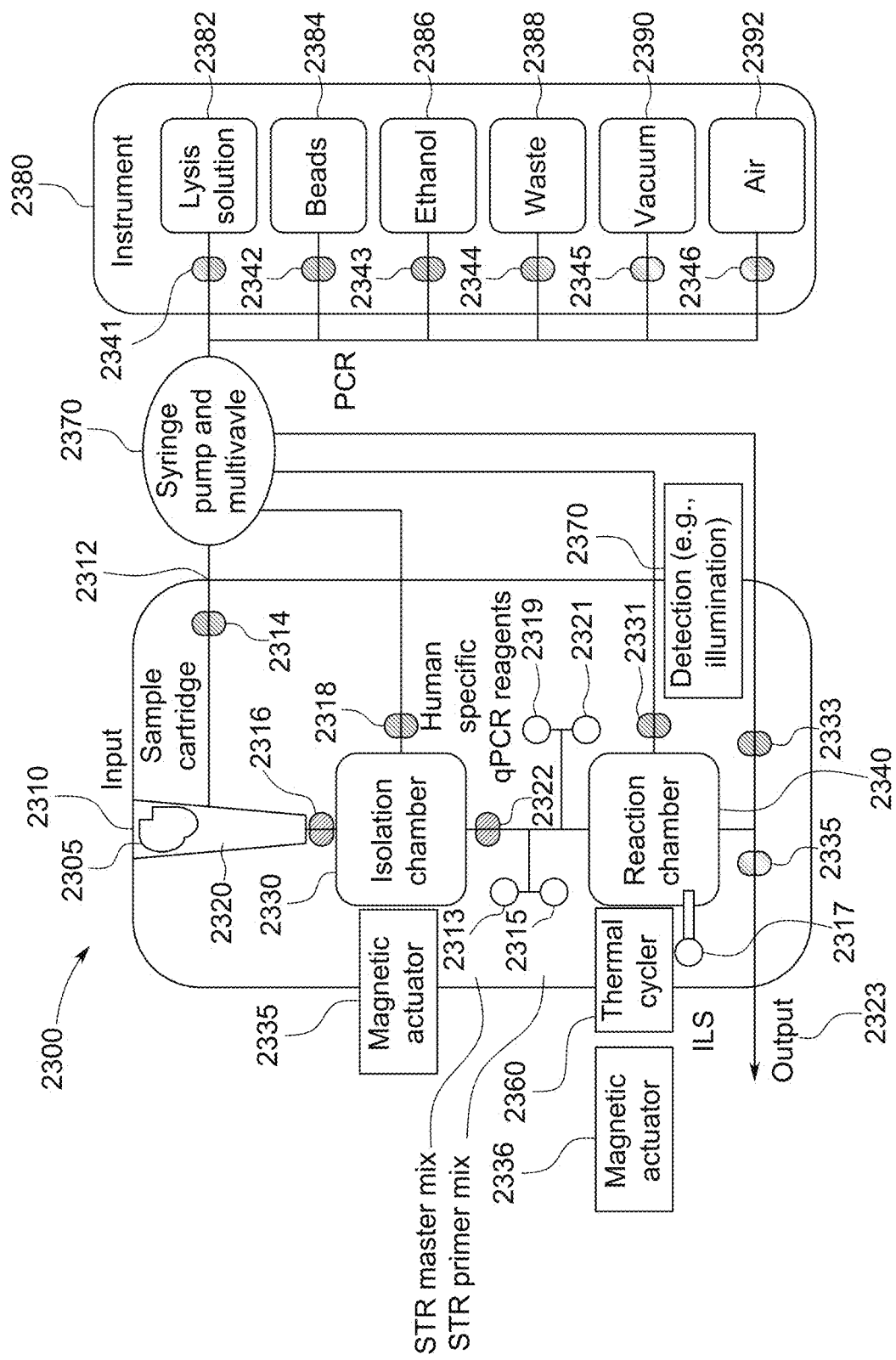
FIG. 23 shows an exemplary cartridge configured to perform real time PCR for quantifying the amount of DNA in a sample.

An exemplary cartridge 2300 for such an embodiment is shown in FIG. 23. Cartridge 2300 has input 2310. A sample 2305 can be introduced into sample chamber 2320. The cartridge can be engaged with an interface of instrument 2380 configured to supply reagents and motive forces. Cell lysis buffer contained in an off-chip reservoir 2382 can be fed through port 2312 into a fluidic channel in the cartridge and into the sample chamber 2320 by opening valve 2314. Port 2312 can be connected to a syringe 2370 or to another source of positive or negative pressure.

After lysis, lysate can be moved through a fluidic channel on the cartridge into isolation chamber 2330 by opening valve 2316. Magnetically responsive particles, e.g., beads 2384, can be introduced into the isolation chamber before or after introduction of the lysate by opening valve 2318. Polynucleotides can be captured on the particles and immobilized by application of a magnetic force to the isolation chamber 2330 by magnetic actuator 2335. The particles can be washed with, e.g., ethanol 2386, and the wash moved to a waste chamber or off-cartridge 2388.

Then, a predetermined amount of the particles with captured DNA can be moved into a reaction chamber 2340 by opening valve 2322. Magnetic actuator 2335 immobilizes the beads in reaction chamber 2340. Human-specific qPCR reagents, such as Quantifiler from Thermo Fisher Scientific™ or Plexor HY System from Promega™, are introduced into the reaction chamber from sealed compartments through ports 2319 and 2321. A thermal control mechanism in the system, e.g., thermal cycler 2360, can apply heat to perform thermal cycling in reaction chamber 2340 of the cartridge for qPCR. A detection device 2370, e.g., using illumination, determines the course of the reaction. This information is used to determine how much DNA is captured per unit bead volume. The amount of beads necessary to carry the predetermined quantity of DNA needed is calculated.

Material in reaction chamber 2340 can then be pushed, e.g., with air, 2392 through output port 2323.

Next, a volume of beads from isolation chamber 2330 determined to carry the desired amount of DNA is moved into reaction chamber 2340. Reagents for performing PCR can then be introduced into the reaction chamber, for example, from sealed compartments on the cartridge through ports 2313 and 2315, and the reaction thermal cycled.

Internal ladder standard 2317 can then be pushed, e.g., with air 2392 through output port 2323 to a capillary electrophoresis analysis module for separation, detection, and analysis.

The cartridges of this disclosure can be used in an integrated system for analyzing a sample, for example, DNA isolation and amplification with real time or end point detection. For real time measurement, the samples can be interrogated by an optical detection system while amplifying in reaction chamber 122. The readout can be the change in fluorescence or by melting point. The probes can be human specific for human identification, forensics, or molecular diagnostic applications, or specific for pathogens for molecular diagnostic applications, or for bioagents for biodefense applications or nonspecific intercalators for determining the amount of DNA present. Amplification methods include, for example, thermal or isothermal amplification reactions, for example, PCR, rolling circle amplification, whole genome amplification, nucleic acid sequence-based amplification, and single strand displacement amplification, single primer isothermal linear amplification (SPIA), loop-mediated isothermal amplification, ligation-mediated rolling circle amplification and the like.

The cartridges of this disclosure can be used in an integrated system for analyzing a sample. The assay can detect a polypeptide (e.g., immunoassay) or a nucleic acid (e.g., PCR or reverse transcriptase followed by amplification). To detect an immunoassay, after lysis of the sample and movement of the lysed sample to reaction chamber 121, ports 115 and 116 can be used to add primary and secondary antibodies to the sample. The detection can be in sample chamber 121 or the sample can be moved through port 113 to a detector.

The assay can be multiplex or single analyte. They can involve any assay to measure the presence, amount, activity, or other characteristics of the sample. These include assays that involve detection by fluorescence, luminescence, chemiluminescence, absorbance, reflectance, transmittance, birefringence, refractive index, colorimetric, and combinations thereof. In this instant disclosure, the enzyme master mix and the substrate might be individually added to the reaction and the progress or endpoint of the assay monitored optically.

In other embodiments, cartridges of this disclosure can be used to prepare samples for additional analytical devices. Analytical methods can include sequencing, chromatography, (e.g., gas or size exclusion) electrometry, ellipsometry, refractrometry, interferometry (e.g., back scattering interferometry), spectrometry (e.g., mass spectrometry, NMR spectrometry, Raman spectroscopy, Surface-enhanced Raman Spectroscopy), surface plasmon resonance. Sequencing methods can include high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS)(Helicos), massively-parallel sequencing, Clonal Single Molecule Array (Solexa), shotgun sequencing, Maxim-Gilbert sequencing, Sanger sequencing, primer walking, sequencing using PacBio, SOLID, Ion Torrent, or Nanopore platforms.

For STR applications, after thermal cycling, other reagents such as molecular weight markers (size standards) can be combined with the PCR product. Products of the PCR can be moved off chip for analysis through an output line connected to port 113 (sample out).

In such an embodiment, when the reaction is a short tandem repeat (STR) reaction, in many jurisdictions for casework samples, the amount of human DNA must be quantified. The typical forensic process is to quantify an extracted sample using real time polymerase chain reaction (PCR) in a separate instrument before the sample is STR amplified. In this instant disclosure, a human specific probe is added to the STR mixture which has fluorescence outside the range used by the STR kit. The reaction chamber 122 is interrogated by a suitable wavelength of light for the human specific probe while the STR is being PCR amplified. The human specific probe can be a quencher such as a Black Hole Quencher® or a TaqMan® probe or other chemistries well known to one skilled in the art. As the PCR cycles increase, the fluorescence from the human specific probe is monitored to quantify the amount of human DNA in the reaction. In a preferred embodiment, the number of amplification cycles can be adjusted based upon the amount of human DNA measured; this can be on a cartridge-by-cartridge monitoring if independent thermal cyclers are in use. One advantage is that the human specific probe will allow the concurrent STR amplification to achieve an optimal amplification and produce an amount of STR product that is optimal for the kit. A second advantage is the real time monitoring concurrent with the STR amplification allows integration of a sample-to-answer system without having an additional separate quantification process. A third advantage is for low copy number samples where there is barely enough sample to produce a good STR profile the integration of the quantification with the STR amplification prevents the aliquot typically used for quantification from causing the remaining sample to not have enough DNA for a good STR amplification.

EXAMPLES

Example 1

The cartridge is a polypropylene molding with an integrated syringe barrel and sample chamber with a polyethylene heat seal over the area of the fluidics. There is an absorbent material in the waste chamber and a small dot of capture material in the reaction chamber. The barrel is loaded with a quantity of lysis solution (500-1000 uL) isolated between two rubber plungers. There are three reagent vessels on the chip that seal with top and bottom Teflon balls; two for the two parts of the Global Filer mastermix/primer which are loaded with 7-10 uL of solution and one containing a water/ILS solution that is used as a diluent before transfer to the cathode.

Figure 12A:
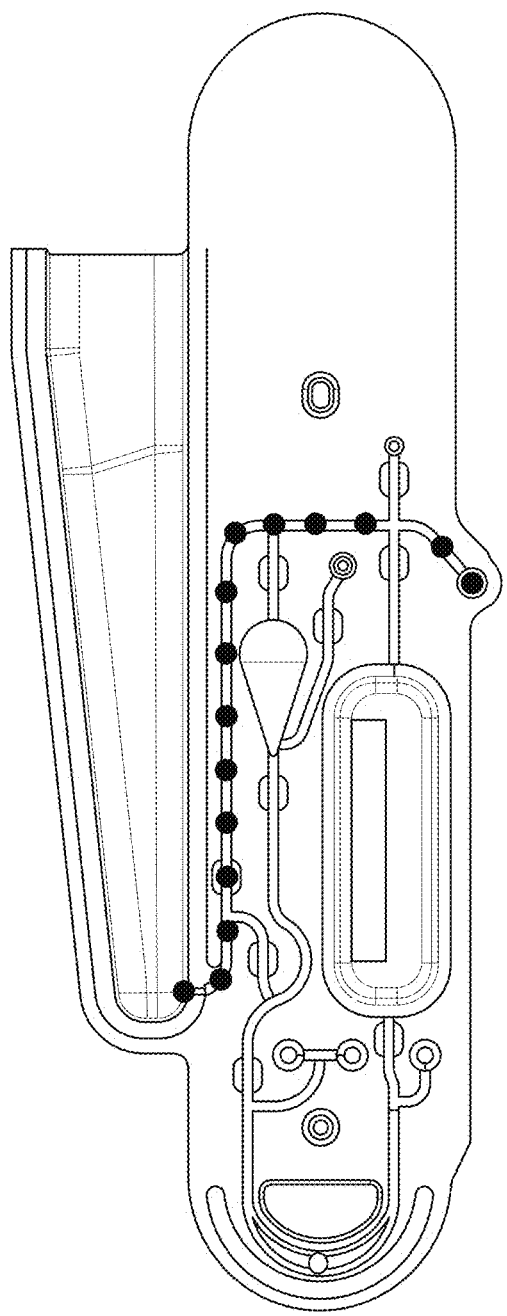
FIGS. 12A to 12E show a method of processing a sample for analysis.
Figure 12B:
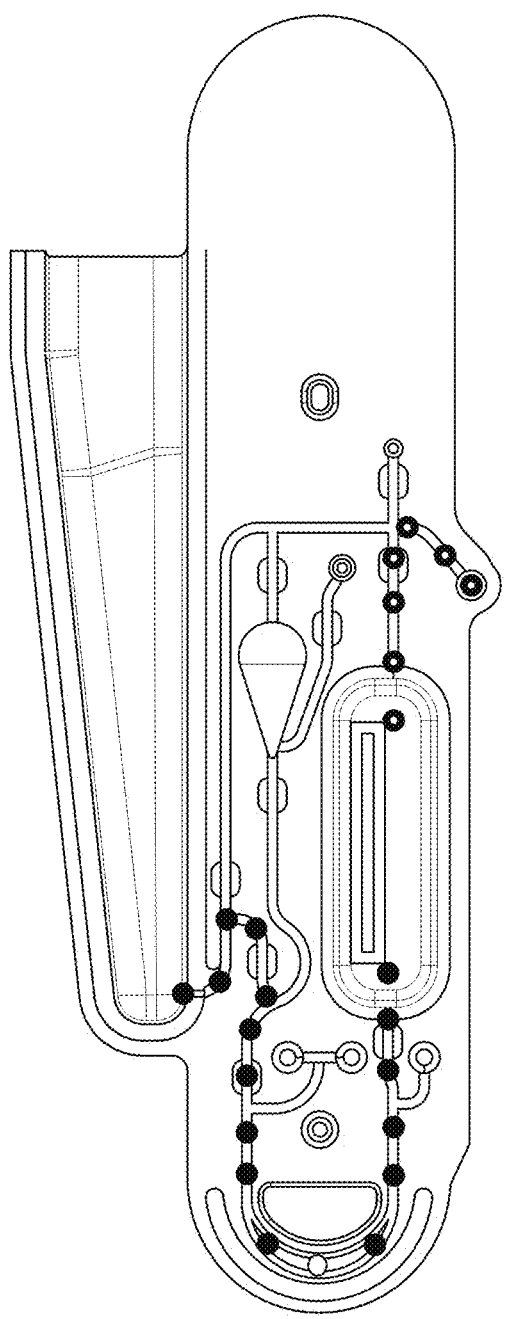
Figure 12C:
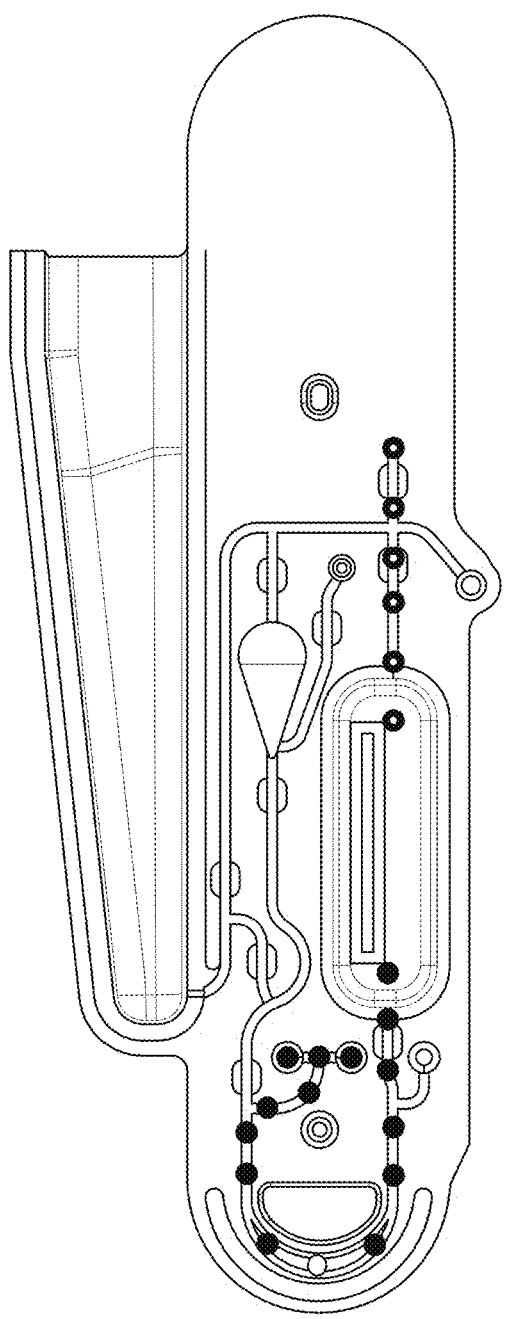
Figure 12D:
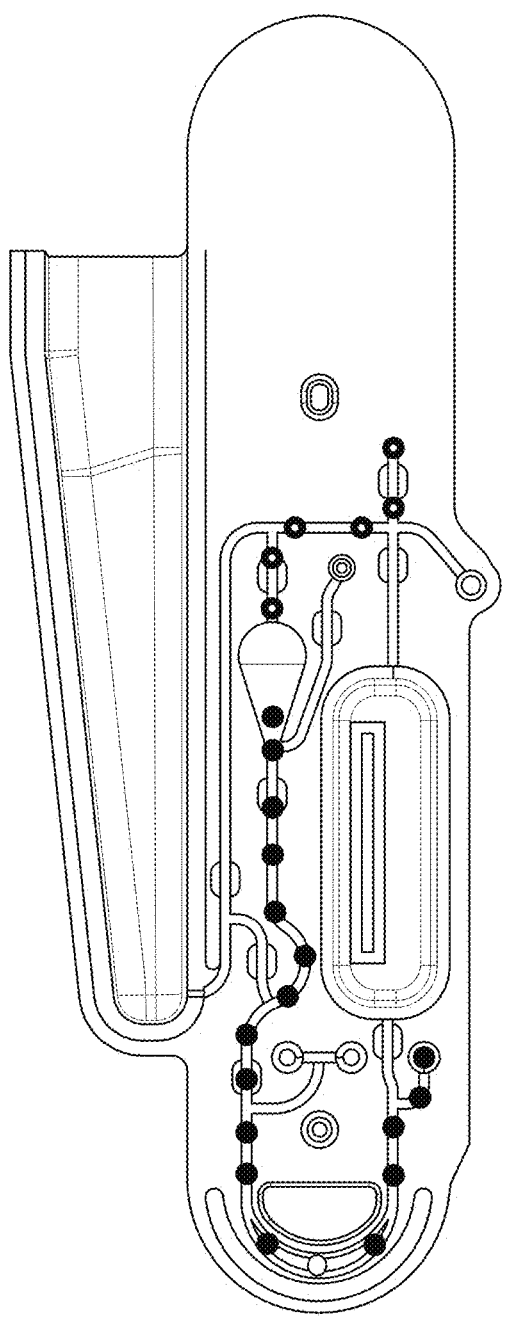

Process Steps
1. Load cartridge
   a. User removes cartridge from packaging and load into the instrument. Instrument senses cartridge and engages. The rams are in the retracted state.
   b. Initial valve coining. The rams move to the closed state.
2. Load Sample.
   a. The sample is recorded and loaded.
3. Lysis (See FIG. 12A for Path of Liquid.)
   a. The lysis heater is turned on.
   b. The valves are set to the appropriate position for delivery from the syringe to the lysis chamber.
   c. The back rubber plunger is engaged by the pump shaft on the instrument.
   d. The entire contents of the syringe is delivered to the lysis chamber.
   e. The valves are moved to the vent position.
   f. The syringe plunger is withdrawn and the syringe fills with air.
   g. The valves move to the delivery position.
   h. The air is injected into the lysis chamber to effect mixing.
4. Transfer and Capture (See FIG. 12B. Pulled by Syringe Inlet from Sample Chamber into Reaction Chamber.)
   a. The valves are set to a state where a path is open between the lysis chamber and the waste container that passes through the reaction chamber.
   b. A vacuum is pulled on the waste container.
   c. The lysate is pulled out of the chamber, through the reaction chamber and thus over the capture media, and into the waste where it is absorbed by the material in the chamber.
   d. The valves are switched to the delivery position and the plunger is brought forward.
   e. The pull is executed again to insure all the free lysate material is out of the chamber, through the reaction chamber and in the waste.
5. Mastermix/Primer Loading and Thermocycling. (See FIG. 12C. Reagents Pumped into Reaction Chamber.)
   a. The valves are set to a state where a path is open through the waste to the vent
   b. The two PCR mix vials are emptied into the reaction chamber
   c. All valves are closed.
   d. Thermocycling begins.
6. Polymer Fill, Concurrent with Cycling
   a. Open anode input and anode output valve
   b. Flush anode
   c. Close anode output valve
   d. Fill capillary
   e. Rinse Cathode
7. Mix Sample and Diluents (See FIG. 12D. Sample and Diluents to Mix Compartment.)
   a. The valves are set to a state where a path is open between the reaction chamber and the mix chamber to vent.
   b. The diluent vial is emptied up into the mix chamber.

Figure 12E:
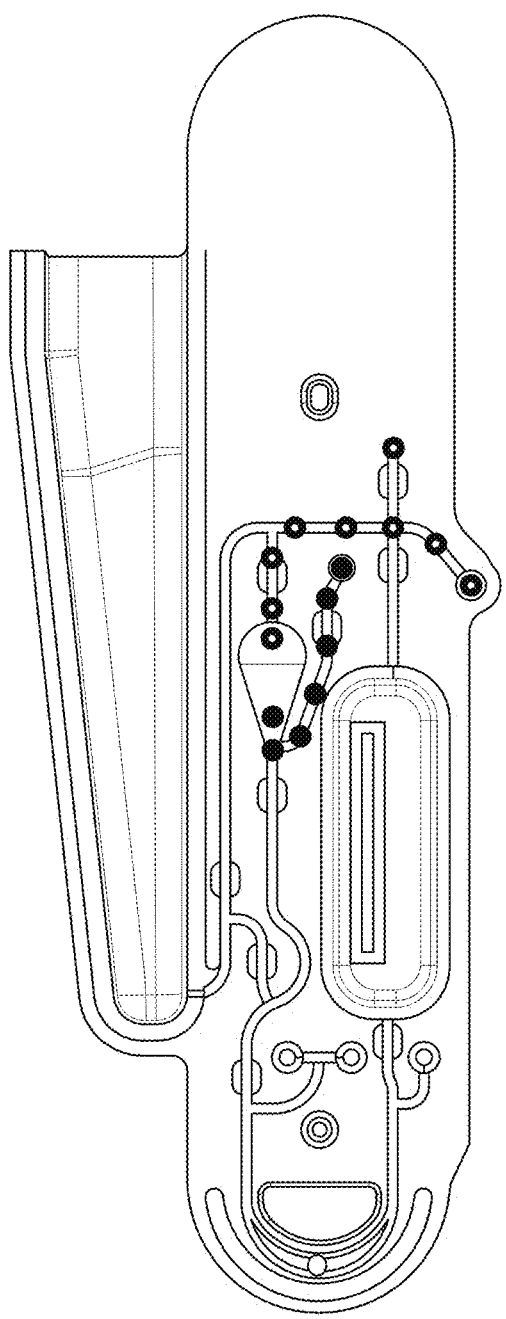
Figure 13:
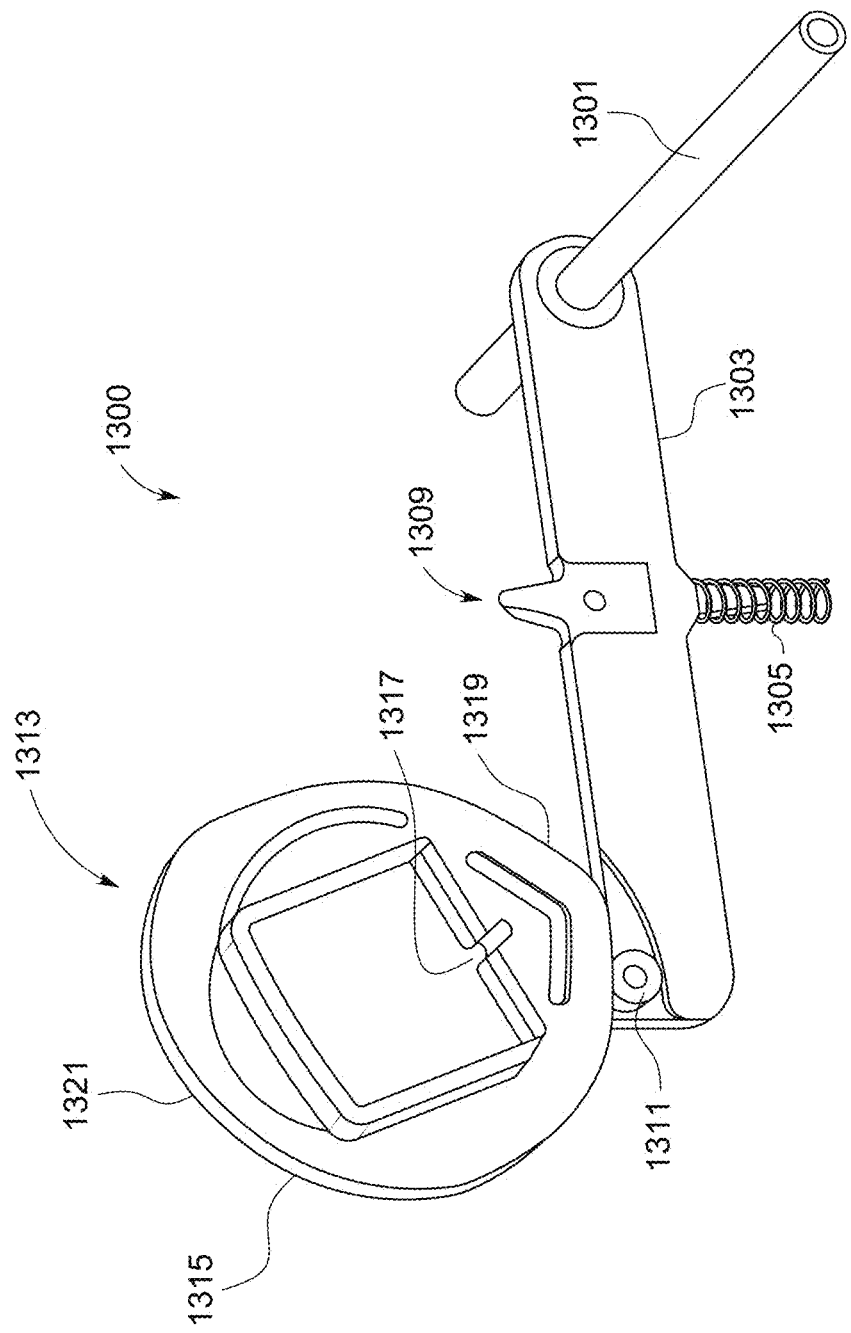
FIG. 13 shows a cam assembly comprising a ram on an axle.
Figure 14:
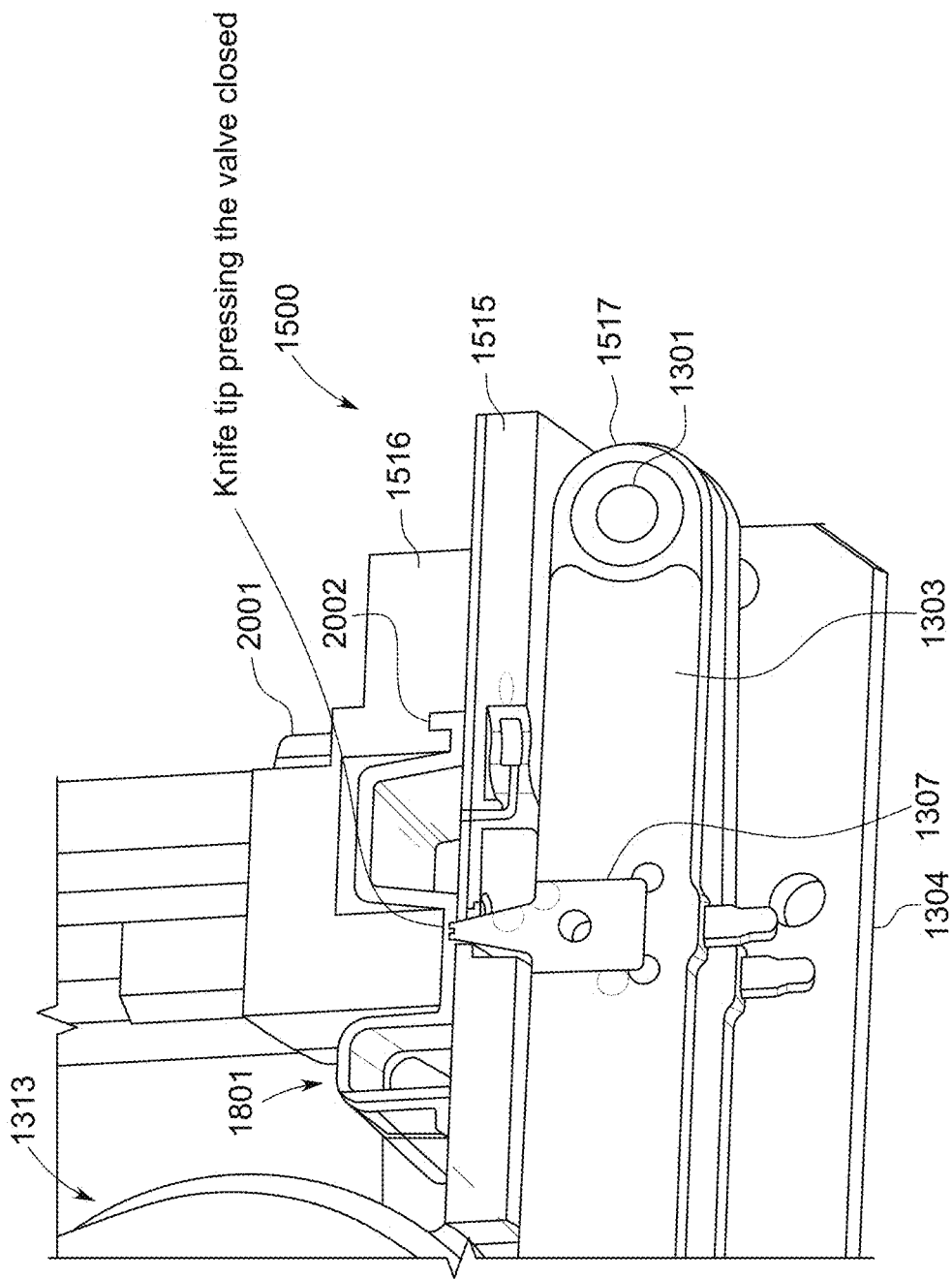
FIG. 14 shows a sectioned view shows a ram pressing against a valve.
Figure 15:
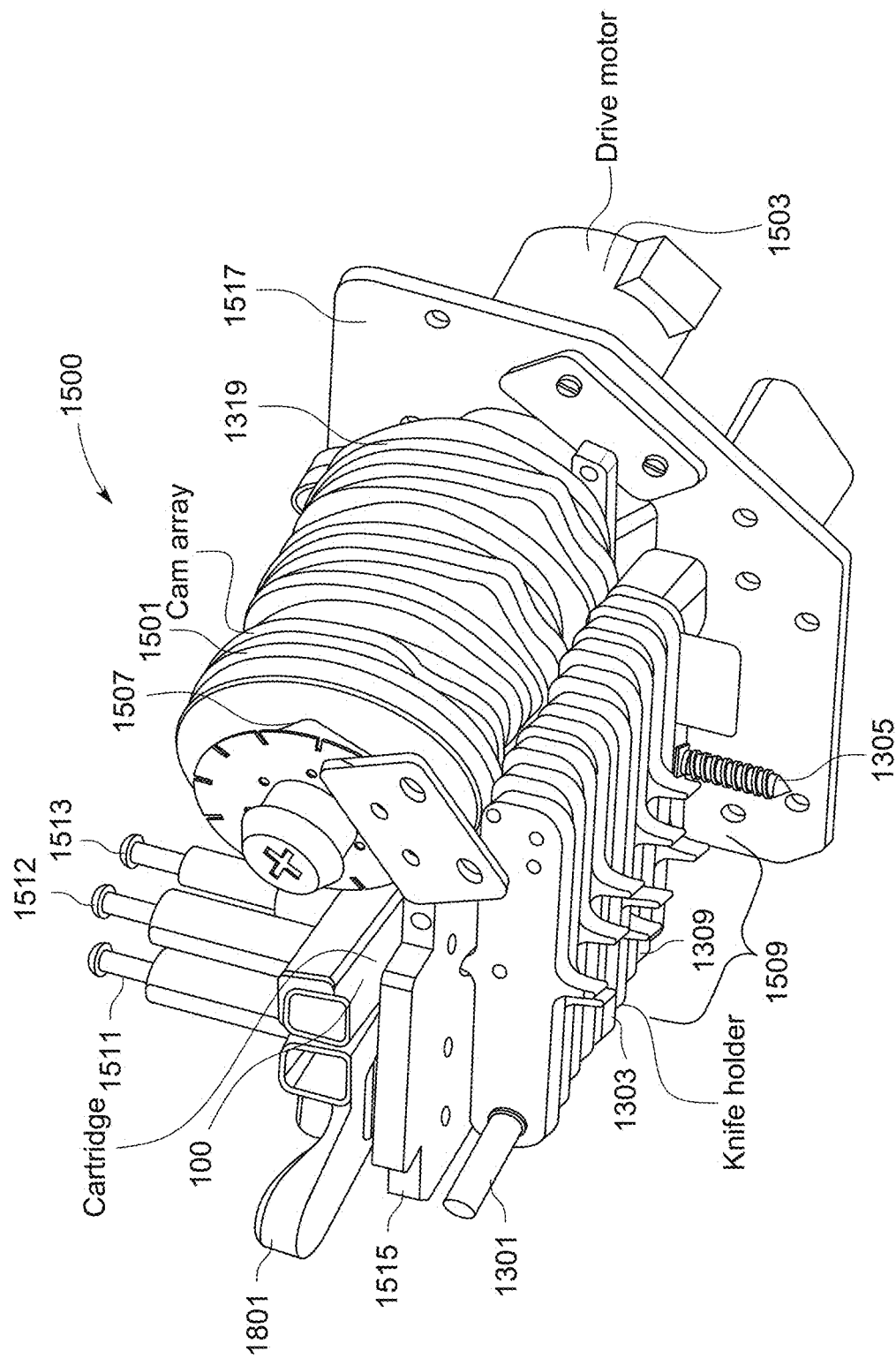
FIG. 15 shows a cam array.
Figure 16:
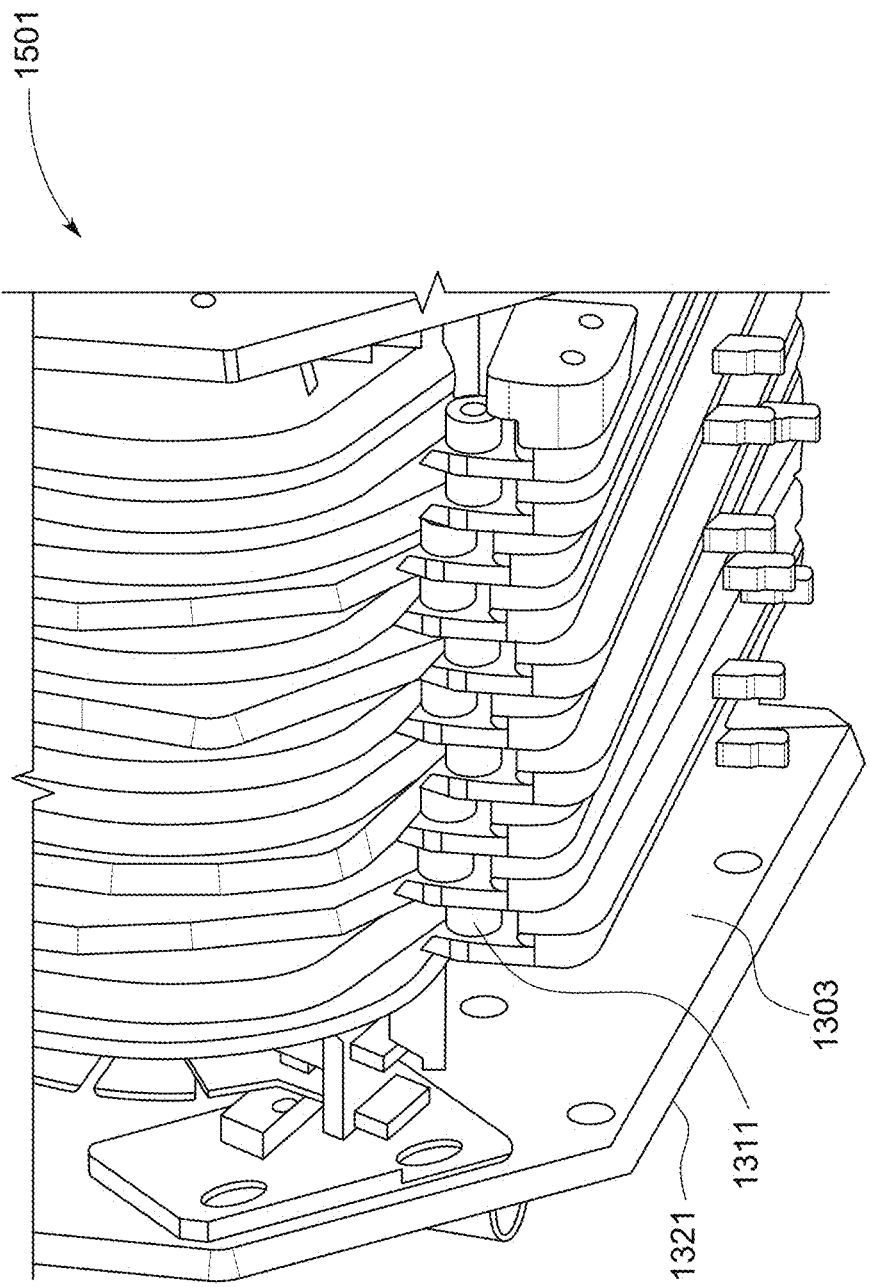
FIG. 16 shows each cam operatively engaging a lever connected to a ram.

8. Sample Delivery to Cathode (See FIG. 12E. Product Pushed to Out Port.)
   a. The valves are set to a state with a path from the syringe to the mix chamber to the sample outlet.
   b. The syringe is driven in to place the sample.
9. Sample Injection and Run
   a. The sample is injected into the capillary
   b. The buffer pump sweeps the sample out of the capillary and flushes the lines
   c. Electrophoresis and detection is run.

Example 2

Another protocol, performed on cartridge 1801, includes the following steps. Valve configurations are shown in FIG. 17.
1 Load Sample Cartridge
2 Prime Lysis to waste*
3 Dispense Lysis to Lysis Chamber
4 Mix Lysis with Air
5 Mix and Heat Lysis
6 Pull Lysate to Waste via Reaction Chamber
7 Push Primer Mix and Master Mix to Reaction Chamber
8 Thermal Cycling
9 Push Internal Lane Standard and Product thru Reaction Chamber to Mix Chamber
10 Push Residual Internal Lane Standard and Product to Mix Chamber with Air Pump
11 Push Product to Cathode
12 Water Rinse of Mix Chamber and Product Output to Cathode
13 Water Rinse of Mix Chamber and Reaction Chamber
14 Flush Water out of Sample Cartridge to Waste Chamber
15 Flush water from Sample Cartridge and Line to Cathode
16 Release
1. All 500 ul will be dispensed into the lysis chamber and then pushed into the waste chamber after step #5.
2. Residual Primer Mix and Master Mix in line to Reaction Chamber just below B0, will remain in Sample Cartridge after the run.
3. Flush Sample Cartridge free of water.

Example 3

Figure 25:
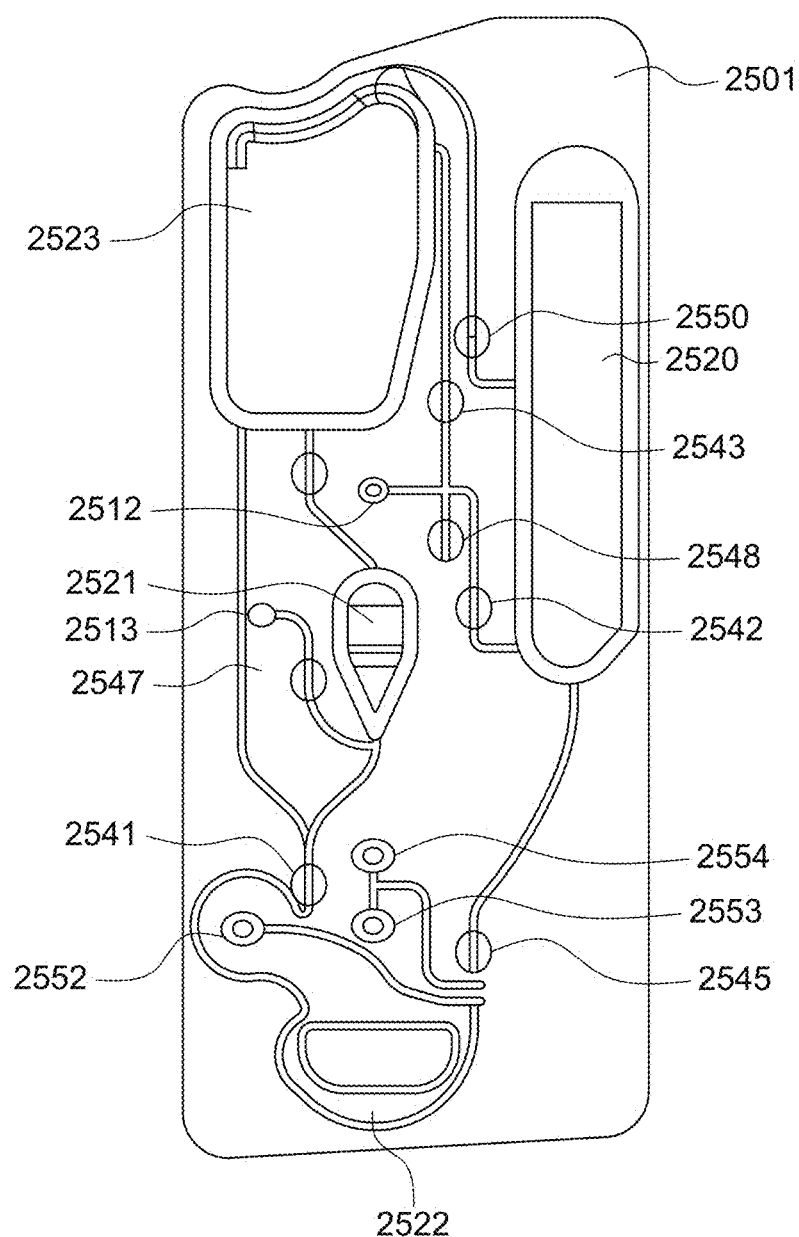
FIG. 25 shows an exemplary cartridge configuration of this disclosure.

Another protocol, performed on cartridge of FIG. 25, includes the following steps. All valves begin in open configuration.
1 Close valves 2543 and 2548. Load Sample Cartridge.
2 Push lysis buffer from port 2512 through valve 2542 to Lysis Chamber 2520
3 Mix Lysis with Air: Push air through the following open valves and forcing air through the circuit: 2512→ (open) 2543→2523→2541→2522→2545→520
4 Mix and Heat Lysis
5 Pull Lysate to Waste via Reaction Chamber 2520→2545→2522→2523→2543→2512
6 Close valve 2545; Push Primer Mix 2554 and Master Mix 2553 to Reaction Chamber 2522
7 Close valve 2541; Thermal Cycling
8 Open valve 2541; Push Internal Lane Standard 2552 and Product thru Reaction Chamber 2522 to Mix Chamber 2521
9 Push Product to Cathode 2512→2548→2521→2547→2513

Example 4

This example shows a method to perform cycle sequencing on a nucleic acid. (Refer to FIG. 21.)
Raw Sample
  Lyse with chaotroph
Bead Purify DNA
  Move to magnetic bead processing chamber
  Add paramagnetic beads
  Wash 2× with diluted ethanol
  Elute DNA or move beads to reaction chamber(s)
Perform PCR Amplification (Make Enough of Target Region to Sequence; if Multiple Regions are Being Sequenced, the Sample had to be Split or Parallel Samples for each Loci)
  Add PCR primers and premix with enzyme from vials 2113 and 2115
  Thermal cycle
ExoI/SAP (Destroys PCR Primers and Nucleotide Triphosphates)
  Add Exo/SAP reagents (Exonuclease I/Shrimp Alkaline Phosphatase)
  Incubate 37 C./for 15 min
  Heat to 80 C. for 15 min
Cycle Sequence
  Add cycle sequencing primer and premix with enzyme and BigDye terminators
  Thermal cycle
Cleanup Cycle Sequencing Products Using Paramagnetic Beads
  Move to magnetic bead processing chamber
  Add beads and chaotroph
  Wash 2× with diluted ethanol
  Elute into water or buffer
Send Products to Capillary Electrophoresis Example 5

This example shows a method to perform amplification of markers, e.g., diagnostic markers, followed by cycle sequencing of the amplification product. (Refer to FIG. 22.)
Raw Sample
  Lyse with chaotroph (on cartridge or instrument)
  Bead purify DNA
    Add beads to isolation chamber
    Wash 2× with dilute ethanol
    Elute DNA or move beads
  Purified DNA produced
  Split purified DNA to reaction chambers in aliquots
  Perform PCR amplification on each locus of interest in separate chambers
    Add PCR primers and premix with enzyme
    Thermal cycle
  Destroy PCR primers and nucleotide triphosphases
    Add Exo/SAP reagents (Exonuclease I/Shrimp Alkaline Phosphatase)
    Incubate 37° C. for ~15 min, heat to 80 C. for 15 min
  Cycle Sequence
    Add cycle sequencing primer and premix with DNA polymerase and labeled dideoxy terminators
    Thermal cycle
  Cleanup Cycle Sequencing Products
    Move cycle sequencing products to cleanup chamber and perform bead-based cleanup
    Add beads and chaotroph
    Wash 2×
    Elute Send Products to Capillary Electrophoresis Example 6

This example shows a method to quantify amount of human DNA before STR amplification for human identification or diagnostic fragment sizing (Refer to FIG. 23.)
Raw Sample
  Lyse with lysis buffer (chaotroph or something else)—bubble+heat
Bead Purify DNA
  Move lysate to magnetic bead processing chamber
  Add beads
  Wash 2×
  Move 10% beads to reaction chamber where the beads are captured by another magnet
Perform PCR Quantification
  Add Quantifiler primers and master-mix
  Thermal cycle
  Excite and detect signal and determine Ct
  Stop after reaching Ct and calculate bead dilution (optimized for downstream STR chemistry)
  Wash reaction chamber
STR Amplification in Reaction Chamber
  Pump beads from magnetic bead processing chamber through reaction chamber into waste adjusting the amount of beads captured by using the qPCR optics (with beam splitters)—i.e. "counting" beads. Actuate magnet to capture correct dilution of beads in reaction chamber.
  Add STR premix and master mix
  Thermocycle
Cleanup STR Amp Products Using a Bead-Based Cleanup (Optional Based on Quantification)
  Add beads and chaotrophs to reaction chamber
  Wash 2× with dilute ethanol
  Elute and keep beads on magnet
Add ILS
Move Amp Product to Capillary Electrophoresis System Example 7

Analyzing a Sample with an Electrophoresis Cartridge Comprising System

The electrophoresis system is highly integrated and configured to removably engage with a system for sample preparation, processing and analysis. In general, the system comprises there fully-integrated and automated components, i.e., a user interface, a sample cartridge interface and an electrophoresis cartridge interface. The sample cartridge interface and the electrophoresis cartridge interface are configured to releasably engage a sample cartridge for sample processing and an electrophoresis cartridge for sample analysis. The user interface further comprises a control module, a user interface screen and an embedded computer system. The user interface is configured to read and identify the fingerprint of a user and barcodes of sample packaging. A user inputs one or more instructions or requests via the user interface screen and the embedded computer processes the requests and transforms the requests into signals which then initiate the operation of the system.

A user removes an electrophoresis cartridge from packaging and load into the instrument. Instrument senses the cartridge and engages. Multiple communications between the electrophoresis cartridge and the system including: (i) a fluidic communication between an inlet port of the electrophoresis cartridge and an outlet port of a sample cartridge comprised in the system, (ii) an electrical communication between electrodes (i.e., anode and cathode) of the electrophoresis cartridge and a power source of the system, (iii) an optical communication between an optical window of the electrophoresis cartridge and an optics module of the system, (iv) a first thermal communication between the electrophoresis capillary and a first thermo control assembly of the system, (v) a second thermal communication between a gel sub-cartridge of the electrophoresis cartridge and a second thermal control assembly of the system, (vi) a first mechanical communication between an anode sub-assembly of the electrophoresis cartridge and a first mechanical interface of the system, (vii) a second mechanical communication between a cathode sub-assembly of the electrophoresis cartridge and a second mechanical interface of the system, and (viii) a magnetic communication between the electrophoresis cartridge and the system, are established concurrently with the engagement of the electrophoresis cartridge.

Electrophoresis gel stored in the gel sub-cartridge is pumped and injected into the electrophoresis capillary by a high pressure piston comprised in the anode sub-assembly. As the gel is injected, a washing buffer is pumped into a passage of the cathode sub-assembly for removing excessive gel in the cathode sub-assembly. Subsequently, a prepared analyte is directed into the electrophoresis capillary from the sample line in the cathode sub-assembly. A voltage gradient is then applied across two ends of the electrophoresis capillary to perform electrophoretic analysis and separate different components of the analyte which emit distinguishable optical signals upon the illumination of a laser. The signals are detected by a CCD camera comprised in the optics module and subjected to further analysis. Conclusion is drawn based on the results.

Another exemplary cartridge is depicted in FIGS. 32A and 32B.

All publications and patent applications mentioned in this specification are herein incorporated by reference to the same extent as if each individual publication or patent application was specifically and individually indicated to be incorporated by reference.

While preferred claims of the present invention have been shown and described herein, it will be obvious to those skilled in the art that such claims are provided by way of example only. Numerous variations, changes, and substitutions will now occur to those skilled in the art without departing from the invention. It should be understood that various alternatives to the claims of the invention described herein may be employed in practicing the invention. It is intended that the following claims define the scope of the invention and that methods and structures within the scope of these claims and their equivalents be covered thereby.

What is claimed is:
1. An instrument comprising a cartridge interface and a cartridge engaged with the cartridge interface, wherein:
  a cartridge comprising:
  a body comprising a malleable material, and
  a layer comprising a deformable material bonded to a surface of the body and sealing one or more fluidic channels that communicate with one or more valve bodies formed in a surface of the body,
  wherein:
  the one or more valve bodies comprise:
    a segment of the channel comprising a wall having a pair of ridges and a floor depressed into the surface, and reliefs depressed into the surface and defining depressions that flank the ridges on two sides of the segment of the channel; and the layer is bonded to the surface of the body and to the ridges such that the one or more channels, channel segments and reliefs are sealed, and wherein a valve body sealed with the layer forms a valve closable by forcing the layer against the floor of the segment of the channel; and a cartridge interface comprising a plurality of rams, each ram positioned to actuate a valve of the cartridge and comprising a head having a widest dimension that is wider than a channel segment and less wide than a width between the reliefs, so that, when actuated toward the valve, the head presses the deformable material against the ridges and the floor, thereby closing the valve, but clearing the reliefs.

2. The instrument of claim 1 wherein the cartridge interface has a substantially planar face configured to mate with a substantially planar surface of the cartridge.

3. The instrument of claim 1 wherein the rams are retractable toward the interface and are spring biased toward the cartridge.

4. The instrument of claim 1 wherein the head has a length:width ratio of at least any of 2:1, 3:1, 4:1, 5:1, 6:1, 7:1, 8:1, 9:1 or 10:1.

5. The instrument of claim 1 wherein the head has an edge in its longest aspect that is substantially straight and either substantially flat or curved no more than a depth of a valve relief.

6. The instrument of claim 1 wherein each ram is comprised in a cam mechanism, wherein rotation of the cam actuates the ram toward or away from the valve.

7. The instrument of claim 1 wherein the cartridge interface further comprises a cover plate configured to receive the cartridge and comprising at least one plunger positioned to actuate at least one valve in cartridge.

8. The instrument of claim 1 wherein the cartridge interface further comprises a cover plate comprising a fluid inlet line that engages an inlet port on the cartridge and/or a fluid outlet line that engages an exit port on the cartridge.

9. The instrument of claim 1 wherein the cartridge is configured to receive one or more samples and to perform nucleic acid extraction and isolation, and DNA amplification when the cartridge is engaged with a cartridge interface.

10. The instrument of claim 1 further comprising a sample analysis module in fluidic communication with a port in the cartridge interface that communicates with a reaction chamber of the engaged cartridge.

11. The instrument of claim 10 wherein the sample analysis module comprises an electrophoresis assembly comprising a capillary comprising a medium adapted for capillary electrophoresis and a cathode and anode configured to place a voltage across the capillary.

12. The instrument of claim 11 wherein the sample analysis module further comprises a detection assembly for detecting molecules in the capillary.

13. The instrument of claim 12 wherein the detection assembly comprises a laser and a detector for detecting laser light.

14. The instrument of claim 10 wherein the sample analysis module comprises a chromato graph, a DNA sequencer, an electrophoresis instrument, an electrometer, an ellipsometer, an interferometer, a mass spectrometer, an NMR spectrometer, a spectrometer a thermometer, a voltmeter.

15. The instrument of claim 1 wherein the instrument comprises an actuator, e.g., a plunger, configured to move one or more reagents from sealed compartments on the cartridge into fluidic channels of the cartridge.

16. The instrument of claim 1 further comprising a source of magnetic force configured to exert a magnetic force against a chamber in the cartridge.

17. A method of controlling fluid flow in a fluid channel of fluidic cartridge comprising:
(A) providing an instrument of claim 1 wherein at least one of the fluidic channels comprises a liquid;
(B) closing a valve by actuating a ram head against the valve to force the deformable layer against the floor of the channel segment;
(C) releasing the valve by retracting the ram head from the layer; and
(D) moving the liquid through the valve by applying pressure to liquid in a fluidic channel, wherein fluid under pressure opens the valve.

18. The method of claim 17 further comprising, after step (D):
(E) re-closing the valve by actuating a ram head against the valve to force the deformable layer against the channel segment floor.

19. The method of claim 17 wherein the pressure is sourced through a pump internal to the cartridge or a pump external to the cartridge (e.g., a syringe) and delivered, optionally, through an inlet in the cartridge connected to a fluidic channel in the cartridge.

20. A method performed using a cartridge of claim 1 comprising:
moving an extraction medium through at least one open valve in the cartridge to an extraction chamber in the cartridge comprising a biological sample and lysing cells in the biological sample to create an extract;
moving the extract through at least one open valve in the cartridge to a reaction chamber in the cartridge;
moving reagents for performing a biochemical reaction into the reaction chamber to create a mixture;
performing a biochemical reaction on the mixture to create a reaction product; and
performing analysis on the reaction product.

* * * * *